(12) United States Patent
Protter et al.

(10) Patent No.: US 7,268,139 B2
(45) Date of Patent: *Sep. 11, 2007

(54) METHODS OF PROMOTING OSTEOGENESIS

(75) Inventors: Andrew A. Protter, Palo Alto, CA (US); David Y. Liu, Palo Alto, CA (US); Patrick O'Connor, Farnwood, NJ (US)

(73) Assignee: Scios, Inc., Fremont, CA (US)

( * ) Notice: Subject to any disclaimer, the term of this patent is extended or adjusted under 35 U.S.C. 154(b) by 88 days.

This patent is subject to a terminal disclaimer.

(21) Appl. No.: 10/651,934

(22) Filed: Aug. 29, 2003

(65) Prior Publication Data

US 2004/0162289 A1    Aug. 19, 2004

Related U.S. Application Data

(60) Provisional application No. 60/406,664, filed on Aug. 29, 2002.

(51) Int. Cl.
| | | |
|---|---|---|
| A61K 31/497 | (2006.01) | |
| A61K 31/445 | (2006.01) | |
| A61K 31/415 | (2006.01) | |
| A61K 31/38 | (2006.01) | |
| A61K 31/385 | (2006.01) | |

(52) U.S. Cl. .................... 514/252.13; 514/254.09; 514/330; 514/407; 514/438; 514/442; 514/474

(58) Field of Classification Search ........... 514/252.13, 514/254.09, 330, 407, 438, 442, 474
See application file for complete search history.

(56) References Cited

U.S. PATENT DOCUMENTS

| | | | | |
|---|---|---|---|---|
| 4,107,288 | A | 8/1978 | Oppenheim et al. | 424/22 |
| 4,619,652 | A | 10/1986 | Eckenhoff et al. | 604/415 |
| 5,145,684 | A | 9/1992 | Liversidge et al. | 424/489 |
| 6,410,540 | B1 * | 6/2002 | Goehring et al. | 514/252.13 |

FOREIGN PATENT DOCUMENTS

| | | |
|---|---|---|
| CA | 2356263 | 7/2000 |
| WO | WO96/21452 | 7/1996 |
| WO | WO96/21654 | 7/1996 |
| WO | WO96/40143 | 12/1996 |
| WO | WO97/25046 | 7/1997 |
| WO | WO97/35856 | 10/1997 |
| WO | WO98/25619 | 6/1998 |
| WO | WO98/56377 | 12/1998 |
| WO | WO98/57966 | 12/1998 |
| WO | WO99/32110 | 7/1999 |
| WO | WO99/32121 | 7/1999 |
| WO | WO99/32463 | 7/1999 |
| WO | WO99/57101 | 11/1999 |
| WO | WO99/61440 | 12/1999 |
| WO | WO99/64400 | 12/1999 |
| WO | WO 00/10563 | 3/2000 |
| WO | WO 00/12074 | 3/2000 |
| WO | WO 00/17204 | 3/2000 |
| WO | WO 00/19824 | 4/2000 |
| WO | WO 00/26209 | 5/2000 |
| WO | WO 00/41698 | 7/2000 |
| WO | WO 00/64422 | 11/2000 |
| WO | WO 00/71535 | 11/2000 |
| WO | WO 01/05749 | 1/2001 |
| WO | WO 01/10865 | 2/2001 |
| WO | WO 01/38324 | 5/2001 |
| WO | WO 01/64679 | 9/2001 |
| WO | WO 01/66539 | 9/2001 |
| WO | WO 01/66540 | 9/2001 |
| WO | WO 02/07772 | 1/2002 |

OTHER PUBLICATIONS

De Laszlo et al. "Pyrroles and Other Heterocycles as Inhibitors of P38 Kinase", Bioorganic & Medicinal Chemistry Letters vol. 8, pp. 2689-2694 (1998).*
Tuli et al., "p38 MAP Kinase Regulation of AP-2 Binding in TGF-beta 1-Stimulated Chrondrogenesis of Human Trabecular Bone-Derived Cells", Annals of New Yorks Academy of Science, vol. 961, pp. 172-177 (2002).*
International Search Report for PCT/US03/26839, mailed on Aug. 16, 2004, 4 pages.
Adams et al., Bioorg. Med. Chem. Lett., 8:3111-3116 (1998).
Adler, Bone Diseases, p. 114(Springer-Verlag, Germany 2000).
Bell et al., J. Physiol., 100:299-317 (1941).
Bonnarens and Einhorn, J. Orthop. Res., 2:97-101 (1984).
Collis et al., Bioorg. Med. Chem. Lett., 11:693-696 (2001).
De Laszlo et al., Bioorg. Med. Chem. Lett., 8:2698 (1998).
Engesaeter et al., Acta Orthop. Scand., 49:512-518 (1978).
Fijen et al., Clin. Exp. Immunol., 124:16-20 (2001).
Gallagher et al., Bioorg. Med. Chem., 5:49-64 (1997).
Jiang et al., J. Biol. Chem., 271:17920-17926 (1996).
Kimble et al., Endocrinol., 136:3054-3061 (1995).
Kumar et al., Biochem. Biophys. Res. Comm., 235:533-538 (1997).
Lee et al., Bone, 30(1):71-77 (2002).
Li et al., Biochem. Biophys. Res. Comm., 228:334-340 (1996).
Li et al., Endocrinology, 143:3105-3113 (2002).
Matsumoto et al., FEBS Lett., 486:23-28 (2000).
Matsumoto et al., J. Biol. Chem., 275:31155-31161 (2000).
McLay et al., Bioorg. Med. Chem., 9:537-554 (2001).
Poste, Meth. Cell Biol. 14:33-71 (1976).

(Continued)

Primary Examiner—Raymond J. Henley, III
(74) Attorney, Agent, or Firm—Morrison & Foerster LLP

(57) ABSTRACT

The invention is directed to methods of bone healing by administering a p38 MAP kinase inhibitor. The invention is directed to methods of treating bone fractures, bone diseases, bone grafting, especially enhancing bone healing following facial reconstruction, maxillary reconstruction, mandibular reconstruction or tooth extraction, enhancing long bone extension, enhancing prosthetic ingrowth, and increasing bone synostosis by administering a p38 MAP kinase inhibitor.

7 Claims, 13 Drawing Sheets

OTHER PUBLICATIONS

Report of a World Health Oraganization Study Group, World Health Organization Technical Series 843, "Assessment of a Fracture Risk and its Application to Screening for Postmenopausal Osteoporosis" (1994).
Revesz et al., Bioorg. Med. Chem. Lett., 10:1261-1264 (2000).
Simon et al., J. Bone Miner. Res., 17:963-976 (2002).
Stein et al., J. Biol. Chem. 272:19509-19517 (1997).
Wadsworth et al., J. Pharmacol. Expt. Therapeut., 291:680-687 (1999).
Wang et al., J. Biol. Chem., 272:23668-23674 (1997).
Wang et al., J. Biol. Chem., 273:2161-2168 (1998).

* cited by examiner

Rat 65

Rat 67

Rat 81

Rat 87

Rat 92

Rat 98

Rat 109

Rat 114

Rat 118

Rat 80

Rat 104

Rat 96

Rat 107

Rat 97

Rat 123

Rat 60

Rat 61

Rat 78

Rat 84

Rat 94

Rat 64

Rat 68

Rat 85

Rat 90

Rat 95

Rat 102

Rat 108

Rat 115 p38 Inhibitor reduces cartilage and bone destruction in the early stage arthritis

METHODS OF PROMOTING OSTEOGENESIS

CROSS-REFERENCE TO RELATED APPLICATIONS

This application claims priority from U.S. patent application Ser. No. 60/406,664 filed 29 Aug. 2002. The contents of that document are incorporated herein by reference.

BACKGROUND OF THE INVENTION

1. Field of the Invention

The invention is directed to methods of promoting osteogenesis by administering a p38 MAP kinase inhibitor. More specifically, the invention is directed to methods of treating bone fractures, bone diseases, bone grafting, especially enhancing bone healing following facial reconstruction, maxillary reconstruction, mandibular reconstruction or tooth extraction, enhancing long bone extension, enhancing prosthetic ingrowth, and increasing bone synostosis by administering a p38 MAP kinase inhibitor.

2. Background

Bone is subject to constant breakdown and resynthesis in a complex process mediated by osteoblasts, which produce new bone, and osteoclasts, which destroy bone. Osteoblasts secrete osteoid, the unmineralized organic matrix that subsequently undergoes mineralization which provides strength and rigidity to bone.

One condition in which enhanced bone formation is required is bone fracture. After a bone fracture, it is desirable to stimulate bone growth so as to hasten and complete bone repair. There are approximately six million bone fractures in the United States each year. The complication rate associated with fracture healing has been estimated at 5-10%. Complications such as non-union, delayed union, and malunion can occur. The etiology of the complications remains unknown but certain factors are known to negatively affect the outcome of fracture healing. These effects include age, diabetes, and NSAID (non-steroidal anti-inflammatory drug) use.

Fracture healing is a complex process. Preferably the fracture healing process restores a broken bone to its prior metabolic and mechanical functional state. The initial events that occur following a fracture include tissue hypoxia and hematoma formation. The tissue hypoxia and hematoma formation quickly lead to inflammation and edema in the soft tissues surrounding the fracture site. Cell proliferation soon begins to occur rapidly in the periosteum (the osteoblast cell layer around the bone) within the vicinity of the fracture site called the fracture callus. Mesenchymal cell migration falls rapidly during the inflammation phase and it is thought that the fibrin clot formed from the hematoma acts as a source for cell attachment at the fracture site for the migrating cells. The source of the migrating mesenchymal cells remains controversial but probably includes circulating mesenchymal stem cells mobilized from the bone marrow, vascular pericytes, and proliferating muscle satellite cells. The cells that have migrated into the fracture site differentiate into chondrocytes and form a cartilaginous matrix. Endochondral ossification progressively proceeds from the junction between the osteoblasts that have proliferated from the periosteum and the differentiated chondrocytes within the fracture site so that new bone formed from endochondral ossification fills the fracture callus from the periphery to the actual fracture site. Chondrocytes at the osteoblast-chondrocyte boundary terminal differentiate into hypertrophic chondrocytes, express Type X collagen, secrete angiogenic factors, and mineralize the cartilaginous matrix (calcified cartilage). Osteoblasts at the osteoblast-chondrocyte junction secrete new bone. As angiogenesis occurs at this boundary, osteoclasts migrate into the area, resorb the calcified cartilage, which is then replaced with new bone secreted from the osteoblasts. Ultimately, this process bridges the fracture site and the bone is remodeled based upon the mechanical stresses imposed upon the bone.

Protein kinases are involved in various cellular responses to extracellular signals. p38 Mitogen-Activated Protein (MAP) kinase (also called p38 kinase or "High Osmolarity Glycerol response kinase" (HOG)) is a member of a family of signaling molecules known as the Mitogen-Activated Protein kinase (MAP kinase or MAPK) family. Other members of the MAP kinase family include the classical MAPKs termed Extracellular signal Regulated Kinases (ERK), which are activated by a variety of mitogenic stimuli as well as differentiation signals, and Stress-Activated Protein Kinases (SAPK) (also called Jun N-terminal Kinases (JNK)). SAPKs are activated by stresses but not mitogens, like the p38 MAP kinase.

p38 MAP kinase is activated by a variety of cellular stressors, including ultraviolet radiation, osmotic shock, and inflammatory cytokines, such as interleukin-1 (IL-1) and tumor necrosis factor-α (TNF-α). Once activated, p38 MAP kinase mediates the induction of mRNA synthesis for a variety of inflammatory mediators, including IL-1β, TNF-α, IL-6, and cyclo-oxygenase-2 (COX-2).

Four isoforms of p38 MAP kinase have been identified and are designated as p38α, p38γ, p38δ and p38δ (Jiang, Y. et al., *J. Biol. Chem.* 271:17920-17926 (1996); Kumar, S. et al., *Biochem. Biophys. Res. Comm.* 235:533-538 (1997); Stein, B. et al., *J. Biol. Chem.* 272:19509-19517 (1997); Li, Z. et al., *Biochem. Biophys. Res. Comm.* 228:334-340 (1996); Wang, X. et al., *J. Biol. Chem.* 272:23668-23674 (1997)). p38α is also referred to as p38. p38β is also referred to as p38-2. p38γ is also referred to as ERK6. These isoforms differ in tissue expression patterns, substrate utilization, response to direct and indirect stimuli, and susceptibility to kinase inhibitors. For example, one study has demonstrated the activation of p38β MAP kinase results in myocyte hypertrophy, while the activation of p38α MAP kinase leads to myocyte apoptosis (Wang, Y. et al., *J. Biol. Chem.* 273:2161-2168 (1998)).

Inhibition of p38 MAP kinase leads to a blockade on the production of both IL-1 and TNF. IL-1 and TNF stimulate the production of other proinflammatory cytokines such as IL-6 and IL-8 and have been implicated in acute and chronic inflammatory diseases and in postmenopausal osteoporosis (Kimble, R. B. et al., *Endocrinol.* 136:3054-3061 (1995)). Based upon this finding it is believed that p38 MAP kinase, along with other MAPKs, have a role in mediating cellular response to inflammatory stimuli, such as leukocyte accumulation, macrophage/monocyte activation, tissue resorption, fever, acute phase responses and neutrophilia. In addition, MAPKs, such as p38 MAP kinase, have been implicated in cancer, thrombin-induced platelet aggregation, immunodeficiency disorders, autoimmune diseases, cell death, allergies, osteoporosis and neurodegenerative disorders. Other diseases associated with IL-1, IL-6, IL-8 or TNF overproduction are set forth in WO 96/21654.

SUMMARY OF THE INVENTION

The invention is directed to a method of promoting osteogenesis in a patient, the method comprising administering a pharmaceutically effective amount of a p38 mitogen activated protein (MAP) kinase inhibitor to the patient in need of osteogenesis.

The invention is also directed to a method of treating bone fracture in a patient, the method comprising administering a pharmaceutically effective amount of a p38 mitogen activated protein (MAP) kinase inhibitor to the patient in need of treatment of bone fracture. The term "bone fracture" includes, but is not limited to, a traumatic bone fracture or a long-term fracture.

The invention is also directed to a method of enhancing bone grafting in a patient, the method comprising administering a therapeutically effective amount of a p38 mitogen activated protein (MAP) kinase inhibitor to the patient in need of enhanced bone grafting.

The invention is further directed to a method of treating a bone disease in a patient, the method comprising administering a pharmaceutically effective amount of a p38 mitogen activated protein (MAP) kinase inhibitor to the patient in need of treatment of a bone disease.

The invention is also directed to a method of reducing bone resorption in a patient, the method comprising administering a therapeutically effective amount of a p38 mitogen activated protein (MAP) kinase inhibitor to the patient in need of treatment of bone resorption, thereby increasing bone mass in the patient.

The invention is also directed to a method of enhancing bone healing following facial reconstruction, maxillary reconstruction, mandibular reconstruction or tooth extraction, and to enhancing long bone extension, enhancing prosthetic ingrowth or increasing bone synostosis in a patient, the method comprising administering a therapeutically effective amount of a p38 mitogen activated protein (MAP) kinase inhibitor to the patient in need thereof.

The invention is also directed to a method of increasing bone mass in a mammal, the method comprising administering a pharmaceutically effective amount of a p38 mitogen activated protein (MAP) kinase inhibitor to the mammal in need of increased bone mass.

The invention is also directed to a method of decreasing osteoclast numbers in a patient, the method comprising administering a pharmaceutically effective amount of a p38 mitogen activated protein (MAP) kinase inhibitor to the patient in need of decreased osteoclasts.

The invention is also directed to a method of increasing chondrocyte differentiation in a patient, the method comprising administering a pharmaceutically effective amount of a p38 mitogen activated protein (MAP) kinase inhibitor to the patient in need of increased chondrocyte differentiation.

The invention is further directed to a method of accelerating calcified cartilage formation in a patient, the method comprising administering a pharmaceutically effective amount of a p38 mitogen activated protein (MAP) kinase inhibitor to the patient in need of accelerated calcified cartilage formation.

The invention is also directed to a method of increasing or enhancing the rate of bone growth in a mammal, the method comprising administering a therapeutically effective amount of a p38 mitogen activated protein (MAP) kinase inhibitor to the mammal in need of increased or enhanced rate of bone growth.

BRIEF DESCRIPTION OF THE FIGURES

FIG. 1A. Rat 65. FIG. 1B. Rat 67. FIG. 1C. Rat 81. FIG. 1D. Rat 87. FIG. 1E. Rat 92. FIG. 1F. Rat 98. FIG. 1G. Rat 109. FIG. 1H. Rat 114. FIG. 1I. Rat 118.

FIG. 2A. Rat 80. FIG. 2B. Rat 96. FIG. 2C. Rat 97. FIG. 2D. Rat 104. FIG. 2E. Rat 107. FIG. 2F. Rat 123.

FIG. 3A. Rat 60. FIG. 3B. Rat 61. FIG. 3C. Rat 78. FIG. 3D. Rat 84. FIG. 3E. Rat 94.

FIG. 4A. Rat 64. FIG. 4B. Rat 68. FIG. 4C. Rat 85. FIG. 4D. Rat 90. FIG. 4E. Rat 95. FIG. 4F. Rat 102. FIG. 4G. Rat 108. FIG. 4H. Rat 115.

FIG. 5A. Normalized peak torque at 4 weeks post-fracture. FIG. 5B. Normalized torsional rigidity at 4 weeks post-fracture. FIG. 5C.

FIG. 6A. Control. FIG. 6B. Rofecoxib. FIG. 6C. p38 MAP kinase inhibitor, once per day. FIG. 6D. p38 MAP kinase inhibitor, twice per day.

FIG. 8A. Control, at 2 weeks. FIG. 8B. Rofecoxib, at 2 weeks. FIG. 8C. p38 MAP kinase inhibitor, once per day, at 2 weeks. FIG. 8D. p38 MAP kinase inhibitor, twice per day, at 2 weeks. FIG. 8E. p38 MAP kinase inhibitor, twice per day, at 4 weeks.

FIG. 10A is a graphical representation of clinical manifestations of arthritis over time. FIG. 10B is a graphical representation of cartilage oligo matrix protein levels in native, control and treated populations. FIG. 10C is a histological analysis of bone and cartilage destruction in advanced stage arthritis. FIG. 10D is a graphical representation of osteoclast numbers in advanced stage arthritis.

DETAILED DESCRIPTION OF THE INVENTION

Osteogenesis

Figure 1A:
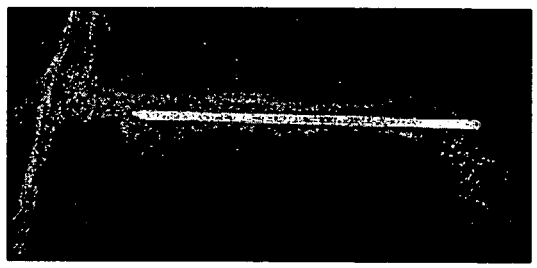
FIGS. 1A-1I. Radiographs from control rats at 4 weeks post-fracture.
Figure 1B:
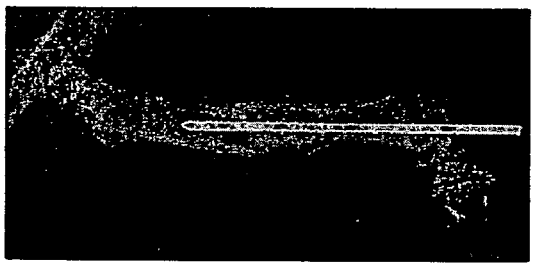
Figure 1C:
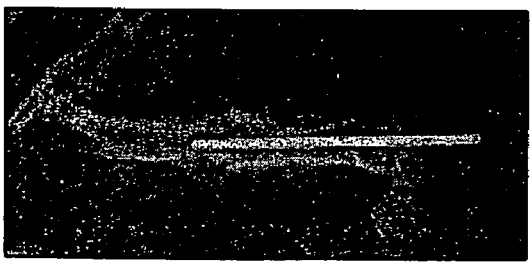
Figure 1D:
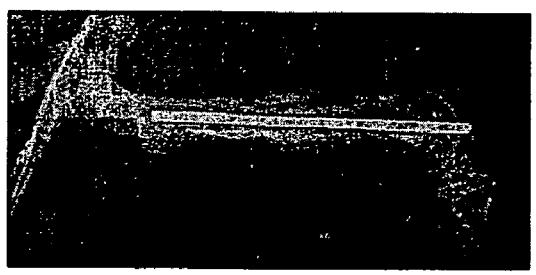
Figure 1E:
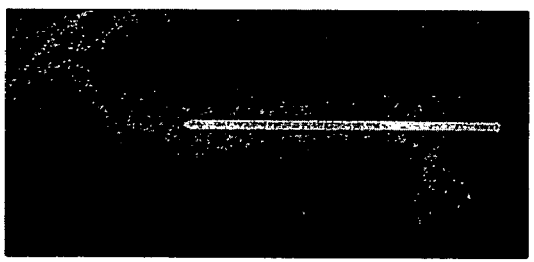
Figure 1F:
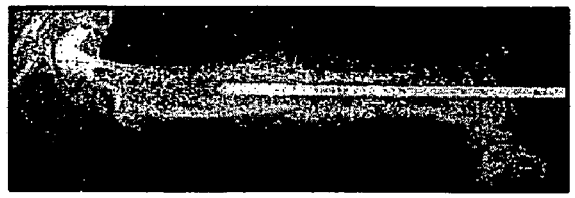
Figure 1G:
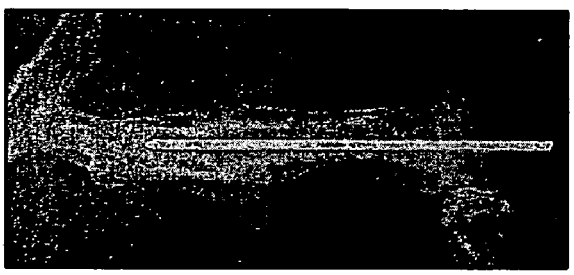

It has been found that inhibition of p38 MAP kinase activity can provide beneficial effects regarding osteogenesis, especially when regarding bone deficits, bone diseases, fractures, grafting, bone resorption, and also beneficial effects in osteogenesis following elective or non-elective bone surgery, especially cosmetic surgery including facial reconstruction, maxillary reconstruction or mandibular reconstruction, osteogenesis following tooth extraction, enhancing long bone extension, enhancing prosthetic ingrowth, and increasing bone synostosis.

The invention is directed to a method of osteogenesis in a patient by administering a pharmaceutically effective amount of a p38 MAP kinase inhibitor to a patient in need of bone healing. By "bone" is intended the dense, semi-rigid, porous, calcified connective tissue forming the major portion of the skeleton of most vertebrates, comprising a dense organic matrix and an inorganic, mineral component. Bone is any of numerous anatomically distinct structures making up the skeleton of a vertebrate. The term "osteogenesis" refers to the net development and net formation of bone, including, without limitation the promotion of new bone growth and/or the alleviation of bone resorption. By "bone healing" is intended restoring a bone and, optionally, the surrounding cartilage to, or to be closer to, their original or intended physical and mechanical properties when compared to such properties possessed by the bone prior to the start of such healing and/or prior to the injury, pathological destruction, pathological deterioration, surgical destruction, or surgical deterioration of the bone.

A "pharmaceutically effective amount" is intended an amount of a compound that, when administered to a mammal for treating a condition, disorder or disease, is sufficient to elicit a cellular response that is clinically significant, without excessive levels of side effects. See, "Formulations and Methods of Administration" section, infra, for further details.

"Mammal" refers to any animal classified as a mammal, including humans, domestic and farm animals, and zoo, sports, and pet companion animals such as a household pet and other domesticated animal such as, but not limited to, cattle, sheep, ferrets, swine, horses, poultry, rabbits, goats, dogs, cats and the like. Preferred companion animals are dogs and cats. Preferably, the mammal is human.

A "patient" is intended a mammal, preferably a human, in need of treatment of a condition, disorder or disease.

In one aspect of bone healing, the invention is directed to a method of treating or increasing the rate of healing of bone fracture in a patient by administering a pharmaceutically effective amount of a p38 MAP kinase inhibitor to a patient in need of treatment or increase in the rate of healing of bone fracture.

The terms "treat" and "treatment" refer to both therapeutic treatment and prophylactic or preventative measures, wherein the object is to prevent or slow down (lessen) an undesired physiological condition, disorder or disease or obtain beneficial or desired clinical results. For purposes of this invention, beneficial or desired clinical results include, but are not limited to, alleviation of symptoms; diminishment of extent of condition, disorder or disease; stabilized (i.e., not worsening) state of condition, disorder or disease; delay or slowing of condition, disorder or disease progression; amelioration of the condition, disorder or disease state, remission (whether partial or total), whether detectable or undetectable; or enhancement or improvement of condition, disorder or disease. Treatment includes eliciting a cellular response that is clinically significant, without excessive levels of side effects. Treatment also includes prolonging survival as compared to expected survival if not receiving treatment.

By "bone fracture" is intended a complete or incomplete break, rupture or crack of a bone. Diagnosis of fractures normally depends upon clinical examination and radiological findings. In the invention, bone fractures include, but are not limited to, traumatic fractures, long-term fractures, and pathological fractures.

"Traumatic fracture" refers to an immediate fracture, which involves a supraliminal trauma with a degree of local violence that exceeds the natural elasticity of the bone. It can be accompanied by simultaneous injury to the soft tissues and very often the skin. A traumatic fracture can be closed (the adjacent soft tissues can be injured but the covering soft parts are largely preserved). A traumatic fracture can also be open (the broken ends of the bone are freed by extensive soft tissue injury so that pathogens from outside can enter the wound directly).

"Long-term fracture" refers to a chronic fracture, fatigue fracture, stress fracture or spontaneous fracture type I.

"Pathological fracture" refers to a spontaneous fracture type II. A pathological fracture arises spontaneously, without adequate trauma to account for it. The bone may have been previously damaged, either by systemic disease (e.g., osteoporosis, osteodystrophy, or Paget's osteitis deformans) or by a local bone lesion (e.g., metastasis, radio-osteonecrosis, or bone tumor). See, Adler, Claus-Peter, BONE DISEASES, p. 114 (Springer-Verlag, Germany 2000).

Fractures also include, but are not limited to, oblique torsion fracture, transverse fracture, comminuted fracture, compression fracture, rib fractures, creeping fracture, and fractured femoral neck (Adler, Claus-Peter, BONE DISEASES, Springer-Verlag, Germany (2000)).

Fracture healing includes primary fracture healing and secondary fracture healing. Primary fracture healing involves (1) internal contact of the bone ends, (2) uninterrupted immobility of the part, and (3) an adequate blood supply. Secondary fracture healing involves local inflammation and development of a callus (Adler, Claus-Peter, BONE DISEASES, Springer-Verlag, Germany (2000)).

The invention is also directed to a method of treating or increasing the rate of bone grafting in a patient by administering a therapeutically effective amount of a p38 MAP kinase inhibitor to a patient in need of treatment or increased rate of bone grafting. By "bone grafting" is intended bone implantation or transplantation by, e.g., autograft, allograft, xenograft, demineralized bone, synthetic and natural bone graft substitutes, such as bioceramics and polymers, and osteoinductive factors. The purposes of bone grafting include, but are not limited to, enhancing healing in, e.g., delayed union or nonunion fractures, to replace areas of bone loss arising from neoplasia excision, osteomyelitis, trauma or cysts, and stimulating bone fusion in arthrodeses.

The invention is directed to a method of increasing bone synostosis in a patient by administering a therapeutically effective amount of a p38 MAP kinase inhibitor to a patient in need thereof. The bone synostosis can be, but is not limited to, a vertebral synostosis.

The invention is also directed to a method of increasing or accelerating osteogenesis, especially following facial reconstruction, maxillary reconstruction, mandibular reconstruction or tooth extraction by administering a p38 MAP kinase inhibitor to a patient in need thereof. The invention is also directed to a method of enhancing long bone extension or enhancing prosthetic ingrowth in a patient by administering a therapeutically effective amount of a p38 MAP kinase inhibitor to a patient in need thereof. The p38 MAP kinase inhibitors can be used in promotion of osteogenesis in plastic surgery, stimulation of bone ingrowth into non-cemented prosthetic joints and dental implants, treatment of periodontal disease and defects, and other tooth repair processes.

The invention is also directed to a method of treating a bone disease in a patient by administering a pharmaceutically effective amount of a p38 MAP kinase inhibitor to a patient in need of treatment of a bone disease. "Bone disease" refers to a disorder or condition relating to abnormality of the bone. Bone diseases that can be treated according to the invention, by increasing bone mass or bone growth include, but are not limited to, osteoporosis, arthritis, osteoarthritis, periodontal disease, alveolar bone loss, osteotomy bone loss, childhood idiopathic bone loss, curvature of the spine, and loss of height. Destructive bone disorders that can be treated according to the invention include, but are not limited to, osteoporosis, osteoarthritis and osteolytic lesions such as those caused by neoplastic disease, radiotherapy, or chemotherapy.

Bone diseases can be caused by a condition which presents with low bone mass, a bone deficit, or a cartilage defect. By "bone mass" is intended bone mass per unit volume. A condition which presents with low bone mass is a condition where the level of bone mass is below the age specific normal level as defined in standards in "Assessment of Fracture Risk and its Application to Screening for Postmenopausal Osteoporosis," Report of a World Health Organization Study Group, World Health Organization Technical Series 843 (1994). A bone deficit is an imbalance in the ratio of bone formation to bone resorption, such that, if unmodified, the subject will exhibit less bone than desirable, or the subject's bones will be less intact and coherent than desired. Bone deficit can also result from fracture, from surgical intervention or from dental or periodontal disease. Bone healing includes, but is not limited to, repair of bone deficits, such as those occurring in, e.g., closed, open and non-union fractures. A cartilage defect is a damaged cartilage, less cartilage than desired, or cartilage that is less intact and coherent than desired. In the present invention, the p38 MAP kinase inhibitors can be used for treating cartilage defects.

Included in conditions which present with low bone mass are, but not limited to, primary and secondary osteoporosis, periodontal disease, alveolar bone loss, osteotomy bone loss, and childhood idiopathic bone loss. Conditions which present with low bone mass also includes, but are not limited to, long term complications of osteoporosis such as curvature of the spine, loss of height and prosthetic surgery.

The p38 MAP kinase inhibitors can be used to elevate peak bone mass in pre-menopausal women, to treat growth deficiencies, increase bone formation during distraction osteogenesis, and treat other skeletal disorders, such as age-related osteoporosis, post-menopausal osteoporosis, glucocorticoid-induced osteoporosis or disuse osteoporosis and arthritis. The p38 MAP kinase inhibitors can also be useful in repair of congenital, trauma-induced or surgical resection of bone (for instance, for cancer treatment), and in cosmetic surgery.

Osteoporosis or porous bone is a disease characterized by net loss of bone mass per unit volume. The consequence of this loss of bone mass and resulting bone fracture is the failure of the skeleton to provide adequate structural support for the body, low bone mass and structural deterioration of bone tissue, leading to bone fragility and an increased susceptibility to fractures of the hip, spine, and wrist. Bone loss occurs without symptoms. Osteoporosis includes "secondary osteoporosis," such as glucocorticoid-induced osteoporosis, hyperthyroidism-induced osteoporosis, immobilization-induced osteoporosis, heparin-induced osteoporosis or immunosuppressive-induced osteoporosis. In people with osteoporosis, the bones can become so weak that a sudden strain can cause a fracture or a vertebra to collapse. Most current osteoporosis treatments stop continued bone loss but do not enhance bone formation and thus bone quality remains poor but does not get worse.

Thus, the invention is also directed to a method of increasing bone mass in a mammal by administering a pharmaceutically effective amount of a p38 MAP kinase inhibitor to a mammal in need of increased bone mass. The invention is also directed to a method of decreasing bone resorption in a patient by administering a pharmaceutically effective amount of a p38 MAP kinase inhibitor to a patient in need of decreased bone resorption, thereby increasing bone mass to offset the decreased bone resorption.

The invention is also directed to a method of increasing or enhancing the rate of bone growth in a mammal by administering a pharmaceutically effective amount of a p38 MAP kinase inhibitor to a mammal in need of increased or enhanced rate of bone growth.

The invention is further directed to a method of decreasing osteoclast differentiation by administering a pharmaceutically effective amount of a p38 MAP kinase inhibitor to a mammal in need of increased osteoclast activity. As is known in the art, osteoclasts differentiation is mediated by p38 MAP kinase activity (Li et al., *Endocrinology* 143:3105 (2002); Lee et al., *Bone* 30(1):71 (2002); Matsumoto et al., *FEBS Lett.* 486:23 (2000); and Matsumoto et al., *J. Biol. Chem.* 275:31155 (2000)).

The invention is also directed to a method of increasing chondrocyte differentiation in a mammal by administering a pharmaceutically effective amount of a p38 MAP kinase inhibitor to a mammal in need of increased chondrocyte differentiation. Chondrocytes are mature cartilage cells embedded in a lacuna within the cartilage matrix. Chondrocytes are formed embryologically through condensation and differentiation of mesenchymal cell precursors. After birth, chondrocytes are present in a variety of cartilaginous tissues. During bone healing, mesenchymal stem cells migrate and/or proliferate at the fracture site and begin to differentiate into chondrocytes. Chondrocytes at the osteoblast-chondrocyte boundary terminally differentiate into hypertrophic chondrocytes, express Type X collagen, secrete angiogenic factors, and mineralize the cartilaginous matrix (calcified cartilage). The p38 kinase inhibitor can promote chondrocyte differentiation either indirectly by promoting proliferation and/or migration of mesenchymal stem cells, or by directly accelerating calcified cartilage formation, which is the end stage of chondrocyte differentiation.

In the invention, the p38 MAP kinase inhibitors can be administered to a mammal to induce differentiation of bone-forming cell precursors. By a "cell precursor" is intended a cell that possesses and retains the capacity for proliferation and differentiation, e.g., mesenchymal cell, preosteoblast, and chondrocyte.

The invention is also directed to a method of increasing or accelerating the rate of calcified cartilage formation in a mammal by administering a pharmaceutically effective amount of a p38 MAP kinase inhibitor to a mammal in need of accelerated calcified cartilage formation.

Veterinary uses of the p38 MAP kinase inhibitors are also contemplated. Such uses would include treatment of bone or cartilage deficits or defects in domestic animals, livestock and thoroughbred horses.

In the methods of the invention, a pharmaceutically effective amount of a p38 MAP kinase inhibitor and estrogen, a selective estrogen receptor modulator, or a bisphosphonate can be administered when appropriate as can be determined by those of skill in the art.

Preferred bisphosphonates include, but are not limited to, tiludronic acid, alendronic acid, zoledronic acid, ibandronic acid, risedronic acid, etidronic acid, clodronic acid, and pamidronic acid and their pharmaceutically acceptable salts. One skilled in the art will know that these compounds are often referred to as their ion form, e.g., tiludronate, alendronate, zoledronate, ibandronate, risedronate, etidronate, clodronate and pamidronate. Especially preferred bisphosphonates include alendronate and risedronate.

Inhibitors of p38 MAP Kinase

As used herein, the term "inhibitor" includes, but is not limited to, any suitable molecule, compound, protein or fragment thereof, nucleic acid, formulation or substance that can regulate p38 MAP kinase activity. The inhibitor can affect a single p38 MAP kinase isoform (p38α, p38β, p3γ, and p38δ), more than one isoform, or all isoforms of p38

MAP kinase. In a preferred embodiment, the inhibitor regulates the a isoform of p38 MAP kinase.

According to the present invention, it is contemplated that the inhibitor can exhibit its regulatory effect upstream or downstream of p38 MAP kinase or on p38 MAP kinase directly. Examples of inhibitor regulated p38 MAP kinase activity include those where the inhibitor can decrease transcription and/or translation of p38 MAP kinase, can decrease or inhibit post-translational modification and/or cellular trafficking of p38 MAP kinase, or can shorten the half-life of p38 MAP kinase. The inhibitor can also reversibly or irreversibly bind p38 MAP kinase, inactivate its enzymatic activity, or otherwise interfere with its interaction with downstream substrates.

If acting on p38 MAP kinase directly, in one embodiment the inhibitor should exhibit an $IC_{50}$ value of about 5 μM or less, preferably 500 nm or less, more preferably 100 nm or less. In a related embodiment, the inhibitor should exhibit an $IC_{50}$ value relative to the p38α MAP kinase isoform that is about ten fold less than that observed when the same inhibitor is tested against other p38 MAP kinase isoforms in a comparable assay.

Those skilled in the art can determine whether or not a compound is useful in the present invention by evaluating its p38 MAP kinase activity as well as its relative $IC_{50}$ value. This evaluation can be accomplished through conventional in vitro assays. In vitro assays include assays that assess inhibition of kinase or ATPase activity of activated p38 MAP kinase. In vitro assays can also assess the ability of the inhibitor to bind p38 MAP kinase or to reduce or block an identified downstream effect of activated p38 MAP kinase, e.g., cytokine secretion. $IC_{50}$ values are calculated using the concentration of inhibitor that causes a 50% decrease as compared to a control.

A binding assay is a fairly inexpensive and simple in vitro assay to run. As previously mentioned, binding of a molecule to p38 MAP kinase, in and of itself, can be inhibitory, due to steric, allosteric or charge-charge interactions. A binding assay can be performed in solution or on a solid phase using p38 MAP kinase or a fragment thereof as a target. By using this as an initial screen, one can evaluate libraries of compounds for potential p38 MAP kinase regulatory activity.

The target in a binding assay can be either free in solution, fixed to a support, or expressed in or on the surface of a cell. A label (e.g., radioactive, fluorescent, quenching, etc.) can be placed on the target, compound, or both to determine the presence or absence of binding. This approach can also be used to conduct a competitive binding assay to assess the inhibition of binding of a target to a natural or artificial substrate or binding partner. In any case, one can measure, either directly or indirectly, the amount of free label versus bound label to determine binding. There are many known variations and adaptations of this approach to minimize interference with binding activity and optimize signal.

For purposes of in vitro cellular assays, the compounds that represent potential inhibitors of p38 MAP kinase function can be administered to a cell in any number of ways. Preferably, the compound or composition can be added to the medium in which the cell is growing, such as tissue culture medium for cells grown in culture. The compound is provided in standard serial dilutions or in an amount determined by analogy to known modulators. Alternatively, the potential inhibitor can be encoded by a nucleic acid that is introduced into the cell wherein the cell produces the potential inhibitor itself.

Alternative assays involving in vitro analysis of potential inhibitors include those where cells (e.g., HeLa) transfected with DNA coding for relevant kinases can be activated with substances such as sorbitol, IL-1, TNF, or PMA. After immunoprecipitation of cell lysates, equal aliquots of immune complexes of the kinases are pre-incubated for an adequate time with a specific concentration of the potential inhibitor followed by addition of kinase substrate buffer mix containing labeled ATP and GST-ATF2 or MBP. After incubation, kinase reactions are terminated by the addition of SDS loading buffer. Phosphorylated substrate is resolved through SDS-PAGE and visualized and quantitated in a phosphorimager. The p38 MAP kinase regulation, in terms of phosphorylation and $IC_{50}$ values, can be determined by quantitation. See e.g., Kumar, S. et al., *Biochem. Biophys. Res. Commun.* 235:533-538 (1997).

Other in vitro assays can also assess the production of TNF-α as a correlation to p38 MAP kinase activity. One such example is a Human Whole Blood Assay. In this assay, venous blood is collected from, e.g., healthy male volunteers into a heparinized syringe and is used within 2 hours of collection. Test compounds are dissolved in 100% DMSO and 1 μl aliquots of drug concentrations ranging from 0 to 1 mM are dispensed into quadruplicate wells of a 24-well microtiter plate (Nunclon Delta SI, Applied Scientific Co., San Francisco, Calif.). Whole blood is added at a volume of 1 ml/well and the mixture is incubated for 15 minutes with constant shaking (Titer Plate Shaker, Lab-Line Instruments, Inc., Melrose Park, Ill.) at a humidified atmosphere of 5% $CO_2$ at 37° C. Whole blood is cultured either undiluted or at a final dilution of 1:10 with RPMI 1640 (Gibco 31800+ $NaHCO_3$, Life Technologies, Rockville, Md. and Scios, Inc., Sunnyvale, Calif.). At the end of the incubation period, 10 μl of LPS (*E. coli* 0111:B4, Sigma Chemical Co., St. Louis, Mo.) is added to each well to a final concentration of 1 or 0.1 μg/ml for undiluted or 1:10 diluted whole blood, respectively. The incubation is continued for an additional 2 hours. The reaction is stopped by placing the microtiter plates in an ice bath, and plasma or cell-free supernates are collected by centrifugation at 3000 rpm for 10 minutes at 4° C. The plasma samples are stored at −80° C. until assayed for TNF-α levels by ELISA, following the directions supplied by Quantikine Human TNF-α assay kit (R&D Systems, Minneapolis, Minn.). $IC_{50}$ values are calculated using the concentration of inhibitor that causes a 50% decrease as compared to a control.

A similar assay is an Enriched Mononuclear Cell Assay. The enriched mononuclear cell assay begins with cryopreserved Human Peripheral Blood Mononuclear Cells (HPBMCs) (Clonetics Corp.) that are rinsed and resuspended in a warm mixture of cell growth media. The resuspended cells are then counted and seeded at $1 \times 10^6$ cells/well in a 24-well microtitre plate. The plates are then placed in an incubator for an hour to allow the cells to settle in each well. After the cells have settled, the media is aspirated and new media containing 100 ng/ml of the cytokine stimulatory factor Lipopolysaccharide (LPS) and a test chemical compound is added to each well of the microtiter plate. Thus, each well contains HPBMCs, LPS and a test chemical compound. The cells are then incubated for 2 hours, and the amount of the cytokine Tumor Necrosis Factor Alpha (TNF-α) is measured using an Enzyme Linked Immunoassay (ELISA). One such ELISA for detecting the levels of TNF-α is commercially available from R&D Systems. The amount of TNF-α production by the HPBMCs in each well is then compared to a control well to determine whether the chemical compound acts as an inhibitor of cytokine production.

Compounds useful in the practice of the present invention include, but are not limited to, compounds of formula:

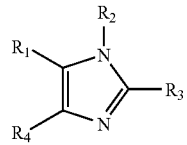

wherein
$R_1$ is a heteroaryl ring selected from 4-pyridyl, pyrimidinyl, quinolyl, isoquinolinyl, quinazolin-4-yl, 1-imidazolyl, 1-benzimidazolyl, 4-pyridazinyl, and a 1,2,4-triazin-5-yl ring, which heteroaryl ring is substituted one to three times with Y, $N(R_{10})C(O)R_b$, a halo-substituted mono- or di-$C_{1-6}$ alkyl-substituted amino, or $NHR_a$ and which ring is further optionally substituted with $C_{1-4}$ alkyl, halogen, hydroxyl, optionally-substituted $C_{1-4}$ alkoxy, optionally-substituted $C_{1-4}$ alkylthio, optionally-substituted $Ca_4$ alkylsulfinyl, $CH_2OR_{12}$, amino, mono- and di-$C_{1-6}$ alkyl-substituted amino, $NHR_a$, $N(R_{10})C(O)R_b$, $N(R_{10})S(O)_2R_d$, or an N-heterocyclyl ring which has from 5 to 7 members and optionally contains an additional heteroatom selected from oxygen, sulfur or $NR_{15}$;
Y is $X_1$—$R_a$;
$X_1$ is oxygen or sulfur;
$R_a$ is $C_{1-6}$ alkyl, aryl, aryl$C_{1-6}$ alkyl, heterocyclic, heterocyclyl$C_{1-6}$ alkyl, heteroaryl, or heteroaryl$C_{1-6}$ alkyl, wherein each of these moieties can be optionally substituted;
$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl;
$R_d$ is $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl;
$R_3$ is hydrogen;
$R_4$ is phenyl, naphth-1-yl, naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, —$C(Z)NR_7R_{17}$, —$C(Z)OR_{16}$, —$(CR_{10}R_{20})_vCOR_{12}$, —$SR_5$, —$SOR_5$, —$OR_{12}$, halo-substituted-$C_{1-4}$ alkyl, $C_{1-4}$ alkyl, —$ZC(Z)R_{12}$, —$NR_{10}C(Z)R_{16}$, or —$(CR_{10}R_{20})_vNR_{10}R_{20}$ and which, for other positions of substitution, is halogen, cyano, —$C(Z)NR_{13}R_{14}$, —$C(Z)OR_3$, —$(CR_{10}R_{20})_{m''}COR_3$, —$S(O)_mR_3$, —$OR_3$, —$OR_{12}$, halo-substituted $C_{1-4}$ alkyl, $C_{1-4}$ alkyl, —$(CR_{10}R_{20})_{m''}NR_{10}C(Z)R_3$ —$NR_{10}S(O)_mR_8$, —$NR_{10}S(O)_mNR_7R_{17}$, -$ZC(Z)R_3$ -$ZC(Z)R_{12}$, or —$CR_{10}R_{20})_{m''}NR_{13}R_{14}$;
$R_f$ is heterocyclyl, heterocyclyl$C_{1-10}$ alkyl or $R_8$;
Z is oxygen or sulfur;
v is 0, 1, or 2;
m is 0, 1, or 2;
m' is 1 or 2;
m'' is 0, 1, 2, 3, 4, or 5;
$R_2$ is $C_{1-10}$ alkyl $N_3$, —$(CR_{10}R_{20})_nOR_9$, heterocylyl, heterocycyl$C_{1-10}$ alkyl, $C_{1-10}$ alkyl halo-substituted $C_{1-10}$ alkyl, $C_{2-10}$ alkenyl, $C_{2-10}$ alkynyl, $C_{3-7}$ cycloalkyl, $C_{3-7}$ cycloalkyl$C_{1-10}$ alkyl, $C_{5-7}$ cycloalkenyl, $C_{5-7}$ cycloalkenyl$C_{1-10}$ alkyl, aryl, aryl$C_{1-10}$ alkyl heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$, $(CR_{10}R_{20})_nNO_2$, $(CR_{10}R_{20})_nCN$, $(CR_{10}R_{20})_nSO_2R_{18}$, $(CR_{10}R_{20})_nS(O)_mNR_{13}R_{14}$, $(CR_{10}R_{20})_nC(Z)R_{11}$, $(CR_{10}R_{20})_nOC(Z)R_{11}$, $(CR_{10}R_{20})_nC(Z)OR_{11}$, $(CR_{10}R_{20})_nC(Z)NR_{13}R_{14}$, $(CR_{10}R_{20})_nC(Z)NR_{11}OR_9$, $(CR_{10}R_{20})_nNR_{10}C(Z)R_{11}$, $(CR_{10}R_{20})_nNR_{10}C(Z)NR_{13}R_{14}$, $(CR_{10}R_{20})_nN(OR_6)C(Z)NR_{13}R_{14}$, $(CR_{10}R_{20})_nN(OR_6)C(Z)R_{11}$, $(CR_{10}R_{20})_nC(=NOR_6)R_{11}$, $(CR_{10}R_{20})_nNR_{10}C(=NR_{19})NR_{13}R_{14}$, $(CR_{10}R_{20})_nOC(Z)NR_{13}R_{14}$, $(CR_{10}R_{20})_nNR_{10}C(Z)NR_{13}R_{14}$, $(CR_{10}R_{20})_nNR_{10}C(Z)OR_{10}$, 5-($R_{18}$)-1,2,4-oxadiazol-3-yl or 4-($R_{12}$)-5-($R_{18}R_{19}$)-4,5-dihydro-1,2,4-oxadiazol-3-yl; wherein the aryl, arylalkyl, heteroaryl, heteroaryl alkyl, cycloalkyl, cycloalkyl alkyl, heterocyclic and heterocyclic alkyl groups can be optionally substituted;
n is an integer having a value of 1 to 10;
n' is 0, or an integer having a value of 1 to 10;
$R_5$ is hydrogen, $C_{1-4}$ alkyl, $C_{2-4}$ alkenyl, $C_{2-4}$ alkynyl or $NR_7R_{17}$, excluding the moieties —$SR_5$ being —$SNR_7R_{17}$ and —$S(O)R_5$ being —$SOH$;
$R_6$ is hydrogen, a pharmaceutically-acceptable cation, $C_{1-10}$ alkyl, $C_{3-7}$ cycloalkyl, aryl, aryl$C_{1-4}$ alkyl, heteroaryl, heteroaryl$C_{1-10}$ alkyl, heterocyclyl, aroyl, or $C_{1-10}$ alkanoyl;
$R_7$ and $R_{17}$ are each independently selected from hydrogen or $C_{1-4}$ alkyl, or $R_7$ and $R_{17}$ together with the nitrogen to which they are attached form a heterocyclic ring of 5 to 7 members which ring optionally contains an additional heteroatom selected from oxygen, sulfur or $NR_{15}$;
$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, or $(CR_{10}R_{20})_n NR_{13}R_{14}$, wherein the aryl, arylalkyl, heteroaryl, and heteroaryl alkyl can be optionally substituted;
$R_9$ is hydrogen, —$C(Z)R_{11}$, optionally-substituted $C_{1-10}$ alkyl, $S(O)_2R_{18}$, optionally-substituted aryl or optionally-substituted aryl$C_{1-4}$ alkyl;
$R_{10}$ and $R_{20}$ are each independently selected from hydrogen or $C_{1-4}$ alkyl;
$R_{11}$ is hydrogen, $C_{1-10}$ alkyl, $C_{3-7}$ cycloalkyl, heterocyclyl, heterocyclyl$C_{1-10}$ alkyl, aryl, aryl$C_{1-10}$ alkyl, heteroaryl or heteroaryl$C_{1-10}$ alkyl;
$R_{12}$ is hydrogen or $R_{16}$;
$R_{13}$ and $R_{14}$ are each independently selected from hydrogen or optionally-substituted $C_{1-4}$ alkyl, optionally-substituted aryl or optionally-substituted aryl$C_{1-4}$ alkyl, or together with the nitrogen to which they are attached form a heterocyclic ring of 5 to 7 members which ring optionally contains an additional heteroatom selected from oxygen, sulfur or $NR_9$;
$R_{15}$ is $R_{10}$ or $C(Z)C_{1-4}$ alkyl;
$R_{16}$ is $C_{1-4}$ alkyl, halo-substituted $C_{1-4}$ alkyl, or $C_{3-7}$ cycloalkyl;
$R_{18}$ is $C_{1-10}$ alkyl, $C_{3-7}$ cycloalkyl, heterocyclyl, aryl, aryl$C_{1-10}$ alkyl, heterocyclyl, heterocyclyl$C_{1-10}$ alkyl, heteroaryl or heteroaryl$C_{1-10}$ alkyl; and
$R_{19}$ is hydrogen, cyano, $C_{1-4}$ alkyl, $C_{3-7}$ cycloalkyl or aryl; or a pharmaceutically-acceptable salt thereof, or wherein
$R_1$, Y, $X_1$, $R_a$, $R_b$, $R_d$, V, m, m', m, Z, n, n', and $R_5$ are defined as above, and $R_2$ is hydrogen, $C_{10}$ alkyl, halo-substituted $C_{1-10}$ alkyl, $C_{2-10}$ alkenyl, $C_{2-10}$ alkynyl, $C_{3-7}$ cycloalkyl, $C_{3-7}$ cycloalkyl$C_{1-10}$ alkyl, $C_{5-7}$ cycloalkenyl, aryl, aryl$C_{1-10}$ alkyl, heteroaryl, heteroaryl$C_{1-10}$ alkyl, heterocyclyl, heterocyclyl$C_{1-10}$ alkyl, $(CR_{10}R_{28})_nOR_{12}$, $(CR_{10}R_{28})_nOR_{13}$, $(CR_{10}R_{28})_nS(O)_mR_{25}$, $(CR_{10}R_{28})_nS(O)_2R_{25}$, $(CR_{10}R_{28})_n$NHS$(O)_2R_{25}$, $(CR_{10}R_{28})_nNR_8R_9$, $(CR_{10}R_{28})_nNO_2$, $(CR_{10}R_{28})_nCN$, $(CR_{10}R_{28})_nS(O)_mNR_8R_9$, $(CR_{10}R_{28})_nC(Z)R_{13}$, $(CR_{10}R_{28})_nC(Z)OR_{13}$, $(CR_{10}R_{28})_nOC(Z)NR_8R_9$, $(CR_1OR_{28})_n$ $C(Z)NR_{13}OR_{12}$, $(CR_{10}R_{28})_nNR_{10}C(Z)R_{13}$, $(CR_{10}R_{28})_nNR_{10}C(Z)NR_8R_9$, $(CR_{10}R_{28})_nN(OR_{21})C(Z)NR_8R_9$, $(CR_{10}R_{28})_nN(OR_{21})C(Z)R_{13}$, $(CR_{10}R_{28})_nC(=NOR_{21})R_{13}$, $(CR_{10}R_{28})_nNR_{10}C(=NR_{27})NR_8R_9$, $(CR_{10}R_{28})_nOC(Z)NR_8R_9$, $(CR_{10}R_{28})_nNR_{10}C(Z)OR_{10}$, $(CR_{10}R_{28})_nNR_{10}C(Z)OR_{10}$, 5-$(R_{25})$-1,2,4-oxadiazol-3-yl or 4-$(R_{12})$-5-$(R_{18}R_{19})$-4,5-dihydro-1,2,4-oxadiazol-3-yl; wherein the cycloalkyl, cycloalkyl alkyl, aryl, arylalkyl, heteroaryl, heteroarylalkyl, heterocyclyl, or heterocyclylalkyl moieties can be optionally substituted;

$R_3$ is hydrogen or Q-$(Y_1)_t$;

Q is an aryl or heteroaryl group;

t is 1, 2, or 3;

$Y_1$ is independently selected from hydrogen, $C_{1-5}$ alkyl, halo-substituted $C_{1-5}$ alkyl, halogen, or —$(CR_{10}R_{20})_nY_2$;

$Y_2$ is $OR_8$, $NO_2$, $S(O)_{m'}R_{11}$, $SR_8$, $S(O)_{m'}OR_8$, $S(O)_mNR_8R_9$, $N$ $C(O)R_8$, $CO_2R_8$, $CO_2(CR_{10}R_{20})_nCONR_8R_9$, CN, ZC(O)$R_8$, $C(Z)NR_8R_9$, $NR_{10}C(Z)R_8$, $C(Z)NR_8OR_9$, $NR_{10}C(Z)NR_8R_9$, $NR_{10}S(O)_mR_{11}$, $N(OR_{21})C(Z)NR_8R_9$, $N(OR_{21})C(Z)R_8$, $C(=NOR_{21})R_8$, $NR_{10}C(=NR_{15})SR_{11}$, $NR_{10}C(=NR_{15})NR_8R_9$, $NR_{10}C(=CR_{14}R_{24})SR_{11}$, $NR_{10}C(=CR_{14}R_{24})NR_8R_9$, $NR_{10}C(O)C(O)NR_8R_9$, $NR_{10}C(O)C(O)OR_{10}$, $C(=NR_{13})NR_8R_9$, $C(=NOR_{13})NR_8R_9$, $C(=NR_{13})ZR_{11}$, $OC(Z)NR_8R_9$, $NR_{10}S(O)_{m'}CF_3$, $NR_{10}C(Z)OR_{10}$, 5-$(R_{18})$-1,2,4-oxadiazol-3-yl or 4-$(R_{12})$-5-$(R_{18}R_{19})$-4,5-dihydro-1,2,4-oxadiazol-3-yl;

$R_4$ is phenyl, naphth-1-yl or naphth-2-yl which is optionally substituted by one or two substituents, each of which is independently selected, and which, for a 4-phenyl, 4-naphth-1-yl or 5-naphth-2-yl substituent, is halo, nitro, cyano, $C(Z)NR_7R_{17}$, $C(Z)OR_{23}$, $(CR_{10}R_{20})_vCOR_{36}$, $SR_5$, $SOR_5$, $OR_{36}$, halo-substituted-$C_{1-4}$ alkyl, $C_{1-4}$ alkyl, $ZC(Z)R_{36}$, $NR_{10}C(Z)R_{23}$, or $(CR_{10}R_{20})_vNR_{10}R_{20}$ and which, for other positions of substitution, is halo, nitro, cyano, $C(Z)NR_{16}R_{26}$, $C(Z)OR_8$, $(CR_{10}R_{20})_{m'}COR_8$, $S(O)_mR_8$, $OR_8$, halo-substituted -$C_{1-4}$ alkyl, $C_{1-4}$ alkyl, $(CR_{10}R_{20})_{m'}NR_{10}C(Z)R_8$, $NR_{10}S(O)_{m'}R_{11}$, $NR_{10}S(O)_mNR_7R_{17}$, $ZC(Z)R_8$ or $(CR_{10}R_{20})_m NR_{16}R_{26}$;

$R_7$ and $R_{17}$ are each independently selected from hydrogen or $C_{1-4}$ alkyl, or $R_7$ and $R_{17}$ together with the nitrogen to which they are attached form a heterocyclic ring of 5 to 7 members, which ring optionally contains an additional heteroatom selected from oxygen, sulfur or $NR_{22}$;

$R_8$ is hydrogen, heterocyclyl, heterocyclylalkyl or $R_{11}$;

$R_9$ is hydrogen, $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl, heteroaryl or heteroarylalkyl, or $R_8$ and $R_9$ can together with the nitrogen to which they are attached form a heterocyclic ring of 5 to 7 members, which ring optionally contains an additional heteroatom selected from oxygen, sulfur or $NR_{12}$;

$R_{10}$ and $R_{20}$ are each independently selected from hydrogen or $C_{1-4}$ alkyl;

$R_{11}$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl, heteroaryl or heteroarylalkyl;

$R_{12}$ is hydrogen, —C(Z)$R_{13}$ or optionally-substituted $C_{1-4}$ alkyl, optionally-substituted aryl, optionally-substituted aryl$C_{1-4}$ alkyl, or S(O)$_2R_{25}$;

$R_{13}$ is hydrogen, $C_{1-10}$ alkyl, $C_{3-7}$ cycloalkyl, heterocyclyl, heterocyclyl$C_{1-10}$ alkyl, aryl, aryl$C_{1-10}$ alkyl, heteroaryl or heteroaryl $C_{1-10}$ alkyl, wherein all of these moieties can be optionally substituted;

$R_{14}$ and $R_{24}$ are each independently selected from hydrogen, alkyl, nitro or cyano;

$R_{15}$ is hydrogen, cyano, $C_{1-4}$ alkyl, $C_{3-7}$ cycloalkyl or aryl;

$R_{16}$ and $R_{26}$ are each independently selected from hydrogen or optionally-substituted $C_{1-4}$ alkyl, optionally-substituted aryl or optionally-substituted aryl$C_{1-4}$ alkyl, or together with the nitrogen to which they are attached form a heterocyclic ring of 5 to 7 members, which ring optionally contains an additional heteroatom selected from oxygen, sulfur or $NR_{12}$;

$R_{18}$ and $R_{19}$ are each independently selected from hydrogen, $C_{1-4}$ alkyl, substituted alkyl, optionally-substituted aryl, optionally-substituted arylalkyl, or together denote an oxygen or sulfur;

$R_{21}$ is hydrogen, a pharmaceutically-acceptable cation, $C_{1-10}$ alkyl, $C_{3-7}$ cycloalkyl, aryl, aryl$C_{1-4}$ alkyl, heteroaryl, heteroarylalkyl, heterocyclyl, aroyl, or $C_{1-10}$ alkanoyl;

$R_{22}$ is $R_{10}$ or C(Z)-$C_{1-4}$ alkyl;

$R_{23}$ is $C_{1-4}$ alkyl, halo-substituted-$C_{1-4}$ alkyl, or $C_{3-5}$ cycloalkyl;

$R_{25}$ is $C_{1-10}$ alkyl, $C_{3-7}$ cycloalkyl, heterocyclyl, aryl, arylalkyl, heterocyclyl, heterocyclyl$C_{1-10}$ alkyl, heteroaryl or heteroarylalkyl;

$R_{27}$ is hydrogen, cyano, $C_{1-4}$ alkyl, $C_{3-7}$ cycloalkyl, or aryl;

$R_{28}$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl moiety, all of which can be optionally substituted; and $R_{36}$ is hydrogen or $R_{23}$;

or a pharmaceutically acceptable salt thereof.

Exemplary compounds of this formula include:

1-[3-(4-morpholinyl)propyl]-4-(4-fluorophenyl)-5-(4-pyridyl)imidazole;

1-(3-chloropropyl)-4-(4-fluorophenyl)-5-(4-pyridyl)imidazole;

1-(3-azidopropyl)-4-(4-fluorophenyl)-5-(4-pyridyl)imidazole;

1-(3-aminopropyl)-4-(4-fluorophenyl)-5-(4-pyridyl)imidazole;

1-(3-methylsulfonamidopropyl)-4-(4-fluorophenyl)-5-(4-pyridyl)imidazole;

1-[3-(N-phenylmethyl)aminopropyl]-4-(4-fluorophenyl)-5-(4-pyridyl)imidazole;

1-[3-(N-phenylmethyl-N-methyl)aminopropyl]-4-(4-fluorophenyl)-5-(4-pyridyl)imidazole;

1-[3-(1-pyrrolidinyl)propyl]-4-(4-fluorophenyl)-5-(4-pyridyl)imidazole;

1-(3-diethylaminopropyl)-4-(4-fluorophenyl)-5-(4-pyridyl)imidazole;

1-[3-(1-piperidinyl)propyl]-4-(4-fluorophenyl)-5-(4-pyridyl)imidazole;

1-[3-(methylthio)propyl]-4-(4-fluorophenyl)-5-(4-pyridyl)imidazole;
1-[2-(4-morpholinyl)ethyl]-4-(4-fluorophenyl)-5-(4-pyridyl)imidazole;
1-[3-(4-morpholinyl)propyl]-4-(3-methylthiophenyl)-5-(4-pyridyl)imidazole;
(+/−)-1-[3-(4-morpholinyl)propyl]-4-(3-methylsulfinylphenyl)-5-(4-pyridyl)imidazole;
1-[3-(N-methyl-N-benzyl)aminopropyl]-4-(3-methylthiophenyl)-5-(4-pyridyl)imidazole;
1-[3-(N-methyl-N-benzyl)aminopropyl]-4-(3-methylsulfinylphenyl)-5-(4-pyridyl)imidazole;
1-[4-(methylthio)phenyl]-4-(4-fluorophenyl)-5-(4-pyridyl)imidazole;
1-[4-(methylsulfinyl)phenyl]-4-(4-fluorophenyl)-5-(4-pyridyl)imidazole;
1-[3-(methylthio)phenyl]-4-(4-fluorophenyl)-5-(4-pyridyl)imidazole;
(+/−)-1-[3-(methylsulfinyl)phenyl]-4-(4-fluorophenyl)-5-(4-pyridyl)imidazole;
1-[2-(methylthio)phenyl]-4-(4-fluorophenyl)-5-(4-pyridyl)imidazole;
1-[2-(methylsulfinyl)phenyl]-4-(4-fluorophenyl)-5-(4-pyridyl)imidazole;
1-[4-(4-morpholinyl)butyl]-4-(4-fluorophenyl)-5-(4-pyridyl)imidazole;
1-cyclopropyl-4-(4-fluorophenyl)-5-(4-pyridyl)imidazole;
1-isopropyl-4-(4-fluorophenyl)-5-(4-pyridyl)imidazole;
1-cyclopropylmethyl-4-(4-fluorophenyl)-5-(4-pyridyl)imidazole;
1-tert-butyl-4-(4-fluorophenyl)-5-(4-pyridyl)imidazole;
1-(2,2-diethoxyethyl)-4-(4-fluorophenyl)-5-(4-pyridyl)imidazole;
1-formylmethyl-4-(4-fluorophenyl)-5-(4-pyridyl)imidazole;
1-hydroxyiminylmethyl-4-(4-fluorophenyl)-5-(4-pyridyl)imidazole;
1-cyanomethyl-4-(4-fluorophenyl)-5-(4-pyridyl)imidazole;
1-[3-(4-morpholinyl)propyl)-4-(4-fluorophenyl)-5-(2-methylpyrid-4-yl)imidazole;
4-(4-fluorophenyl)-1-[3-(4-morpholinyl)propyl]-5-(2-chloropyridin-4-yl)imidazole;
4-(4-fluorophenyl)-1-[3-(4-morpholinyl)propyl]-5-(2-amino-4-pyridinyl)imidazole;
1-(4-carboxymethyl)propyl-4-(4-fluorophenyl)-5-(4-pyridyl)imidazole;
1-(4-carboxypropyl)-4-(4-fluorophenyl)-5-(4-pyridyl)imidazole;
1-(3-carboxymethyl)ethyl-4-(4-fluorophenyl)-5-(4-pyridyl)imidazole;
1-(3-carboxy)ethyl-4-(4-fluorophenyl)-5-(4-pyridyl)imidazole;
1-(1-benzylpiperidin-4-yl)-4-(4-fluorophenyl)-5-(4-pyridyl)imidazole;
5-(2-aminopyrimidin-4-yl)-4-(4-fluorophenyl)-1-[3-(4-morpholinyl)propyl]imidazole;
5-(2-aminopyrimidin-4-yl)-4-(4-fluorophenyl)-1-(1-benzylpiperidin-4-yl)imidazole;
5-(2-aminopyrimidin-4-yl)-4-(4-fluorophenyl)-1-(2-propyl)imidazole;
5-(2-aminopyrimidin-4-yl)-4-(4-fluorophenyl)-1-(cyclopropylmethyl)imidazole;
5-(2-aminopyrimidin-4-yl)-4-(4-fluorophenyl)-1-(1-carboxyethyl-4-piperidinyl)imidazole;
5-(2-aminopyrimidin-4-yl)-4-(4-fluorophenyl)-1-(4-piperidinyl)imidazole;
1-methyl-4-phenyl-5-(4-pyridyl)imidazole;
1-methyl-4-[3-(chlorophenyl)]-5-(4-pyridinyl)imidazole;
1-methyl-4-(3-methylthiophenyl)-5-(4-pyridyl)imidazole;
(+/−)-1-methyl-4-(3-methylsulfinylphenyl)-5-(4-pyridyl)imidazole;
(+/−)-4-(4-fluorophenyl)-1-[3-(methylsulfinyl)propyl]-5-(4-pyridinyl)imidazole;
4-(4-fluorophenyl)-1-[(3-methylsulfonyl)propyl]-5-(4-pyridinyl)imidazole;
1-(3-phenoxypropyl)-4-(4-fluorophenyl)-5-(4-pyridinyl)imidazole;
1-[3-(phenylthio)propyl]-4-(4-fluorophenyl)-5-(4-pyridinyl)imidazole;
1-[3-(4-morpholinyl)propyl]-4-(4-fluorophenyl)-5-(4-quinolyl)imidazole;
(+/−)-1-(3-phenylsulfinylpropyl)-4-(4-fluorophenyl)-5-(4-pyridinyl)imidazole;
1-(3-ethoxypropyl)-4-(4-fluorophenyl)-5-(4-pyridinyl)imidazole;
1-(3-phenylsulfonylpropyl)-4-(4-fluorophenyl)-5-(4-pyridinyl)imidazole;
1-[3-(4-morpholinyl)propyl]-4-(3-chlorophenyl)-5-(4-pyridyl)imidazole;
1-[3-(4-morpholinyl)propyl]-4-(3,4-dichlorophenyl)-5-(4-pyridyl)imidazole;
4-[4-(4-fluorophenyl)-1-[3-(4-morpholinyl)propyl]-5-(pyrimid-2-one-4-yl) imidazole;
4-(4-fluorophenyl)-5-[2-(methylthio)-4-pyrimidinyl]-1-[3-(4-morpholinyl)propyl]imidazole;
(+/−)-4-(4-fluorophenyl)-5-[2-(methylsulfinyl)-4-pyrimidinyl]-1-[3-(4-morpholinyl)propyl]imidazole;
(E)-1-(1-propenyl)-4-(4-fluorophenyl)-5-(4-pyridinyl)imidazole;
1-(2-propenyl)-4-(4-fluorophenyl)-5-(4-pyridinyl)imidazole;
5-[(2-N,N-dimethylamino)pyrimidin-4-yl]-4-(4-fluorophenyl)-1-[3-(4-morpholinyl)propyl]imidazole;
1-[3-(4-morpholinyl)propyl]-5-(4-pyridinyl)-4-[4-(trifluoromethyl)phenyl]imidazole;
1-[3-(4-morpholinyl)propyl]-5-(4-pyridinyl)-4-[3-(trifluoromethyl)phenyl]imidazole;
1-(cyclopropylmethyl)-4-(3,4-dichlorophenyl)-5-(4-pyridinyl)imidazole;
1-(cyclopropylmethyl)-4-(3-trifluoromethylphenyl)-5-(4-pyridinyl)imidazole;
1-(cyclopropylmethyl)-4-(4-fluorophenyl)-5-(2-methylpyrid-4-yl)imidazole;
1-[3-(4-morpholinyl)propyl]-5-(4-pyridinyl)-4-(3,5-bis-trifluoromethylphenyl)imidazole;
5-[4-(2-aminopyrimidinyl)]-4-(4-fluorophenyl)-1-(2-carboxy-2,2-dimethylethyl)imidazole;
1-(1-formyl-4-piperidinyl)-4-(4-fluorophenyl)-5-(4-pyridinyl)imidazole;
5-(2-amino-4-pyrimidinyl)-4-(4-fluorophenyl)-1-(1-methyl-4-piperidinyl)imidazole;
1-(2,2-dimethyl-3-morpholin-4-yl)propyl-4-(4-fluorophenyl)-5-(2-amino-4-pyrimidinyl)imidazole;
4-(4-fluorophenyl)-5-(4-pyridyl)-1-(2-acetoxyethyl)imidazole;
5-(2-aminopyrimidin-4-yl)-4-(4-fluorophenyl)-1-(1-benzylpyrrolin-3-yl)imidazole;
5-(2-aminopyrimidin-4-yl)-4-(4-fluorophenyl)-1-(2,2,6,6-tetramethylpiperidin-4-yl)imidazole;

5-[4-(2-N-methylamino)pyrimidinyl]-4-(4-fluorophenyl)-1-(4-N-methylpiperidine)imidazole;
5-[4-(2-N-methylamino)pyrimidinyl]-4-(4-fluorophenyl)-1-(4-N-morpholino-1-propyl)imidazole;
5-[4-(2-N-methylamino)pyrimidinyl)-4-(4-fluorophenyl)-1-(4-piperidine)imidazole;
5-[(2-ethylamino)pyrimidin-4-yl]-4-(4-fluorophenyl)-1-(1-methylpiperidin-4-yl)imidazole;
4-(4-fluorophenyl)-5-[2-(isopropyl)aminopyrimidin-4-yl]-1-(1-methylpiperidin-4-yl)imidazole;
5-(2-acetamido-4-pyrimidinyl)-4-(4-fluorophenyl)-1-(4-N-morpholino-1-propyl)imidazole;
5-(2-acetamido-4-pyrimidinyl)-4-(4-fluorophenyl)-1-(1-methyl-4-piperidinyl)imidazole;
5-[4-(2-N-methylthio)pyrimidinyl]-4-(4-fluorophenyl)-1-(4-piperidine)imidazole;
4-(fluorophenyl)-1-(methyl-4-piperidinyl)-5-(2-methylthio-4-pyrimidinyl)imidazole;
4-(fluorophenyl)-1-(methyl-4-piperidinyl)-5-(2-methysulfinyl-4-pyrimidinyl)imidazole;
1-tert-butyl-4-(4-fluorophenyl)-5-(2-methysulfinyl-4-pyrimidinyl)imidazole;
5-[4-(2-aminopyrimidinyl)]-4-(4-fluorophenyl)-1-(2,2,6,6-tetramethyl-4-piperidinyl)imidazole;
5-[4-(2-N-methylamino-4-pyrimidinyl)]-4-(4-fluorophenyl)-1-(2,2,6,6-tetramethyl-4-piperidine)imidazole;
5-(2-amino-4-pyrimidinyl)-4-(4-fluorophenyl)-1-(tetrahydro-4-thiopyranyl)imidazole;
5-(2-amino-4-pyrimidinyl)-4-(4-fluorophenyl)-1-(tetrahydro-4-pyranyl)imidazole;
5-(2-methylamino-4-pyrimidinyl)-4-(4-fluorophenyl)-1-(2-cyanoethyl)imidazole;
5-(2-amino-4-pyrimidinyl)-4-(4-fluorophenyl)-1-(tetrahydro-4-sulfinylpyranyl)imidazole;
5-(2-amino-4-pyrimidinyl)-4-(4-fluorophenyl)-1-(tetrahydro-4-sulfonylpyranyl)imidazole;
5-(2-methylamino-4-pyrimidinyl)-4-(4-fluorophenyl)-1-(2,2,2-trifluoroethyl-4-piperidinyl)imidazole;
5-(2-amino-4-pyrimidinyl)-4-(4-fluorophenyl)-1-(trifluoroacetyl-4-piperidinyl)imidazole;
5-(4-pyridyl)-4-(4-fluorophenyl)-1-(4-piperidinyl)imidazole;
5-(4-pyridyl)-4-(4-fluorophenyl)-1-(1-t-butoxycarbonyl-4-piperidinyl)imidazole;
5-(2-amino-4-pyrimidinyl)-4-(4-fluorophenyl)-1-(4-(1,3-dioxycyclopentyl)cyclohexyl) imidazole;
5-(2-amino-4-pyrimidinyl)-4-(4-fluorophenyl)-1-(4-ketocyclohexyl)imidazole;
5-(2-amino-4-pyrimidinyl)-4-(4-fluorophenyl)-1-(4-cyclohexyl oxime) imidazole;
5-(2-amino-4-pyrimidinyl)-4-(4-fluorophenyl)-1-(4-cyclohexyl hydroxylamine) imidazole;
5-(2-amino-4-pyrimidinyl)-4-(4-fluorophenyl)-1-(trans-4-hydroxyurea) imidazole;
5-(2-amino-4-pyrimidinyl)-4-(4-fluorophenyl)-1-(cis-4-hydroxyurea) imidazole;
5-(2-amino-4-pyrimidinyl)-4-(4-fluorophenyl)-1-(4-hydroxycyclohexyl)imidazole;
5-[4-(2-N-methylamino)pyrimidinyl]-4-(4-fluorophenyl)-1-(4-ketocyclohexyl)imidazole;
5-[4-(2-N-methylamino)pyrimidinyl]-4-(4-fluorophenyl)-1-(trans-4-hydroxycyclohexyl)imidazole;
5-[4-(2-N-methylamino)pyrimidinyl]-4-(4-fluorophenyl)-1-(cis-4-hydroxycyclohexyl)imidazole;
5-[4-(2-N-methylamino)pyrimidinyl]-4-(4-fluorophenyl)-1-[4-(cis-pyrrolidinyl)cyclohexyl] imidazole;
5-[4-(2-N-methylamino)pyrimidinyl]-4-(4-fluorophenyl)-1-[4-(trans-1-pyrrolidinyl)cyclohexyl]imidazole;
5-[4-(2-N-methylamino)pyrimidinyl]-4-(4-fluorophenyl)-1-(4-ethynyl-4-hydroxycyclohexyl)imidazole;
5-[4-(2-N-methylamino)pyrimidinyl]-4-(4-fluorophenyl)-1-(4-(1-propynyl)-4-hydroxycyclohexyl)imidazole;
5-[4-(2-N-methylamino)pyrimidinyl]-4-(4-fluorophenyl)-1-(4-amino-4-methylcyclohexyl)imidazole;
5-[4-(2-N-methylamino)pyrimidinyl]-4-(4-fluorophenyl)-1-(4-acetamido-4-methylcyclohexyl)imidazole;
5-[4-(2-N-methylamino)pyrimidinyl]-4-(4-fluorophenyl)-1-(4-hydroxy-4-methylcyclohexyl)imidazole;
5-[4-(2-N-methylamino)pyrimidinyl]-4-(4-fluorophenyl)-1-(4-oxiranylcyclohexyl)imidazole;
5-[4-(2-N-methylamino)pyrimidinyl]-4-(4-fluorophenyl)-1-(4-cyanomethyl-4-hydroxycyclohexyl)imidazole;
5-[4-(2-N-methylamino)pyrimidinyl]-4-(4-fluorophenyl)-1-(4-hydroxy-4-hydroxymethylcyclohexyl)imidazole;
5-[4-(2-amino)pyrimidinyl]-4-(4-fluorophenyl)-1-[4-hydroxy-4-(1-propynyl)-cyclohexyl]imidazole;
5-[4-(2-amino)pyrimidinyl]-4-(4-fluorophenyl)-1-(4-hydroxy-4-methylcyclohexyl)imidazole;
5-[4-(2-N-methylamino)pyrimidinyl]-4-(4-fluorophenyl)-1-(4-hydroxy-4-isopropyl-cyclohexyl)imidazole;
5-[4-(2-N-methylamino)pyrimidinyl]-4-(4-fluorophenyl)-1-(4-hydroxy-4-phenyl-cyclohexyl)imidazole;
5-[4-(2-N-methylamino)pyrimidinyl]-4-(4-fluorophenyl)-1-(4-hydroxy-4-benzyl-cyclohexyl)imidazole;
5-[4-(2-N-methylamino)pyrimidinyl]-4-(4-fluorophenyl)-1-(4-hydroxy-4-cyanomethyl cyclohexyl)imidazole;
5-[4-(2-N-methylamino)pyrimidinyl]-4-(4-fluorophenyl)-1-(4-hydroxy-4-(2-cyanoethyl)cyclohexyl)imidazole;
5-[4-(2-N-methylamino)pyrimidinyl]-4-(4-fluorophenyl)-1-(4-hydroxy-4-(2-aminoethyl)cyclohexyl)imidazole;
5-[4-(2-N-methylamino)pyrimidinyl]-4-(4-fluorophenyl)-1-(4-hydroxy-4-(2-nitroethyl)-cyclohexyl)imidazole;
5-[4-(2-N-methylamino)pyrimidinyl]-4-(4-fluorophenyl)-1-(4-hydroxymethyl-4-aminocyclohexyl)imidazole;
5-[4-(2-N-methylamino)pyrimidinyl]-4-(4-fluorophenyl)-1-(4-hydroxy-4-aminocyclohexyl)imidazole;
5-[4-(2-N-methylamino)pyrimidinyl]-4-(4-fluorophenyl)-1-(4-aminocyclohexyl)imidazole;
5-[4-(2-N-methylamino)pyrimidinyl]-4-(4-fluorophenyl)-1-(4-hydroxy-4-thiomethyl cyclohexyl)imidazole;
5-[4-(2-N-methylamino)pyrimidinyl]-4-(4-fluorophenyl)-1-(4-hydroxy-4-hydroxy methylcyclohexyl)imidazole;
5-[4-(2-N-methylamino)pyrimidinyl]-4-(4-fluorophenyl)-1-(4-hydroxy-4-aminomethylcyclohexyl)imidazole;
5-[4-(2-amino)pyrimidinyl]-4-(4-fluorophenyl)-1-(4-amino-4-methylcyclohexyl)imidazole;
5-[4-(2-amino)pyrimidinyl]-4-(4-fluorophenyl)-1-(4-hydroxy-4-methylcyclohexyl)imidazole;
5-[4-(2-amino)pyrimidinyl]-4-(4-fluorophenyl)-1-(4-oxiranylcyclohexyl)imidazole;
4-(fluorophenyl)-1-(methyl-4-piperidinyl)-5-(2-methysulfinyl-4-pyrimidinyl)imidazole;

4-(fluorophenyl)-1-(methyl-4-piperidinyl)-5-(2-methylthio-4-pyrimidinyl)imidazole;
5-[(2-benzylamino)pyrimidin-4-yl]-4-(4-fluorophenyl)-1-(1-methylpiperidin-4-yl)imidazole;
4-(4-fluorophenyl)-1-(1-methylpiperidin-4-yl)-5-[2-(4-tetrahydrothiopyranyl)aminopyrimidin-4-yl]imidazole;
4-(4-fluorophenyl)-5-[(2-hydroxy)ethylamino]pyrimidin-4-yl-1-(1-methylpiperidin-4-yl)imidazole;
5-[(2-(3-chlorobenzylamino)pyrimidin-4-yl]-4-(4-fluorophenyl)-1-(1-methylpiperidin-4-yl)imidazole;
5-[(2-(1-naphthylmethylamino)pyrimidin-4-yl]-4-(4-fluorophenyl)-1-(1-methylpiperidin-4-yl)imidazole;
5-[(2-(1-benzyl-4-piperidinylamino)pyrimidin-4-yl]-4-(4-fluorophenyl)-1-(1-methylpiperidin-4-yl)imidazole;
4-(4-fluorophenyl)-1-(1-methylpiperidin-4-yl)-5-[2-[3-(morpholino)propyl]aminopyrimidin-4-yl]imidazole;
5-[2-[(3-bromophenyl)amino]pyrimidin-4-yl]-4-(4-fluorophenyl)-1-(1-methylpiperidin-4-yl)imidazole;
5-[(2-(piperonylamino)pyrimidin-4-yl]-4-(4-fluorophenyl)-1-(1-methylpiperidin-4-yl)imidazole;
5-[(2-(4-piperidinylamino)pyrimidin-4-yl]-4-(4-fluorophenyl)-1-(1-methylpiperidin-4-yl)imidazole;
5-[(2-(5-chlorotryptamino)pyrimidin-4-yl]-4-(4-fluorophenyl)-1-(1-methylpiperidin-4-yl)imidazole;
5-[(2-(2,2,6,6-tetramethylpiperidin-4-yl)aminopyrimidin-4-yl]-4-(4-fluorophenyl)-1-(1-methylpiperidin-4-yl)imidazole;
5-[(2-[1-ethoxycarbonyl)piperidin-4-yl]aminopyrimidin-4-yl]-4-(4-fluorophenyl)-1-(1-methylpiperidin-4-yl)imidazole;
1-(4-oxocyclohexyl)-4-(4-fluorophenyl)-5-[(2-methoxy)pyrimidin-4-yl]imidazole;
cis-1-(4-hydroxycyclohexyl)-4-(4-fluorophenyl)-5-[(2-methoxy)pyrimidin-4-yl]imidazole;
trans-1-(4-hydroxycyclohexyl)-4-(4-fluorophenyl)-5-[(2-methoxy)pyrimidin-4-yl]imidazole;
1-(4-oxocyclohexyl)-4-(4-fluorophenyl)-5-[(2-methylthio)pyrimidin-4-yl]imidazole;
trans-1-(4-hydroxycyclohexyl)-4-(4-fluorophenyl)-5-[(2methylthio)pyrimidin-4-yl]imidazole;
1-(4-oxocyclohexyl)-4-(4-fluorophenyl)-5-[(2-hydroxy)pyrimidin-4-yl]imidazole;
1-(4-oxocyclohexyl)-4-(4-fluorophenyl)-5-[(2-isopropoxy)pyrimidin-4-yl]imidazole;
1-(4-hydroxycyclohexyl)-4-(4-fluorophenyl)-5-[(2-isopropoxy)pyrimidin-4-yl]imidazole;
trans-1-(4-hydroxy-4-methylcyclohexyl)-4-(4-fluorophenyl)-5-[(2-methoxy)pyrimidin-4-yl]imidazole;
cis-1-(4-hydroxy-4-methylcyclohexyl)-4-(4-fluorophenyl)-5-[(2-methoxy)pyrimidin-4-yl]imidazole;
trans-1-(4-hydroxycyclohexyl)-4-(4-fluorophenyl)-5-[(2-ethoxy)pyrimidin-4-yl]imidazole;
1-(4-piperidinyl)-4-(4-fluorophenyl)-5-(2-phenoxypyrimidin-4-yl)imidazole;
1-(4-piperidinyl)-4-(4-fluorophenyl)-5-(2-phenoxy-4-pyridinyl)imidazole;
1-(4-piperidinyl)-4-(4-fluorophenyl)-5-[2-(4-methoxyphenoxy)-4-pyridinyl]imidazole;
1-(4-piperidinyl)-4-(4-fluorophenyl)-5-[2-(4-fluorophenoxy)-4-pyridinyl]imidazole;
1-(piperidin-4-yl)-4-(4-fluorophenyl)-5-[2-(4-methoxyphenoxy)pyrimidin-4-yl]imidazole;
1-(piperidin-4-yl)-4-(4-fluorophenyl)-5-[2-(4-fluorophenoxy)pyrimidin-4-yl]imidazole;
1-(piperidin-4-yl)-4-(4-fluorophenyl)-5-[2-(4-aminocarbonylphenoxy)pyrimidin-4-yl]imidazole;
1-(piperidin-4-yl)-4-(4-fluorophenyl)-5-[2-(4-ethylphenoxy)pyrimidin-4-yl]imidazole;
1-(piperidin-4-yl)-4-(4-fluorophenyl)-5-[2-(4-benzyloxyphenoxy)pyrimidin-4-yl]imidazole;
1-(piperidin-4-yl)-4-(4-fluorophenyl)-5-[2-(4-cyanophenoxy)pyrimidin-4-yl]imidazole;
1-(piperidin-4-yl)-4-(4-fluorophenyl)-5-[2-(4-hydroxyphenoxy)pyrimidin-4-yl]imidazole;
1-(4-hydroxycyclohexyl)-4-(4-fluorophenyl)-5-[2-(phenoxy)pyrimidin-4-yl]imidazole;
1-(piperidin-4-yl)-4-(4-fluorophenyl)-5-[2-(2,6-dimethylphenoxy)pyridin-4-yl]imidazole;
1-(piperidin-4-yl)-4-(4-fluorophenyl)-5-[2-(4-methylphenoxy)pyridin-4-yl]imidazole;
1-(piperidin-4-yl)-4-(4-fluorophenyl)-5-[2-(4-chlorophenoxy)pyridin-4-yl]imidazole;
1-[3-(N-morpholino)propyl]-4-(4-fluorophenyl)-5-[2-(phenoxy)pyrimidin-4-yl]imidazole;
1-(piperidin-4-yl)-4-(4-fluorophenyl)-5-[2-(3-methoxyphenoxy)pyrimidin-4-yl]imidazole;
1-(piperidin-4-yl)-4-(4-fluorophenyl)-5-[2-(4-phenylphenoxy)pyrimidin-4-yl]imidazole;
1-(piperidin-4-yl)-4-(4-fluorophenyl)-5-[2-(4-phenoxyphenoxy)pyrimidin-4-yl]imidazole;
1-(piperidin-4-yl)-4-(4-fluorophenyl)-5-[2-(3-hydroxyphenoxy)pyrimidin-4-yl]imidazole;
1-(3-(N-morpholino)propyl)-4-(4-fluorophenyl)-5-[2-(4-fluorophenoxy)pyrimidin-4-yl]imidazole;
1-(piperidin-4-yl)-4-(4-fluorophenyl)-5-[2-(2-hydroxyphenoxy)pyrimidin-4-yl]imidazole;
1-(piperidin-4-yl)-4-(4-fluorophenyl)-5-[2-((3,4-methylenedioxy)phenoxy)pyrimidin-4-yl]imidazole;
1-(piperidin-4-yl)-4-(4-fluorophenyl)-5-[2-(3-fluorophenoxy)pyrimidin-4-yl]imidazole;
1-(piperidin-4-yl)-4-(4-fluorophenyl)-5-[2-(2-fluorophenoxy)pyrimidin-4-yl]imidazole;
1-(piperidin-4-yl)-4-(4-fluorophenyl)-5-[2-(2-methoxyphenoxy)pyrimidin-4-yl]imidazole;
1-(piperidin-4-yl)-4-(4-fluorophenyl)-5-[2-(3-trifluoromethylphenoxy)pyrimidin-4-yl]imidazole;
1-(piperidin-4-yl)-4-(4-fluorophenyl)-5-[2-(3,4-difluorophenoxy)pyrimidin-4-yl]imidazole;
1-(piperidin-4-yl)-4-(4-fluorophenyl)-5-[2-(4-methylsulfonylphenoxy)pyrimidin-4-yl]imidazole;
1-(4-piperidinyl)-4-(4-fluorophenyl)-5-(2-thiophenoxypyrimidin-4-yl)imidazole;
1-(4-piperidinyl)-4-(4-fluorophenyl)-5-[2-(1-methyltetrazol-5-ylthio)pyridin-4-yl]imidazole;
5-[2-(2-hydroxyethoxy)pyrimidin-4-yl]-4-(4-fluorophenyl)-1-(4-oxocyclohexyl)imidazole;
5-[2-(2-hydroxyethoxy)]pyrimidin-4-yl]-4-(4-fluorophenyl)-1-(4-hydroxycyclohexyl)imidazole;
5-[2-(2-tert-butylamino)ethoxypyrimidin-4-yl]-4-(4-fluorophenyl)-1-(4-oxocyclohexyl)imidazole;
5-[2-(2-tert-butylamino)ethoxypyrimidin-4-yl]-4-(4-fluorophenyl)-1-(4-hydroxycyclohexyl)imidazole;
1-(4-piperidinyl)-4-(4-Fluorophenyl)-5-(2-isopropoxy-4-pyrimidinyl)imidazole;
1-(4-piperidinyl)-4-(4-Fluorophenyl)-5-(2-methoxy-4-pyrimidinyl)imidazole;
5-(2-hydroxy-4-pyrimidinyl)-4-(4-fluorophenyl)-1-(4-piperidinyl)imidazole;
5-(2-methoxy-4-pyridinyl)-4-(4-fluorophenyl)-1-(4-piperidinyl)imidazole;
5-(2-isopropoxy-4-pyridinyl)-4-(4-fluorophenyl)-1-(4-piperidinyl)imidazole;

5-(2-methylthio-4-pyrimidinyl)-4-(4-fluorophenyl)-1-(4-piperidinyl)imidazole;
5-(2-methylthio-4-pyrimidinyl)-4-(4-fluorophenyl)-1-[1-methyl-4-piperidinyl]imidazole;
5-(2-ethoxy-4-pyrimidinyl)-4-(4-fluorophenyl)-1-(4-piperidinyl)imidazole;
1-(1-ethylcarboxylpiperidin-4-yl)-3-(4-thiomethylphenyl)-5-[2-(thiomethyl)pyrimidin-4-yl]-imidazole;
1-(1-ethylcarbonylpiperidin-4-yl)-4-(4-methylsulfinylphenyl)-5-[(2-methylsulfinyl)pyrimidin-4-yl]imidazole;
2-(4-methylthiophenyl)-4-(4-fluorophenyl)-5-(2-methoxy-4-pyrimidinyl)imidazole;
2-(4-methylsulfinylphenyl)-4-(4-fluorophenyl)-5-(2-methoxy-4-pyrimidinyl)imidazole;
2-[(4-N,N-dimethyl)aminomethylphenyl]-4-(4-fluorophenyl)-5-(2-methoxy-4-pyrimidinyl)imidazole;
2-[(4-N,N-dimethyl)aminomethylphenyl]-4-(4-fluorophenyl)-5-(2-phenoxy-4-pyrimidinyl)imidazole;
(+/−)-2-(4-methylsulfinylphenyl)-4-(4-fluorophenyl)-5-(2-phenoxy-4-pyrimidinyl)imidazole;
2-(4-methylthiophenyl)-4-(4-fluorophenyl)-5-(2-phenoxy-4-pyrimidinyl)imidazole;
and pharmaceutically acceptable salts thereof.

Compounds useful in the practice of the present invention also include, but are not limited to, compounds of formula:

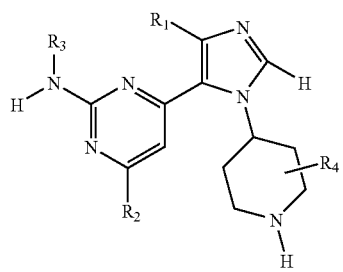

wherein
$R_1$ is hydrogen, $C_{1-5}$ alkyl, halogen, $C_{1-5}$ alkoxy, or aryl$C_{1-5}$ alkyl;
$R_2$ and $R_4$ are independently hydrogen, $C_{1-5}$ alkyl, aryl, aryl$C_{1-5}$ alkyl, heteroaryl, heteroaryl$C_{1-5}$ alkyl, heterocyclic, or heterocyclic$C_{1-5}$ alkyl; and
$R_3$ is hydrogen or $C_{1-3}$ alkyl;
or a pharmaceutically-acceptable salt thereof.

Compounds useful in the practice of the present invention also include, but are not limited to, compounds of formula:

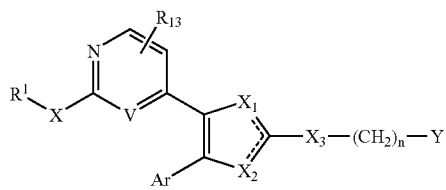

wherein
X is O, $CH_2$, S or NH, or the moiety X—$R^1$ is hydrogen;
$R^1$ is hydrogen, $C_{1-6}$ alkyl, $C_{3-7}$ cycloalkyl, aryl, aryl$C_{1-6}$ alkyl, heterocyclyl, heterocyclyl$C_{1-6}$ alkyl, heteroaryl, or heteroaryl$C_{1-6}$ alkyl, any of which, except for hydrogen, can be optionally substituted;

V is CH or N;
Ar is an aryl or heteroaryl ring, either of which can be optionally substituted;
one of $X_1$ and $X_2$ is N, and the other is $NR^{15}$, wherein $R^{15}$ is hydrogen, $C_{1-6}$ alkyl, or aryl$C_{1-6}$ alkyl;
$X_3$ is a covalent bond or $C(R^2)(R^3)$;
$R^2$ and $R^3$ independently represent optionally substituted $C_{1-6}$ alkyl, or $R^2$ and $R^3$ together with the carbon atom to which they are attached form an optionally substituted $C_{3-7}$ cycloalkyl, $C_{3-7}$ cycloalkenyl, or 5- to 7-membered heterocyclyl ring containing up to three heteroatoms independently selected from N, O, and S;
n is 0, 1, 2, 3, or 4;
Y is $NR^{10}R^{11}$, $NR^{10}C(Z)NR^{10}R^{11}$, $NR^{10}COOR^{11}$, $NR^{10}SO_2R^{11}$, or $C(O)NR^4R^5$;
$R^4$ and $R^5$ independently represent hydrogen, $C_{1-6}$ alkyl, $C_{3-7}$ cycloalkyl, aryl, aryl$C_{1-6}$ alkyl, heteroaryl, heteroaryl$C_{1-6}$ alkyl, heterocyclyl, or heterocyclyl$C_{1-6}$ alkyl, any one of which, except hydrogen, can be optionally substituted, or $R^4$ and $R^5$ together with the nitrogen atom to which they are attached form a 4- to 10-membered optionally-substituted monocyclic or bicyclic ring;
$R^{13}$ is hydrogen, X—$R^1$, halogen, optionally-substituted $C_{1-6}$ alkylsulfinyl, $CH_2OR^{14}$, di-$C_{1-6}$ alkylamino, $N(R^6)C(O)R^7$, $N(R^6)S(O)_2R^8$, or a 5- to 7-membered N-heterocyclyl ring which optionally contains an additional heteroatom selected from O, S, and $NR^9$;
$R^{14}$ is hydrogen, —$C(Z)R^{12}$ or optionally-substituted $C_{1-6}$ alkyl, optionally-substituted aryl, optionally-substituted aryl$C_{1-6}$ alkyl or $S(O)_2R^8$;
$R^6$ is hydrogen or $C_{1-6}$ alkyl;
$R^7$ is hydrogen, $C_{1-6}$ alkyl, $C_{3-7}$ cycloalkyl, aryl, aryl$C_{1-6}$ alkyl, heteroaryl, heteroaryl$C_{1-6}$ alkyl, heterocyclyl or heterocyclyl$C_{1-6}$ alkyl;
$R^8$ is $C_{1-6}$ alkyl, $C_{3-7}$ cycloalkyl, aryl, aryl$C_{1-6}$ alkyl, heteroaryl, heteroaryl$C_{1-6}$ alkyl, heterocyclyl or heterocyclyl$C_{1-6}$ alkyl;
$R^9$ is hydrogen, cyano, $C_{1-4}$ alkyl, $C_{3-7}$ cycloalkyl or aryl;
$R^{10}$, $R^{11}$ and $R^{12}$ are independently selected from hydrogen, $C_{1-6}$ alkyl, $C_{3-7}$ cycloalkyl, heterocyclyl, heterocyclyl$C_{1-6}$ alkyl, heterocyclyl$C_{2-6}$ alkenyl, aryl, aryl$C_{1-6}$ alkyl, aryl$C_{2-6}$ alkenyl, heteroaryl, heteroaryl$C_{1-6}$ alkyl and heteroaryl$C_{2-6}$ alkenyl, any of which can be optionally substituted; or $NR^{10}R^{11}$ can represent a 5- to 7-membered heterocyclyl ring optionally containing an additional heteroatom selected from O, N and S; and
Z is oxygen or sulfur;
or a pharmaceutically-acceptable salt thereof.

Compounds useful in the practice of the present invention also include, but are not limited to, compounds of formulas:

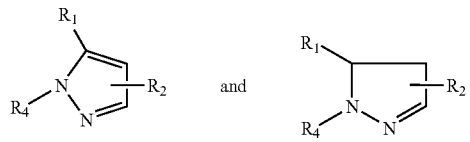

wherein
$R_1$ is a heteroaryl selected from 4-pyridyl, 4-pyrimidinyl, 4-quinolyl, 6-isoquinolinyl, quinazolin-4-yl, 1-imidazolyl, 1-benzimidazolyl, 4-pyridazinyl, and a 1,2,4-triazin-5-yl ring, which heteroaryl ring is substituted one to three times with Y, $NHR_a$, optionally-substituted $C_{1-4}$ alkyl, halogen, hydroxyl, optionally-substituted $C_{1-4}$ alkoxy, optionally-substituted $C_{1-4}$ alkylthio, optionally-substituted $C_{1-4}$ alkylsulfinyl, $CH_2OR_{12}$, amino, mono- and di-$C_{1-6}$ alkyl-substituted amino, $N(R_{10})C(O)R_b$, $N(R_{10})S(O)_2R_d$, or an N-heterocyclyl ring which has from 5 to 7 members and optionally contains an additional heteroatom selected from oxygen, sulfur or $NR_{15}$;

Y is $X_1$—$R_1$;

$X_1$ is oxygen or sulfur;

$R_a$ is $C_{1-6}$ alkyl, aryl, aryl$C_{1-6}$ alkyl, heterocyclic, heterocyclyl$C_{1-6}$ alkyl, heteroaryl, or heteroaryl$C_{1-6}$ alkyl, wherein each of these moieties can be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl;

$R_d$ is $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl;

$R_4$ is phenyl, naphth-1-yl, naphth-2-yl, a heteroaryl or a fused phenyl-containing ring system, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, —$C(Z)NR_7R_{17}$, —$C(Z)OR_{16}$, —$(CR_{10}R_{20})_vCOR_{12}$, —$SR_5$, —$SOR_5$, —$OR_{12}$, halo-substituted-$C_{1-4}$ alkyl, $C_{1-4}$ alkyl, —$ZC(Z)R_{12}$, —$NR_{10}C(Z)R_{16}$, or —$(CR_{10}R_{20})_vNR_{10}R_{20}$ and which, for other positions of substitution, is halogen, cyano, nitro, phenyl, —$C(Z)NR_{13}R_{14}$, —$C(Z)OR_f$, —$(CR_{10}R_{20})_{m''}COR_f$, —$S(O)_mR_f$, —$OR_f$, halo-substituted $C_{1-4}$ alkyl, $C_{1-10}$ alkyl, —$ZC(Z)R_f$, optionally-substituted phenyl, —$(CR_{10}R_{20})_{m''}NR_{10}C(Z)R_f$, —$NR_{10}S(O)_mR_8$, —$NR_{10}S(O)_mNR_7R_{17}$, —$ZC(Z)R_{12}$, or —$(CR_{10}R_{20})_{m''}NR_{13}R_{14}$;

$R_f$ is heterocyclyl, heterocyclyl$C_{11}$—O alkyl or $R_8$;

v is 0, 1, or 2;

m is 0, 1, or 2;

m' is 1 or 2;

m'' is 0, 1, 2, 3, 4, or 5;

$R_2$ hydrogen, —$(CR_{10}R_{23})_nOR_9$, heterocylyl, heterocyclyl$C_{1-10}$ alkyl, $C_{1-10}$ alkyl, halo-substiuted $C_{1-10}$ alkyl, $C_{2-10}$ alkenyl, $C_{2-10}$ alkynyl, $C_{3-7}$ cycloalkyl, $C_{3-7}$ cycloalkyl$C_{1-10}$ alkyl, $C_{5-7}$ cycloalkenyl, $C_{5-7}$ cycloalkenyl$C_{1-10}$ alkyl, aryl, aryl$C_{1-10}$ alkyl, heteroaryl, heteroaryl$C_{1-10}$ alkyl, $(CR_{10}R_{23})_nOR_{11}$, $(CR_{10}R_{23})_nS(O)_mR_{18}$, $(CR_{10}R_{23})_nNHS(O)_2R_{18}$, $(CR_{10}R_{23})_nNR_{13}R_{14}$, $(CR_{10}R_{23})_nNO_2$, $(CR_{10}R_{23})_nCN$, $(CR_{10}R_{23})_nS(O)_mNR_{13}R_{14}$, $(CR_{10}R_{23})_nC(Z)R_{11}$, $(CR_{10}R_{23})_nOC(Z)R_{11}$, $(CR_{10}R_{23})_nC(Z)OR_{11}$, $(CR_{10}R_{23})_nC(Z)NR_{13}R_{14}$, $(CR_{10}R_{23})_nC(Z)NR_{11}R_9$, $(CR_{10}R_{23})_nNR_{10}C(Z)R_{11}$, $(CR_{10}R_{23})_nNR_{10}C(Z)NR_{13}R_{14}$, $(CR_{10}R_{23})_nN(OR_6)C(Z)NR_{13}R_{14}$, $(CR_{10}R_{23})_nN(OR_6)C(Z)R_{11}$, $(CR_{10}R_{23})_nC(=NOR_6)R_{11}$, $(CR_{10}R_{23})_nNR_{10}C(=NR_{19})NR_{13}R_{14}$, $(CR_{10}R_{23})_nOC(Z)NR_{13}R_{14}$, $(CR_{10}R_{23})_nNR_{10}C(Z)NR_{13}R_{14}$, $(CR_{10}R_{23})_nNR_{10}C(Z)OR_{10}$, $5$-$(R_{18})$-$1,2,4$-oxadiazol-3-yl or $4$-$(R_{12})$-$5$-$(R_{18}R_{19})$-$4,5$-dihydro-$1,2,4$-oxadiazol-3-yl; wherein the aryl, arylalkyl, heteroaryl, heteroaryl alkyl, cycloalkyl, cycloalkyl alkyl, heterocyclic and heterocyclic alkyl groups can be optionally substituted;

n is 0, or an integer having a value of 1 to 10;

Z is oxygen or sulfur;

$R_5$ is hydrogen, $C_{1-4}$ alkyl, $C_{2-4}$ alkenyl, $C_{2-4}$ alkynyl or $NR_7R_{17}$, excluding the moieties —$SR_5$ being —$SNR_7R_{17}$ and —$S(O)R_5$ being —$SOH$;

$R_6$ is hydrogen, a pharmaceutically-acceptable cation, $C_{1-10}$ alkyl, $C_{3-7}$ cycloalkyl, aryl, aryl$C_{1-4}$ alkyl, heteroaryl, heteroaryl$C_{1-4}$ alkyl, heterocyclyl, aroyl, or $C_{1-10}$ alkanoyl;

$R_7$ and $R_{17}$ are each independently selected from hydrogen or $C_{1-4}$ alkyl, or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, or $(CR_{10}R_{20})_nNR_{13}R_{14}$, wherein the aryl, arylalkyl, heteroaryl, and heteroaryl alkyl can be optionally substituted;

$R_9$ is hydrogen, —$C(Z)R_{11}$, optionally-substituted $C_{1-10}$ alkyl, $S(O)_2R_{18}$, optionally-substituted aryl or optionally-substituted aryl$C_{1-4}$ alkyl;

$R_{10}$ and $R_{20}$ are each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl$C_{1-10}$ alkyl, aryl, aryl$C_{1-10}$ alkyl, heteroaryl or heteroaryl$C_{1-10}$ alkyl, wherein the aryl, arylalkyl, heteroaryl, heteroaryl alkyl, heterocyclyl or heterocyclylalkyl can be optionally substituted;

$R_{12}$ is hydrogen or $R_{16}$;

$R_{13}$ and $R_{14}$ are each independently selected from hydrogen or optionally-substituted $C_{1-4}$ alkyl, optionally-substituted aryl or optionally-substituted aryl$C_{1-4}$ alkyl, or together with the nitrogen to which they are attached form a heterocyclic ring of 5 to 7 members which ring optionally contains an additional heteroatom selected from oxygen, sulfur or $NR_9$;

$R_{15}$ is hydrogen, $C_{1-4}$ alkyl or $C(Z)$-$C_{1-4}$ alkyl;

$R_{16}$ is $C_{1-4}$ alkyl, halo-substituted $C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$C_{1-10}$ alkyl, heterocyclyl, heterocyclyl$C_{1-10}$ alkyl, heteroaryl or heteroaryl$C_{1-10}$ alkyl, wherein the aryl, arylalkyl, heteroaryl, heteroaryl alkyl, heterocyclyl or heterocyclylalkyl can be optionally substituted;

$R_{19}$ is hydrogen, cyano, $C_{1-4}$ alkyl, $C_{3-7}$ cycloalkyl or aryl; and $R_{23}$ is hydrogen, $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl, all of which can be optionally substituted;

or a pharmaceutically-acceptable salt thereof.

Exemplary compounds of these formulas include:

4-[1-(4-fluorophenyl)-3-phenyl-1H-pyrazol-5-yl]pyridine

4-[4-bromo-1-(4-fluorophenyl)-3-phenyl-1H-pyrazol-5-yl]pyridine

4-[1-(4-fluorophenyl)-3-[4-(methylthio)phenyl]-1H-pyrazol-5-yl]pyridine

4-[1-(4-fluorophenyl)-3-[4-(methylsulfonyl)phenyl]-1H-pyrazol-5-yl]pyridine 4-[1-(4-fluorophenyl)-3-[4-(methylsulfinyl)phenyl]-1H-pyrazol-5-yl]pyridine;

4-[1-(4-fluorophenyl)-4,5-dihydro-3-phenyl-1H-pyrazol-5-yl]pyridine

4-[1-(4-fluorophenyl)-4,5-dihydro-3-[4-(methylthio)phenyl]-1H-pyrazol-5-yl]pyridine
and pharmaceutically acceptable salts thereof.

Compounds useful in the practice of the present invention also include, but are not limited to, compounds of formulas:

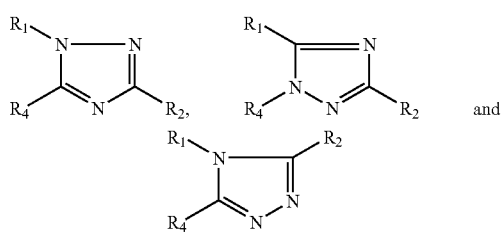

wherein $R_1$ is 4-pyridyl or 4-pyrimidinyl ring, which ring is optionally substituted one or more times with Y, $C_{1-4}$ alkyl, halogen, hydroxyl, $C_{1-4}$ alkoxy, $C_{1-4}$ alkylthio, $C_{1-4}$ alkylsulfinyl, $CH_2OR_{12}$, amino, mono- and di-$C_{1-6}$ alkyl-substituted amino, $N(R_{10})C(O)R_b$, or an N-heterocyclyl ring which has from 5 to 7 members and optionally contains an additional heteroatom selected from oxygen, sulfur or $NR_5$;

Y is $X_1$—$R_a$;

$X_1$ is oxygen, sulfur, or NH;

$R_a$ is $C_{1-6}$ alkyl, aryl, aryl$C_{1-6}$ alkyl, heterocyclic, heterocyclyl$C_{1-6}$ alkyl, heteroaryl, or heteroaryl$C_{1-6}$ alkyl, wherein each of these moieties can be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl, wherein each of these moieties can be optionally substituted;

$R_4$ is phenyl, naphth-1-yl, naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, —$C(Z)NR_7R_{17}$, —$C(Z)OR_{16}$, —$(CR_{10}R_{20})_vCOR_{12}$, —$SR_5$, —$SOR_5$, —$OR_{12}$, halo-substituted-$C_{1-4}$ alkyl, $C_{1-4}$ alkyl, —$ZC(Z)R_{12}$, —$NR_{10}C(Z)R_{16}$, or —$(CR_{10}R_{20})_vNR_{10}R_{20}$ and which, for other positions of substitution, is halogen, cyano, —$C(Z)NR_{13}R_{14}$, —$C(Z)OR_f$, —$(CR_{10}R_{20})_{m''}COR_f$, —$S(O)_mR_f$, —$OR_f$, halo-substituted $C_{1-4}$ alkyl, $C_{1-4}$ alkyl, —$ZC(Z)R_f$, —$(CR_{10}R_{20})_{m''}NR_{10}C(Z)R_f$, —$NR_{10}S(O)_mR_8$, —$NR_{10}S(O)_mNR_7R_{17}$, or —$(CR_{10}R_{20})_{m''}NR_{13}R_{14}$;

$R_f$ is heterocyclyl, heterocyclyl$C_{1-10}$ alkyl or $R_8$;

v is 0, 1, or 2;

m is 0, 1, or 2;

m' is 1 or 2;

m'' is 0, 1, 2, 3, 4, or 5;

$R_2$ hydrogen, $C(H)(A)(R_{22})$, —$(CR_{10}R_{23})_nOR_9$, heterocylyl, heterocyclyl$C_{1-10}$ alkyl, $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$ cycloalkyl$C_{1-10}$ alkyl, $C_{5-7}$ cycloalkenyl, $C_{5-7}$cycloalkenyl$C_{1-10}$ alkyl, aryl, aryl$C_{1-10}$ alkyl, heteroaryl, heteroaryl$C_{1-10}$ alkyl, $(CR_{10}R_{23})_nOR_{11}$, $(CR_{10}R_{23})_nS(O)_mR_{18}$, $(CR_{10}R_{23})_nNR_{13}RHS(O)_2R_{18}$, $(CR_{10}R_{23})_nNR_{13}R_{14}$, $(CR_{10}R_{23})_nNO_2$, $(CR_{10}R_{23})_nCN$, $(CR_{10}R_{23})_nS(O)_mNR_{13}R_{14}$, $(CR_{10}R_{23})_nC(Z)R_{11}$, $(CR_{10}R_{23})_nOC(Z)R_{11}$, $(CR_{10}R_{23})_nC(Z)OR_{11}$, $(CR_{10}R_{23})_nC(Z)NR_{13}R_{14}$, $(CR_{10}R_{23})_nC(Z)NR_{11}OR_9$, $(CR_{10}R_{23})_nNR_{10}C(Z)R_{11}$, $(CR_{10}R_{23})_nNR_{10}C(Z)NR_{13}R_{14}$, $(CR_{10}R_{23})_nN(OR_6)C(Z)NR_{13}R_{14}$, $(CR_{10}R_{23})_nN(OR_6)C(Z)R_{11}$, $(CR_{10}R_{23})_nC(=NOR_6)R_{11}$, $(CR_{10}R_{23})_nNR_{10}C(=NR_{19})NR_{13}R_{14}$, $(CR_{10}R_{23})_nOC(Z)NR_{13}R_{14}$, $(CR_{10}R_{23})_nNR_{10}C(Z)NR_{13}R_{14}$, $(CR_{10}R_{23})_nNR_{10}C(Z)OR_{10}$, 5-($R_{18}$)-1,2,4-oxadiazol-3-yl or 4-($R_{12}$)-5-($R_{18}R_{19}$)-4,5-dihydro-1,2,4-oxadiazol-3-yl; wherein the aryl, arylalkyl, heteroaryl, heteroaryl alkyl, cycloalkyl, cycloalkyl alkyl, heterocyclic and heterocyclic alkyl groups can be optionally substituted;

A is an optionally-substituted aryl, heterocyclyl or heteroaryl ring, or A is a substituted $C_{1-10}$ alkyl;

n is 0, or an integer having a value of 1 to 10;

Z is oxygen or sulfur;

$R_5$ is hydrogen, $C_{1-4}$ alkyl, $C_{2-4}$ alkenyl, $C_{2-4}$ alkynyl or $NR_7R_{17}$, excluding the moieties —$SR_5$ being —$SNR_7R_{17}$ and —$S(O)R_5$ being —$SOH$;

$R_6$ is hydrogen, a pharmaceutically-acceptable cation, $C_{1-10}$ alkyl, $C_{3-7}$ cycloalkyl, aryl, aryl$C_{1-4}$ alkyl, heteroaryl, heteroaryl$C_{1-4}$ alkyl, heterocyclyl, aroyl, or $C_{1-10}$ alkanoyl;

$R_7$ and $R_{17}$ are each independently selected from hydrogen or $C_{1-4}$ alkyl, or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, or $(CR_{10}R_{20})_vNR_{13}R_{14}$, wherein the aryl, arylalkyl, heteroaryl, and heteroaryl alkyl can be optionally substituted;

$R_9$ is hydrogen, —$C(Z)R_{11}$, optionally-substituted $C_{1-10}$ alkyl, $S(O)_2R_{18}$, optionally-substituted aryl or optionally-substituted aryl$C_{1-4}$ alkyl;

$R_{10}$ and $R_{20}$ are each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl$C_{1-10}$ alkyl, aryl, aryl$C_{1-10}$ alkyl, heteroaryl or heteroaryl$C_{1-10}$ alkyl, wherein the aryl, arylalkyl, heteroaryl, heteroaryl alkyl, heterocyclyl or heterocyclylalkyl can be optionally substituted;

$R_{12}$ is hydrogen or $R_{16}$;

$R_{13}$ and $R_{14}$ are each independently selected from hydrogen or optionally-substituted $C_{1-4}$ alkyl, optionally-substituted aryl or optionally-substituted aryl$C_{1-4}$ alkyl, or together with the nitrogen to which they are attached form a heterocyclic ring of 5 to 7 members which ring optionally contains an additional heteroatom selected from oxygen, sulfur or $NR_9$;

$R_{15}$ is $R_{10}$ or $C(Z)C_{1-4}$ alkyl;

$R_{16}$ is $C_{1-4}$ alkyl, halo-substituted $C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$C_{1-10}$ alkyl, heterocyclyl, heterocyclyl$C_{1-10}$ alkyl, heteroaryl or heteroaryl$C_{1-10}$ alkyl;

$R_{19}$ is hydrogen, cyano, $C_{1-4}$ alkyl, $C_{3-7}$ cycloalkyl or aryl; and $R_{23}$ is hydrogen, $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl, all of which can be optionally substituted;

or a pharmaceutically-acceptable salt thereof.

Exemplary compounds of these formulas include:
1-(pyrid-4-yl)-3-phenyl-5-(4-fluorophenyl)-1,2,4-triazole;
1-(6-aminopyrimidin-4-yl)-3-phenyl-5-(4-fluorophenyl)-1,2,4-triazole;
1-[4-(6,7-dimethoxyquinazoline)]-3-phenyl-5-(4-fluorophenyl)-1,2,4-triazole;
1-(4-fluorophenyl)-3-phenyl-5-(2-aminopyrimidin-4-yl)-1,2,4-triazole;
3-(4-fluorophenyl)-4-(2-aminopyrimidin-4-yl)-5-phenyl-1,2,4-triazole;
and pharmaceutically acceptable salts thereof.

Compounds useful in the practice of the present invention also include, but are not limited to, compounds of formula:

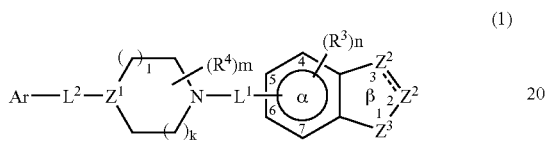
(1)

and the pharmaceutically acceptable salts thereof, or a pharmaceutical composition thereof, wherein ⇝ represents a single or double bond;

one $Z^2$ is CA or $CR^8A$ and the other is $CR^1$, $CR^1{}_2$, $NR^6$ or N wherein each $R^1$, $R^6$ and $R^8$ is independently hydrogen or noninterfering substituent;

A is $-CO(X)_jY$ wherein Y is $COR^2$ or an isostere thereof and $R^2$ is hydrogen or a noninterfering substituent, X is a spacer preferably 2-6 Å in length, and j is 0 or 1;

$Z^3$ is $NR^7$ or O;

each $R^3$ is independently a noninterfering substituent, wherein a "noninterfering substituent" is one that does not reduce the inhibitor activity of the compound;

n is 0-3;

each of $L^1$ and $L^2$ is a linker;

each $R^4$ is independently a noninterfering substituent;

m is 0-4;

$Z^1$ is $CR^5$ or N wherein $R^5$ is hydrogen or a noninterfering substituent;

each of l and k is an integer from 0-2 wherein the sum of l and k is 0-3;

Ar is an aryl group substituted with 0-5 noninterfering substituents, wherein two noninterfering substituents can form a fused ring; and the distance between the atom of Ar linked to $L^2$ and the center of the α ring is preferably 4.5-24 Å.

As used herein, a "noninterfering substituent" is a substituent which leaves the ability of the compound of formula (1) to inhibit p38-α activity qualitatively intact. Thus, the substituent may alter the degree of inhibition of p38-α. However, as long as the compound of formula (1) retains the ability to inhibit p38-α activity, the substituent will be classified as "noninterfering." A number of assays for determining the ability of any compound to inhibit p38-α activity are available in the art. A whole blood assay for this evaluation is illustrated below: the gene for p38-α has been cloned and the protein can be prepared recombinantly and its activity assessed, including an assessment of the ability of an arbitrarily chosen compound to interfere with this activity. The essential features of the molecule are tightly defined. The positions which are occupied by "noninterfering substituents" can be substituted by conventional organic moieties as is understood in the art. It is irrelevant to the present invention to test the outer limits of such substitutions. The essential features of the compounds are those set forth with particularity herein.

Compounds useful in the practice of the present invention also include, but are not limited to, compounds of formulas:

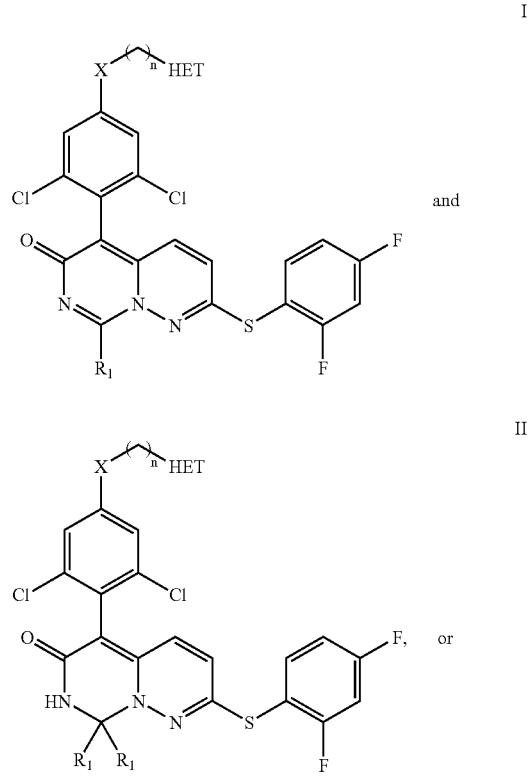

pharmaceutically acceptable salts thereof, wherein

HET is a 5-7 membered heterocycle with 1 to 4 N, S or O atoms, which heterocycle is substituted with 1 to 3 $C_1$-$C_4$ branched or straight chain alkyl groups. HET can optionally be substituted with halo, cyano, $N(R')_2$, OR', $CO_2R'$, $CON(R')_2$, and $SO_2N(R^2)_2$;

X is O or NR';

n is 1 to 3;

R' is selected from hydrogen, ($C_1$-$C_3$)-alkyl, ($C_2$-$C_3$)-alkenyl or alkynyl, phenyl or phenyl substituted with 1 to 3 substituents independently selected from halo, methoxy, cyano, nitro, amino, hydroxy, methyl or ethyl; or a 5-6 membered heterocyclic ring system optionally substituted with 1 to 3 substituents independently selected from halo, methoxy, cyano, nitro, amino, hydroxy, methyl or ethyl;

$R_1$ is selected from hydrogen, ($C_1$-$C_3$)-alkyl, hydroxy, or ($C_1$-$C_3$)-alkoxy;

$R_2$ is selected from hydrogen, ($C_1$-$C_3$)-alkyl, or ($C_1$-$C_3$)-alkenyloxy; each optionally substituted with $-N(R')_2$, $-OR'$, $-SR'$, $-C(O)-N(R')_2$, $-S(O_2)-N(R')_2$, $-C(O)-OR'$, or $R^3$; and $R^3$ is selected from 5-6 membered aromatic carbocyclic or heterocyclic ring systems.

Compounds useful in the practice of the present invention also include, but are not limited to, compounds of formulas:

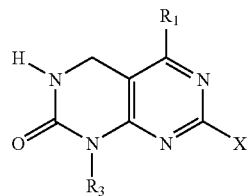
(I)

or

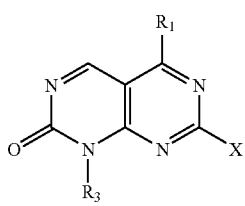
(Ia)

wherein
- R₁ is an aryl or heteroaryl ring, which ring is optionally substituted;
- R₂ is hydrogen, $C_{1-10}$ alkyl, $C_{3-7}$ cycloalkyl, $C_{3-7}$ cycloalkyl$C_{1-10}$ alkyl, aryl, aryl$C_{1-10}$ alkyl, heteroaryl, heteroaryl$C_{1-10}$ alkyl, heterocyclic, or a heterocyclyl$C_{1-10}$ alkyl moiety; and wherein each of these moieties, excluding hydrogen, are optionally substituted;
- R₃ is a $C_{1-10}$ alkyl, $C_{3-7}$ cycloalkyl, $C_{3-7}$ cycloalkyl$C_{1-10}$alkyl, aryl$C_{1-10}$alkyl, heteroaryl $C_{1-10}$alkyl, or heterocyclyl$C_{1-10}$ alkyl moiety; and wherein each of these moieties are optionally substituted;
- X is R₂, OR₂, $S(O)_mR_2$ or $(CH_2)_nNR_4R_{14}$, or $(CH_2)_nNR_2R_4$;
- n is 0 or an integer having a value of 1 to 10;
- m is 0 or an integer having a value of 1 or 2;
- R₄ and R₁₄ are each independently selected from hydrogen, optionally substituted $C_{1-14}$ alkyl, optionally substituted aryl, or an optionally substituted aryl$C_{1-4}$alkyl, or R₄ and R₁₄ together with the nitrogen to which they are attached form a heterocyclic ring of 5 to 7 members, which ring optionally contains an additional heteroatom selected from oxygen, sulfur or NR₉, and which ring can be optionally substituted;
- R₆ is hydrogen, $C_{1-10}$ alkyl, $C_{3-7}$ cycloalkyl, heterocyclyl, heterocyclyl$C_{1-10}$alkyl, aryl, aryl$C_{1-10}$ alkyl, heteroaryl or a heteroaryl$C_{1-10}$ alkyl moiety; and wherein each of these moieties, excluding hydrogen, can be optionally substituted;
- R₉ is hydrogen, C(Z)R₆, optionally substituted $C_{1-10}$ alkyl, optionally substituted aryl or optionally substituted aryl$C_{1-4}$ alkyl;
- Z is oxygen or sulfur;

or a pharmaceutically acceptable salt thereof.

Compounds useful in the practice of the present invention also include, but are not limited to, compounds of formulas:

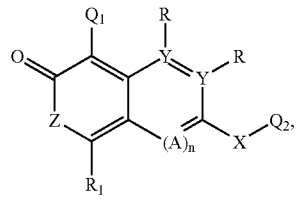
I

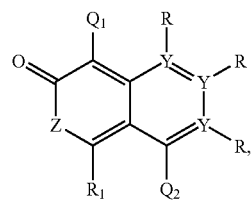
II

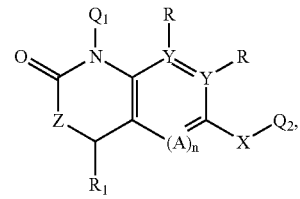
III

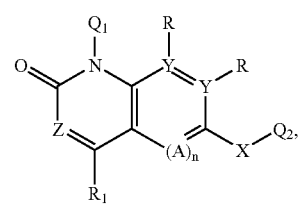
IV

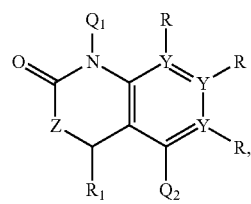
V

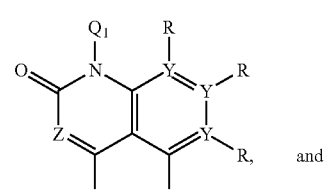
VI
and

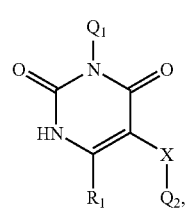
VII or pharmaceutically acceptable salts thereof, wherein each of $Q_1$ and $Q_2$ are independently selected from 5-6 membered aromatic carbo cyclic or hetero cyclic ring systems, or 8-10 membered bicyclic ring systems comprising aromatic carbo cyclic rings, aromatic heterocyclic rings or a combination of an aromatic carbocyclic ring and an aromatic heterocyclic ring;

the rings that make up $Q_1$ are substituted with 1 to 4 substituents, each of which is independently selected from halo; $C_1$-$C_3$ alkyl optionally substituted with $NR'_2$, $OR'$, $CO_2R'$ or $CONR'_2$; ($C_1$-$C_3$)-alkoxy optionally substituted with $NR'_2$, $OR'$, $CO_2R'$ or $CONR'_2$; $NR'_2$; $OCF_3$; $CF_3$; $NO_2$; $CO_2R'$; $CONR'$; $SR'$; $S(O_2)N(R')_2$; $SCF_3$; CN; $N(R')C(O)R^4$; $N(R')C(O)OR^4$; $N(R')C(O)C(O)R^4$; $N(R')S(O_2)R^4$; $N(R')R^4$; $N(R^4)_2$; $OR^4$; $OC(O)R^4$; $OP(O)_3H_2$; or $N=C-N(R')_2$;

the rings that make up $Q_2$ are optionally substituted with up to 4 substituents, each of which is independently selected from halo; $C_1$-$C_3$ straight or branched alkyl optionally substituted with $NR'_2$, $OR'$, $CO_2R'$, $S(O_2)N(R')_2$, $N=C-N(R')_2$, $R^3$, or $CONR'_2$; ($C_1$-$C_3$)-alkoxy optionally substituted with $NR'_2$, $OR'$, $CO_2R'$, $S(O_2)N(R')_2$, $N=C-N(R')_2$, $R^3$, or $CONR'$; $NR'_2$; $OCF_3$; $CF_3$; $NO_2$; $CO_2R'$; $CONR'$; $R^3$; $OR^3$; $NR^3$; $SR^3$; $C(O)R^3$; $C(O)N(R')R^3$; $C(O)OR^3$; $SR'$; $S(O_2)N(R')_2$; $SCF_3$; $N=C-N(R')_2$; or CN;

$R'$ is selected from hydrogen, ($C_1$-$C_3$)-alkyl; ($C_2$-$C_3$)-alkenyl; ($C_2$-$C_3$) alkynyl; phenyl substituted with 1 to 3 substituents independently selected from halo, methoxy, cyano, nitro, amino, hydroxy, methyl or ethyl;

$R^3$ is selected from 5-6 membered aromatic carbocyclic or heterocyclic ring systems;

$R^4$ is ($C_1$-$C_4$)-alkyl optionally substituted with $N(R')_2$, $OR'$, $CO_2R'$, $CON(R')_2$, or $SO_2N(R^2)_2$; or a 5-6 membered carbocyclic or heterocyclic ring system optionally substituted with $N(R')_2$, $OR'$, $CO_2R'$, $CON(R')_2$, or $SO_2N(R^2)_2$;

X, if present, is selected from —S—, —O—, —$S(O_2)$—, —S(O)—, —$S(O_2)$—$N(R^2)$—, —$N(R^{-N(R2)})$—C(O)O—, —O—C(O)—$N(R^2)$, —C(O)—, —C(O)O—, —O—C(O)—, —C(O)—$N(R^2)$—, —$N(R^2)$—C(O)—, —$N(R^2)$—, —$C(R^2)_2$—, or —$C(OR^2)_2$—;

each R is independently selected from hydrogen, —$R^2$, —$N(R^2)_2$, —$OR^2$, $SR^2$, —C(O)—$N(R^2-S(O_2)-N(R^2)_2$, or —C(O)—$OR^2$, wherein two adjacent R are optionally bound to one another and, together with each Y to which they are respectively bound, form a 4-8 membered carbocyclic or heterocyclic ring;

$R^2$ is selected from hydrogen, ($C_1$-$C_3$)-alkyl, or ($C_1$-$C_3$)-alkenyl; each optionally substituted with —$N(R')_2$, —OR', SR', —C(O)—$N(R')_2$, —$S(O_2)$—$N(R')_2$, —C(O)—OR', or $R^3$;

Y is N or C;

Z, if present, is N, NH, or, if chemically feasible, O;

A, if present, is N or CR';

n is 0 or 1; and $R_1$ is selected from hydrogen, ($C_1$-$C_3$)-alkyl, hydroxy, or ($C_1$-$C_3$)-alkoxy.

Compounds useful in the practice of the present invention also include, but are not limited to, compounds of formula:

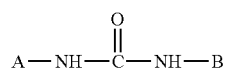

wherein A is (a)

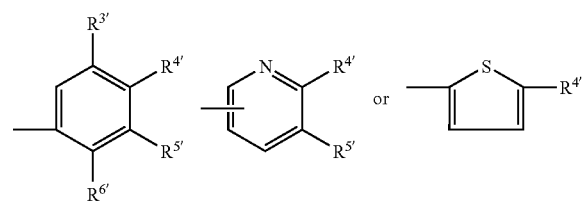

wherein $R^{3'}$, $R^4$, R are each independently H, $C_{1-10}$-alkyl, optionally substituted by halogen up to perhalo, $C_{1-10}$ alkoxy, optionally substituted by halogen, up to perhaloalkoxy, halogen; $NO_2$ or $NH_2$;

$R^{6'}$ is H, $C_{1-10}$-alkyl, $C_{1-10}$ alkoxy, —$NHCOR^1$; —$NR^1COR^1$; $NO_2$;

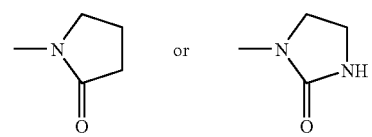

one of $R^{4'}$, $R^{5'}$, or $R^{6'}$ can be —X—Y; or 2 adjacent $R^{4'}$—$R^{6'}$ can together be an aryl or heteroaryl ring with 5-12 atoms, optionally substituted by $C_{1-10}$-alkyl, $C_{1-10}$ alkoxy, $C_{3-10}$ cycloalkyl, $C_{2-10}$ alkenyl, $C_{1-10}$ alkanoyl, $C_{6-12}$ aryl, $C_{5-12}$ heteroaryl or $C_{6-12}$ arakyl;

$R^1$ is $C_{1-10}$-alkyl optionally substituted by halogen, up to perhalo;

X is —$CH_2$—, —S—, —$N(CH_3)$—, —NHC(O)—, —$CH_2$—S—, —S—$CH_2$—, —C(O)—,

X is additionally a single bond where Y is pyridyl;

Y is phenyl, pyridyl, naphthyl, pyridone, pyrazine, benzodioxane, benzopyridine, pyrimidine or benzothiazole, each optionally substituted by $C_{1-10}$-alkyl, $C_{1-10}$-alkoxy, halogen, OH, —$SCH_3$ or $NO_2$ or, where Y is phenyl, by

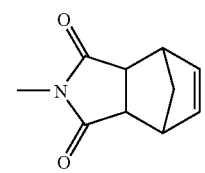

or a pharmaceutically-acceptable salt thereof;

or (b)

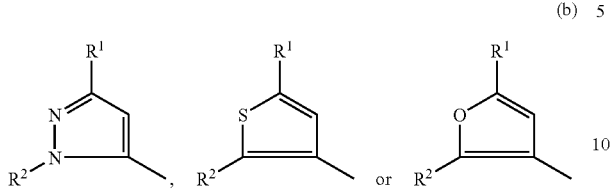

wherein
R¹ is selected from the group consisting of $C_3$-$C_{10}$ alkyl, $C_3$-$C_{10}$ cycloalkyl, up to per-halo substituted $C_1$-$C_{10}$ alkyl and up to per-halosubstituted $C_3$-$C_{10}$ cycloalkyl; and R² is $C_6$-$C_{14}$ aryl, $C_3$-$C_{14}$ heteroaryl, substituted $C_6$-$C_{14}$ aryl or substituted $C_3$-$C_{14}$ heteroaryl;

wherein if R² is a substituted group, it is preferably substituted by one or more substituents independently selected from the group consisting of halogen, up to per-halosubstitution, and $V_n$, where n=0-3 and each V is independently selected from the group consisting of —CN, —OC(O)NR⁵R⁵', —CO₂R⁵, —C(O)NR⁵R⁵', —OR⁵, —SR⁵, —NR⁵R⁵', —C(O)R⁵, —NR⁵C(O)OR⁵', —SO₂R⁵, —SOR⁵, —NR⁵C(O)R⁵', —NO₂, $C_1$-$C_{10}$ alkyl, $C_3$-$C_{10}$ cycloalkyl, $C_6$-$C_{14}$ aryl, $C_3$-$C_{13}$ heteroaryl, $C_7$-$C_{24}$ alkaryl, $C_4$-$C_{24}$ alkheteroaryl, substituted $C_1$-$C_{10}$ alkyl, substituted $C_3$-$C_{10}$ cycloalkyl, substituted $C_6$-$C_{14}$ aryl, substituted $C_3$-$C_{13}$ heteroaryl, substituted $C_7$-$C_{24}$ alkaryl and substituted $C_4$-$C_{24}$ alkheteroaryl;

wherein if V is a substituted group, it is substituted by one or more substituents independently selected from the group consisting of halogen, up to per-halosubstitution, —CN, —CO₂R⁵, —C(O)R⁵, —C(O)NR⁵R⁵', —NR⁵R⁵', —OR⁵, —SR⁵, —NR⁵C(O)R⁵', —NR⁵C(O)OR⁵' and —NO₂; and R⁵ and R⁵' are independently selected form the group consisting of H, $C_1$-$C_{10}$ alkyl, $C_3$-$C_{10}$ cycloalkyl, $C_6$-$C_{14}$ aryl, $C_3$-$C_{13}$ heteroaryl, $C_7$-$C_{24}$ alkaryl, $C_4$-$C_{23}$ alkheteroaryl, up to per-halosubstituted $C_1$-$C_{10}$ alkyl, up to per-halosubstituted $C_3$-$C_{10}$ cycloalkyl, up to per-halosubstituted $C_6$-$C_{14}$ aryl and up to per-halosubstituted $C_3$-$C_{13}$ heteroaryl;

or a pharmaceutically-acceptable salt thereof;

or (c) a substituted moiety of up to 40 carbon atoms of the formula: -L-(M-L¹)$_q$, where L is a 5- or 6-membered cyclic structure bound directly to D, L¹, comprises a substituted cyclic moiety having at least 5 members, M is a bridging group having at least one atom, q is an integer of from 1-3; and each cyclic structure of L and L¹ contains 0-4 members of the group consisting of nitrogen, oxygen and sulfur;

L¹ is substituted by at least one substituent selected from the group consisting of —SO₂R$_x$, —C(O)R$_x$ and —C(NR$_y$)R$_z$;

R$_y$ is hydrogen or a carbon-based moiety of up to 24 carbon atoms optionally containing heteroatoms selected from N, S and O and optionally halosubstituted, up to perhalo;

R$_z$ is hydrogen or a carbon-based moiety of up to 30 carbon atoms optionally containing heteroatoms selected from N, S and O and optionally substituted by halogen, hydroxy and carbon-based substituents of up to 24 carbon atoms, which optionally contain heteroatoms selected from N, S and O and are optionally substituted by halogen; and R$_x$ is R$_z$ or NR$_a$R$_b$ where R$_a$ and R$_b$ are
i) independently hydrogen,
a carbon-based moiety of up to 30 carbon atoms optionally containing heteroatoms selected from N, S and O and optionally substituted by halogen, hydroxy and carbon-based substituents of up to 24 carbon atoms, which optionally contain heteroatoms selected from N, S and O and are optionally substituted by halogen, or
—OSi(R$_f$)₃ where R$_f$ is hydrogen or a carbon-based moiety of up to 24 carbon atoms optionally containing heteroatoms selected from N, S and O and optionally substituted by halogen, hydroxy and carbon-based substituents of up to 24 carbon atoms, which optionally contain heteroatoms selected from N, S and O and are optionally substituted by halogen; or ii) R$_a$ and R$_b$ together form a 5-7 member heterocyclic structure of 1-3 heteroatoms selected from N, S and O, or a substituted 5-7 member heterocyclic structure of 1-3 heteroatoms selected from N, S and O, substituted by halogen, hydroxy or carbon-based substituents of up to 24 carbon atoms, which optionally contain heteroatoms selected from N, S and O and are optionally substituted by halogen; or iii) one of R$_a$ or R$_b$ is —C(O)—, a $C_1$-$C_5$ divalent alkylene group or a substituted $C_1$-$C_5$ divalent alkylene group bound to the moiety L to form a cyclic structure with at least 5 members, wherein the substituents of the substituted $C_1$-$C_5$ divalent alkylene group are selected from the group consisting of halogen, hydroxy, and carbon-based substituents of up to 24 carbon atoms, which optionally contain heteroatoms selected from N, S and O and are optionally substituted by halogen;

or a pharmaceutically-acceptable salt thereof; and

B is an unsubstituted or substituted, up to tricyclic, aryl or heteroaryl moiety with up to 30 carbon atoms with at least one 5- or 6-membered aromatic structure containing 0-4 members of the group consisting of nitrogen, oxygen and sulfur;

wherein if B is substituted, it is substituted by one or more substituents selected from the group consisting of halogen, up to per-halo, and $W_n$, wherein n is 0-3 and each W is independently selected from the group consisting of —CN, —CO₂R⁷, —C(O)NR⁷R⁷, —C(O)R⁷, —NO₂, —OR⁷, —SR⁷, —NR⁷R⁷, —NR⁷C(O)OR⁷, —NR⁷C(O)R⁷, $C_1$-$C_{10}$ alkyl, $C_{2-10}$-alkenyl, $C_{1-10}$-alkoxy, $C_3$-$C_{10}$ cycloalkyl, $C_6$-$C_{14}$ aryl, $C_7$-$C_{24}$ alkaryl, $C_3$-$C_{13}$ heteroaryl, $C_4$-$C_{23}$ alkheteroaryl, substituted $C_1$-$C_{10}$ alkyl, substituted $C_{2-10}$-alkenyl, substituted $C_{1-10}$-alkoxy, substituted $C_3$-$C_{10}$ cycloalkyl, substituted $C_4$-$C_{23}$ alkheteroaryl and -Q-Ar;

wherein if W is a substituted group, it is substituted by one or more substituents independently selected from the group consisting of —CN, —CO₂R⁷, —C(O)NR⁷R⁷, —C(O)R⁷, —NO₂, —OR⁷, —SR⁷, —NR⁷R⁷, —NR⁷C(O)OR⁷, —NR⁷C(O)R⁷ and halogen up to per-halo;

wherein each R⁷ is independently selected from H, $C_1$-$C_{10}$ alkyl, $C_{2-10}$-alkenyl, $C_3$-$C_{10}$ cycloalkyl, $C_6$-$C_{14}$ aryl, $C_3$-$C_{13}$ heteroaryl, $C_7$-$C_{24}$ alkaryl, $C_4$-$C_{23}$ alkheteroaryl, up to per-halosubstituted $C_1$-$C_{10}$ alkyl, up to per-halosubstituted $C_{2-10}$-alkenyl, up to per-halosubstituted $C_3$-$C_{10}$ cycloalkyl, up to per-halosubstituted $C_6$-$C_{14}$ aryl and up to per-halosubstituted $C_3$-$C_{13}$ heteroaryl;

wherein Q is —O—, —S—, —N(R)$^7$, —(CH$_2$)-m, —C(O)—, —CH(OH)—, —NR$^7$C(O)NR$^7$R$^7$—NR$^7$C(O)—, —C(O)NR$^7$—, —(CH$_2$)$_m$O—, —(CH$_2$)$_m$S—, —(CH$_2$)$_m$N(R$^7$)—, —O(CH$_2$)$_m$—, CHX$^a$, —CX$^a$$_2$—, —S—(CH$_2$)$_m$— and —N(R$^7$)(CH$_2$)$_m$—, where m=1-3, and X$^a$ is halogen; and Ar is a 5-10 member aromatic structure containing 0-4 members of the group consisting of nitrogen, oxygen and sulfur, which is unsubstituted or substituted by halogen up to per-halosubstitution and optionally substituted by $Z_{n1}$, wherein n1 is 0 to 3 and each Z substituent is independently selected from the group consisting of —CN, —CO$_2$R$^7$, —C(O)NR$^7$R$^7$, —C(O)—NR$^7$, —NO$_2$, —OR$^7$, —SR$^7$, —NR$^7$R$^7$, —NR$^7$C(O)OR$^7$, —C(O)R$^7$, —NR$^7$C(O)R$^7$, C$_-$-C$_{10}$ alkyl, $C_3$-$C_{10}$ cycloalkyl, $C_6$-$C_{14}$ aryl, $C_3$-$C_{13}$ heteroaryl, $C_7$-$C_{24}$ alkaryl, $C_4$-$C_{23}$ alkheteroaryl, substituted $C_1$-$C_{10}$ alkyl, substituted $C_3$-$C_{10}$ cycloalkyl, substituted $C_7$-$C_{24}$ alkaryl and substituted $C_4$-$C_{23}$ alkheteroaryl; wherein the one or more substituents of Z are independently selected from the group consisting of —CN, —CO$_2$R$^7$, —C(O)NR$^7$R$^7$, —OR$^7$, —SR$^7$, —NO$_2$, —NR$^7$R$^7$, —NR$^7$C(O)R$^7$ and —NR$^7$C(O)OR$^7$;

or a pharmaceutically-acceptable salt thereof.

Exemplary compounds of these formulas include:
N-(5-tert-butyl-2-methoxyphenyl)-N'-(4-phenyloxyphenyl)urea;
N-(5-tert-butyl-2-methoxyphenyl)-N'-(4-(4-methoxyphenyloxy)phenyl)urea; N-(5-tert-butyl-2-methoxyphenyl)-N'-(4-(4-pyridinyloxy)phenyl)urea;
N-(5-tert-butyl-2-methoxyphenyl)-N'-(4-(4-pyridinylmethyl)phenyl)urea;
N-(5-tert-butyl-2-methoxyphenyl)-N'-(4-(4-pyridinylthio)phenyl)urea;
N-(5-tert-butyl-2-methoxyphenyl)-N'-(4-(4-(4,7-methano-H-isoindole-1,3 (2H)-dionyl)methyl)phenyl) urea;
N-(5-tert-butyl-2-phenylphenyl)-N'-(2,3-dichlorophenyl)urea;
N-(5-tert-butyl-2-(3-thienyl)phenyl)-N'-(2,3-dichlorophenyl)urea;
N-(5-tert-butyl-2-(N-methylaminocarbonyl)methoxyphenyl)-N'-(2,3-dichlorophenyl)urea;
N-(5-tert-butyl-2-(N-methylaminocarbonyl)methoxyphenyl)-N'-(1-naphthyl)urea;
N-(5-tert-butyl-2-(N-morpholinocarbonyl)methoxyphenyl)-N'-(2,3-dichlorophenyl)urea;
N-(5-tert-butyl-2-(N-morpholinocarbonyl)methoxyphenyl)-N'-(1-naphthyl)urea;
N-(5-tert-butyl-2-(3-tetrahydrofuranyloxy)phenyl)-N'-(2,3-dichlorophenyl)urea;
N-(5-tert-butyl-2-methoxyphenyl)-N'-(4-(3-pyridinyl)methylphenyl)urea;
N-(5-trifluoromethyl-2-methoxyphenyl)-N'-(4-methylphenyl)urea;
N-(5-trifluoromethyl-2-methoxyphenyl)-N'-(4-methyl-2-fluorophenyl)urea;
N-(5-trifluoromethyl-2-methoxyphenyl)-N'-(4-fluoro-3-chlorophenyl)urea;
N-(5-trifluoromethyl-2-methoxyphenyl)-N'-(4-methyl-3-chlorophenyl)urea;
N-(5-trifluoromethyl-2-methoxyphenyl)-N'-(4-methyl-3-fluorophenyl)urea;
N-(5-trifluoromethyl-2-methoxyphenyl)-N'-(2,4-difluorophenyl)urea;
N-(5-trifluoromethyl-2-methoxyphenyl)-N'-(4-phenyloxy-3,5-dichlorophenyl)urea;
N-(5-trifluoromethyl-2-methoxyphenyl)-N'-(4-(4-pyridinylmethyl)phenyl)urea;
N-(5-trifluoromethyl-2-methoxyphenyl)-N'-(4-(4-pyridinylthio)phenyl)urea;
N-(5-trifluoromethyl-2-methoxyphenyl)-N'-(4-(4-pyridinyloxy)phenyl)urea;
N-(5-trifluoromethyl-2-methoxyphenyl)-N'-(3-(4-pyridinylthio)phenyl)urea;
N-(5-trifluoromethyl-2-methoxyphenyl)-N'-(4-(3-(N-methylaminocarbonyl)phenyloxy)phenyl)urea;
N-(5-fluorosulfonyl)-2-methoxyphenyl)-N'-(4-methylphenyl)urea;
N-(5-(difluromethanesulfonyl)-2-methoxyphenyl)-N'-(4-methylphenyl)urea;
N-(5-(difluoromethanesulfonyl)-2-methoxyphenyl)-N'-(4-fluorophenyl)urea;
N-(5-(difluoromethanesulfonyl)-2-methoxyphenyl)-N'-(4-methyl-2-fluorophenyl)urea;
N-(5-(difluoromethanesulfonyl)-2-methoxyphenyl)-N'-(4-methyl-3-fluorophenyl)urea;
N-(5-(difluoromethanesulfonyl)-2-methoxyphenyl)-N'-(4-methyl-3-chlorophenyl)urea;
N-(5-(difluoromethanesulfonyl)-2-methoxyphenyl)-N'-(4-fluoro-3-chlorophenyl)urea;
N-(5-(difluoromethanesulfonyl)-2-methoxyphenyl)-N'-(4-fluoro-3-methylphenyl)urea;
N-(5-(difluoromethanesulfonyl)-2-methoxyphenyl)-N'-(2,3-dimethylphenyl)urea;
N-(5-(trifluoromethanesulfonyl)-2-methoxphenyl)-N'-(4-methylphenyl)urea;
N-(3-methoxy-2-naphthyl)-N'-(2-fluorophenyl)urea;
N-(3-methoxy-2-naphthyl)-N'-(4-methylphenyl)urea;
N-(3-methoxy-2-naphthyl)-N'-(3-fluorophenyl)urea;
N-(3-methoxy-2-naphthyl)-N'-(4-methyl-3-fluorophenyl)urea;
N-(3-methoxy-2-naphthyl)-N'-(2,3-dimethylphenyl)urea;
N-(3-methoxy-2-naphthyl)-N'-(1-naphthyl)urea;
N-(3-methoxy-2-naphthyl)-N'-(4-(4-pyridinylmethyl)phenyl)urea;
N-(3-methoxy-2-naphthyl)-N'-(4-(4-pyridinylthio)phenyl)urea;
N-(3-methoxy-2-naphthyl)-N'-(4-(4-methoxyphenyloxy)phenyl)urea;
N-(3-methoxy-2-naphthyl)-N'-(4-(4-(4,7-methano-1H-isoindole-1,3(2H)-dionyl)methyl)phenyl)urea;
N-(2-hydroxy-4-nitro-5-chlorophenyl)-N'-(phenyl)urea;
N-(2-hydroxy-4-nitro-5-chlorophenyl)-N'-(4-(4-pyridinylmethyl)phenyl)urea;

and pharmaceutically acceptable salts thereof.

Such compounds are described in published PCT applications WO 96/21452, WO 96/40143, WO 97/25046, WO 97/35856, WO 98/25619, WO 98/56377, WO 98/57966, WO 99/32110, WO 99/32121, WO 99/32463, WO 99/61440, WO 99/64400, WO 00/10563, WO 00/17204, WO 00/19824, WO 00/41698, WO 00/64422, WO 00/71535, WO 01/38324, WO 01/64679, WO 01/66539, and WO 01/66540, each of which is herein incorporated by reference.

In all instances herein where there is an alkenyl or alkynyl moiety as a substituent group, the unsaturated linkage, i.e., the vinylene or acetylene linkage, is preferably not directly attached to the nitrogen, oxygen or sulfur moieties, for instance in OR$_β$ or for certain R$_2$ moieties.

As used herein, "optionally substituted" unless specifically defined shall mean such groups as halogen, such as fluorine, chlorine, bromine or iodine; hydroxy; hydroxy-substituted $C_{1-10}$alkyl; $C_{1-10}$ alkoxy, such as methoxy or ethoxy; $S(O)_m$ alkyl, wherein m is 0, 1 or 2, such as methyl thio, methylsulfinyl or methyl sulfonyl; amino, mono and di-substituted amino, such as in the $NR_7R_{17}$ group; or where the $R_7R_{17}$ can together with the nitrogen to which they are attached cyclize to form a 5- to 7-membered ring which optionally includes an additional heteroatom selected from O, N, and S; $C_{1-10}$ alkyl, cycloalkyl, or cycloalkyl alkyl group, such as methyl, ethyl, propyl, isopropyl, t-butyl, etc. or cyclopropyl methyl; halo-substituted $C_{1-10}$ alkyl, such as $CF_3$; an optionally substituted aryl, such as phenyl, or an optionally substituted arylalkyl, such as benzyl or phenethyl, wherein these aryl moieties can also be substituted one to two times by halogen; hydroxy; hydroxy-substituted alkyl; $C_{1-10}$ alkoxy; $S(O)_m$ alkyl; amino, mono- and di-substituted amino, such as in the $NR_7R_{17}$ group; alkyl, or $CF_3$.

Inhibitors useful in the present invention can be used with any pharmaceutically acceptable salt. The term "pharmaceutically acceptable salts" refers to salts prepared from pharmaceutically acceptable non-toxic bases or acids. When the compound utilized by the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Basic salts of inorganic and organic acids also include as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically-acceptable salts of the above-described compounds can also be formed with a pharmaceutically-acceptable cation, for instance, if a substituent group comprises a carboxy moiety. Suitable pharmaceutically-acceptable cations are well known to those skilled in the art and include alkaline, alkaline earth, ammonium and quaternary ammonium cations.

Other pharmaceutically acceptable organic non-toxic bases from which salts can be formed include ion exchange resins such as, for example, arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

The inhibitors of p38 MAP kinase can be used as single therapeutic agents or in combination with other therapeutic agents. Drugs that could be usefully combined with these compounds include monoclonal antibodies targeting cells of the immune system, antibodies or soluble receptors or receptor fusion proteins targeting immune or non-immune cytokines, and small molecule inhibitors of cell division, protein synthesis, or mRNA transcription or translation, or inhibitors of immune cell differentiation, activation, or function (e.g., cytokine secretion).

The following terms, as used herein, refer to:

"halo" or "halogens", include the halogens: chloro, fluoro, bromo and iodo;

"$C_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like;

the term "cycloalkyl" is used herein to mean cyclic radicals, preferably of 3 to 8 carbons, including but not limited to cyclopropyl, cyclopentyl, cyclohexyl, and the like;

the term "cycloalkenyl" is used herein to mean cyclic radicals, preferably of 5 to 8 carbons, which have at least one double bond, including but not limited to cyclopentenyl, cyclohexenyl, and the like;

the term "alkenyl" is used herein at all occurrences to mean straight or branched chain radical of 2-10 carbon atoms, unless the chain length is limited thereto, wherein there is at least one double bond between two carbon atoms in the chain, including, but not limited to ethenyl, 1-propenyl, 2-propenyl, 2-methyl-1-propenyl, 1-butenyl, 2-butenyl and the like;

"aryl"—phenyl and naphthyl;

"heteroaryl" (on its own or in any combination, such as "heteroaryloxy" or "heteroaryl alkyl")—a 5-10-membered aromatic ring system in which one or more rings contain one or more heteroatoms selected from the group consisting of N, O and S, such as, but not limited, to pyrrole, pyrazole, furan, thiophene, quinoline, isoquinoline, quinazolinyl, pyridine, pyrimidine, oxazole, thiazole, thiadiazole, triazole, imidazole, or benzimidazole;

"heterocyclic" (on its own or in any combination, such as "heterocyclylalkyl")—a saturated or partially unsaturated 4-10-membered ring system in which one or more rings contain one or more heteroatoms selected from the group consisting of N, O, and S; such as, but not limited to, pyrrolidine, piperidine, piperazine, morpholine, tetrahydropyran, or imidazolidine;

the term "aralkyl" or "heteroarylalkyl" or "heterocyclicalkyl" is used herein to mean C!4 alkyl as defined above attached to an aryl, heteroaryl or heterocyclic moiety as also defined herein unless otherwise indicate;

"sulfinyl"—the oxide S(O) of the corresponding sulfide, the term "thio" refers to the sulfide, and the term "sulfonyl" refers to the fully oxidized $S(O)_2$ moiety;

"aroyl"—a C(O)Ar, wherein Ar is as phenyl, naphthyl, or aryl alkyl derivative such as defined above, such groups include but are not limited to benzyl and phenethyl; and "alkanoyl"—a $C(O)C_{1-10}$ alkyl wherein the alkyl is as defined above.

For the purposes herein the "core" 4-pyrimidinyl moiety for $R_1$ or $R_2$ is referred to as the formula:

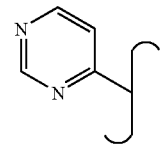

The compounds useful in the practice of the present invention can contain one or more asymmetric carbon atoms and can exist in racemic and optically active forms. The use of all of these compounds are included within the scope of the present invention.

Compounds useful in the practice of the present invention also include, but are not limited to, the compounds shown in Tables A-C, below.

TABLE A

| Chemical Structure | Citations, each of which is herein incorporated by reference. |
|---|---|
| 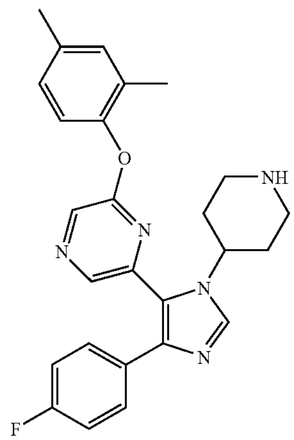 | WO-00166539, WO-00166540, WO-00164679, WO-00138324, WO-00064422, WO-00019824, WO-00010563, WO-09961440, WO-09932121, WO-09857966, WO-09856377, WO-09825619, WO-05756499, WO-09735856, WO-09725046, WO-09640143, WO-09621452; Gallagher, T. F., et. Al., Bioorg. Med. Chem. 5:49 (1997); Adams, J. L., et al., Bioorg. Med. Chem. Lett. 8:3111–3116 (1998) |
| 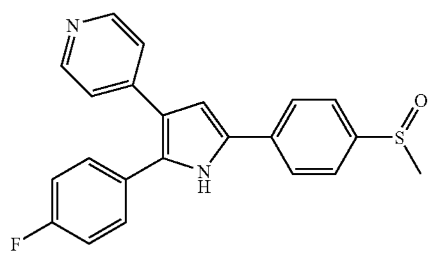 | De Laszlo, S. E., et. Al., Bioorg Med Chem Lett. 8:2698 (1998) |
| 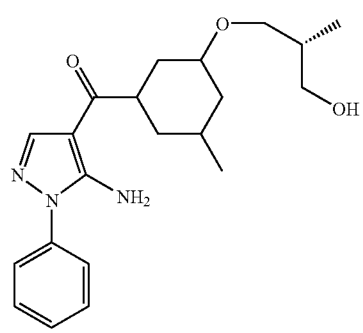 | WO-09957101; Poster presentation at the 5$^{th}$ World Congress on Inflammation, Edinburgh, UK. (2001) |
| 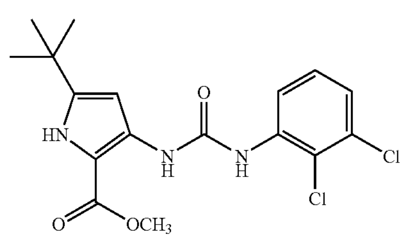 | WO-00041698, WO-09932110, WO-09932463 |

TABLE A-continued

| Chemical Structure | Citations, each of which is herein incorporated by reference. |
| --- | --- |
| (structure) | WO-00017204, WO-09964400 |
| (structure) | Revesz. L., et. al., Bioorg Med Chem Lett. 10:1261 (2000) |
| (structure) | WO-00207772 |
| (structure) | Fijen, J. W., et al., Clin. Exp. Immunol. 124:16–20 (2001); Wadsworth, S. A., et. al., J. Pharmacol. Expt. Therapeut. 291:680 (1999) |
| (structure) | Collis, A. J., et al.. Bioorg. Med. Chem. Lett. 11:693–696 (2001); McLay, L. M., et al., Bioorg Med Chem 9:537–554 (2001) |

TABLE A-continued
| Chemical Structure | Citations, each of which is herein incorporated by reference. |
|---|---|
| 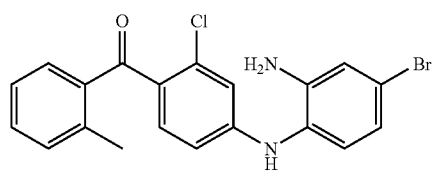 | WO-00110865, WO-00105749 |
TABLE B
| Compd. # | STRUCTURE |
|---|---|
| 1 | 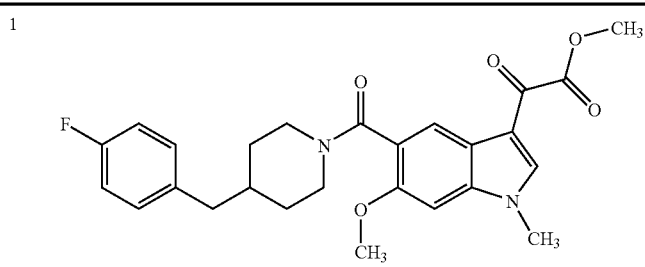 |
| 2 | 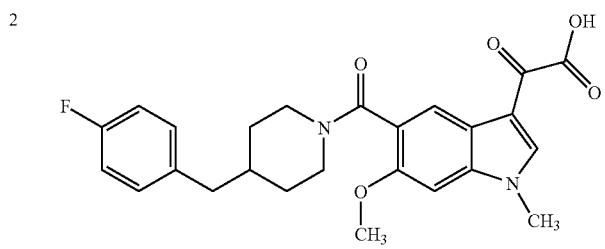 |
| 3 | 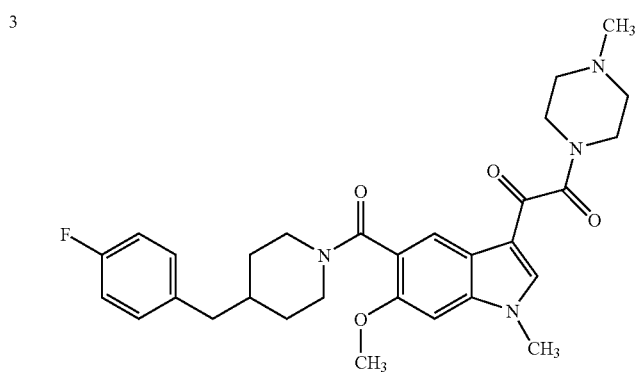 |
| 4 | 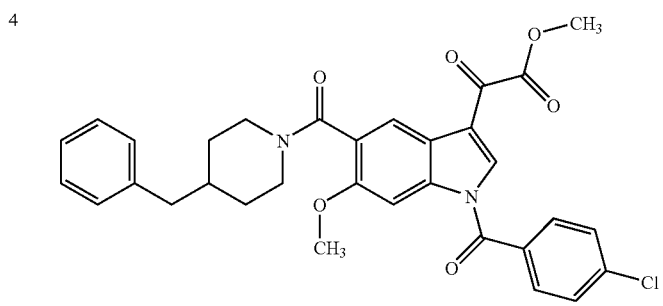 |

TABLE B-continued
5
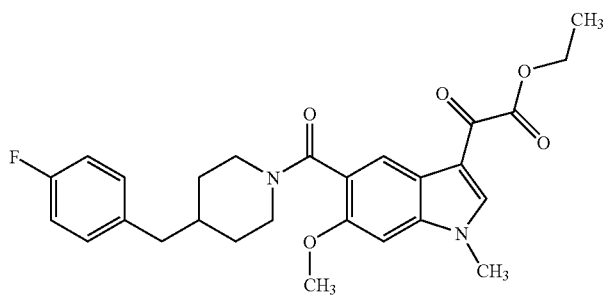
6
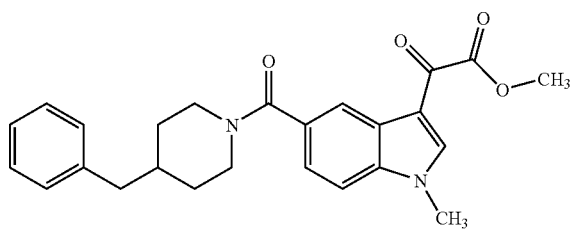
7
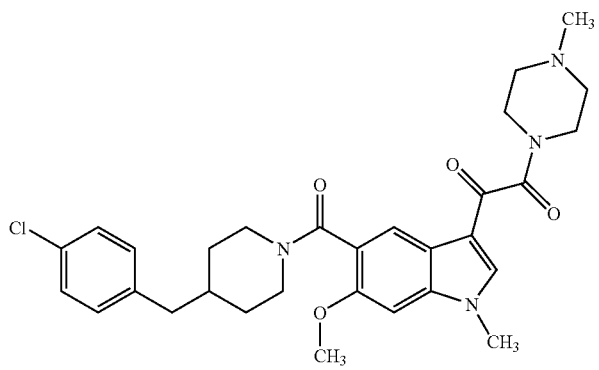
8
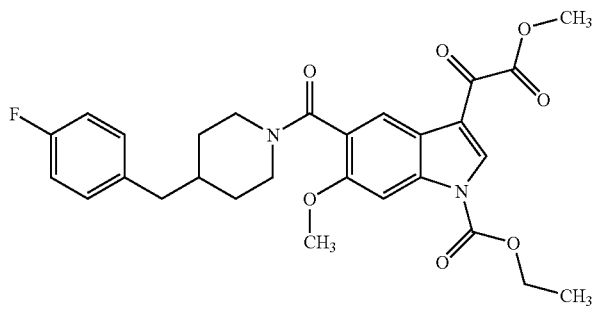

TABLE B-continued
9
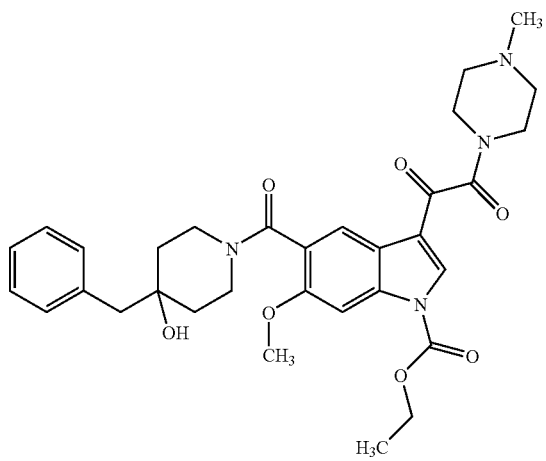
10
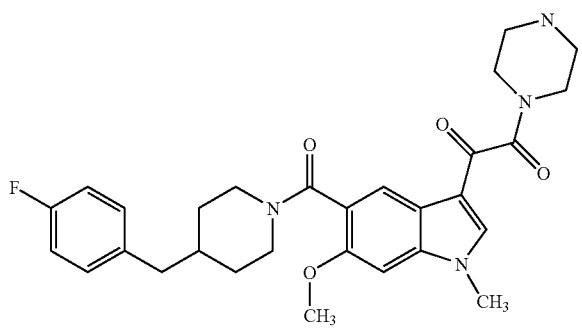
11
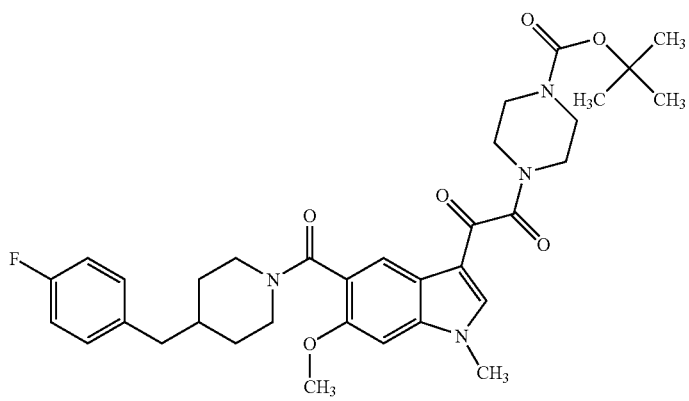
12
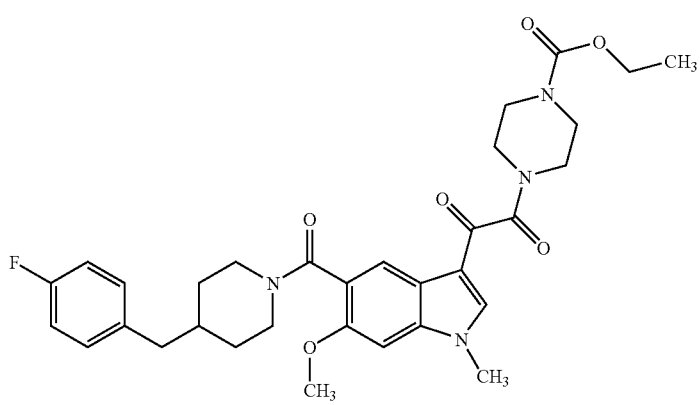

TABLE B-continued
13 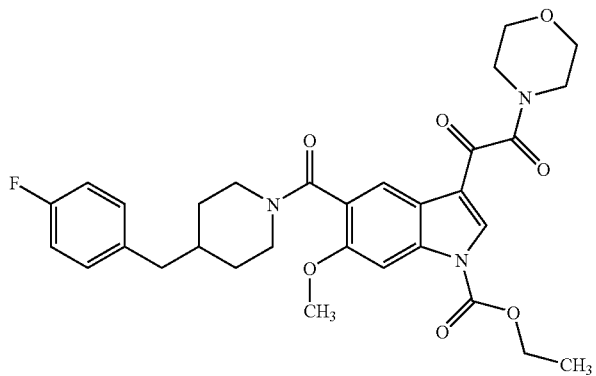
14 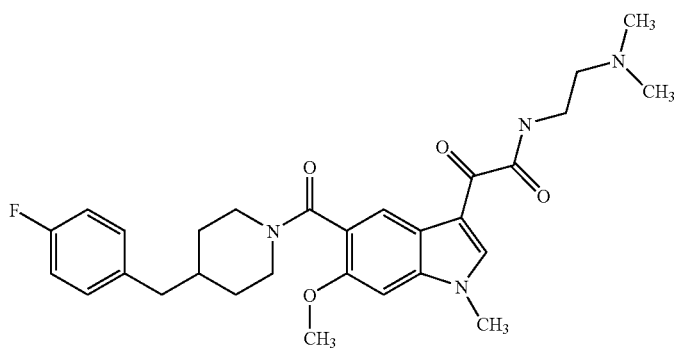
15 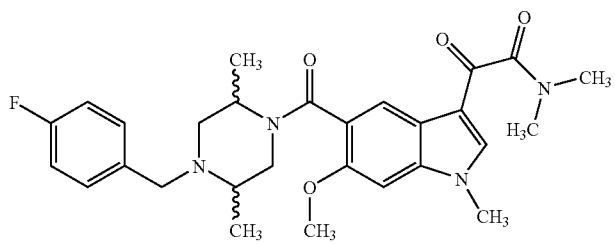
16 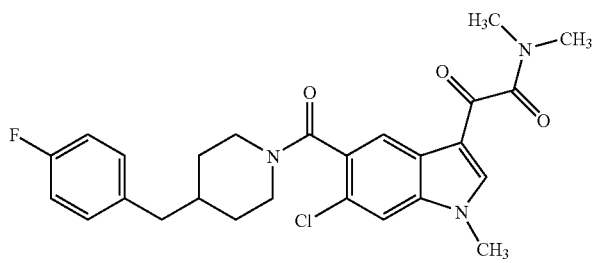
17 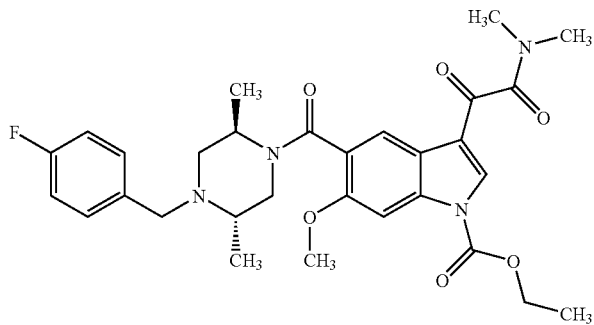

TABLE B-continued
| 18 | 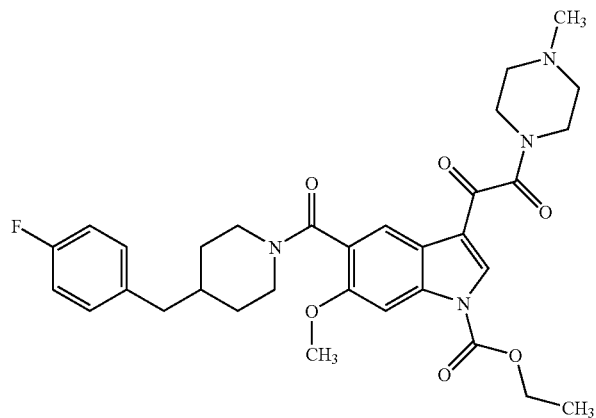 |
| 19 | 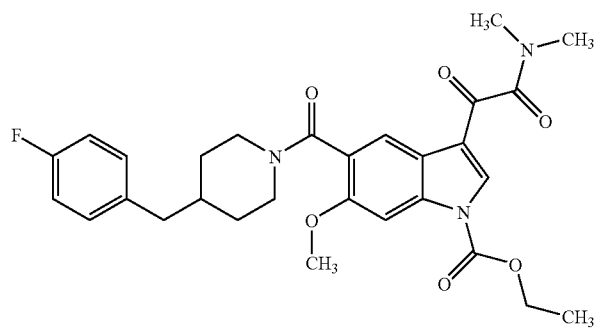 |
| 20 | 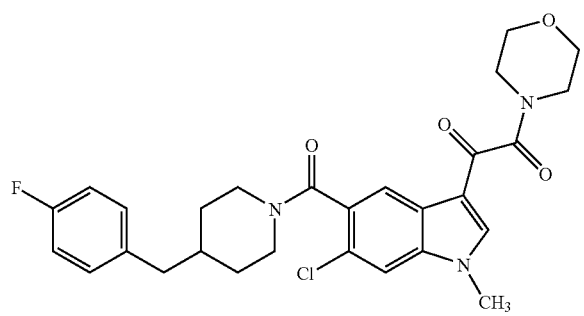 |
| 21 | 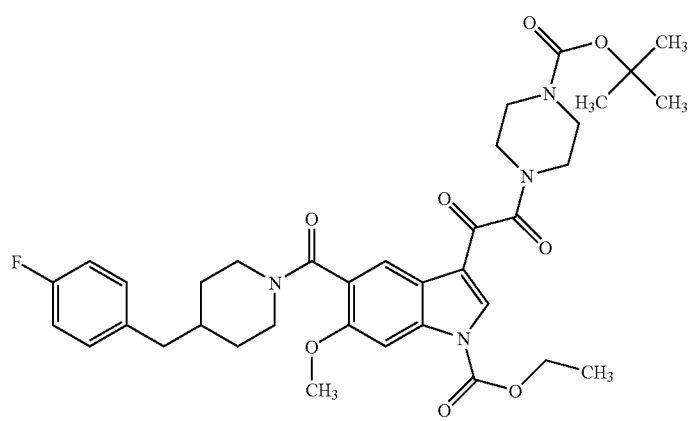 |

TABLE B-continued
22
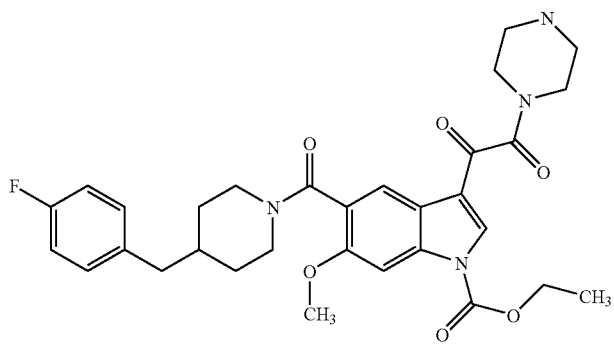
23
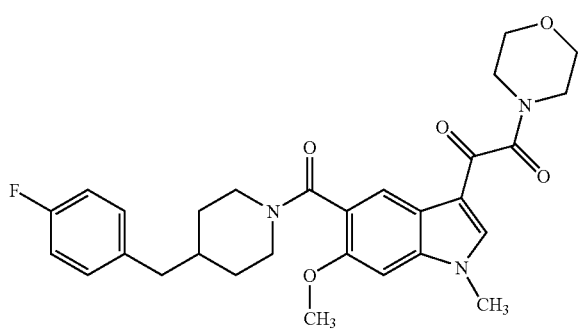
24
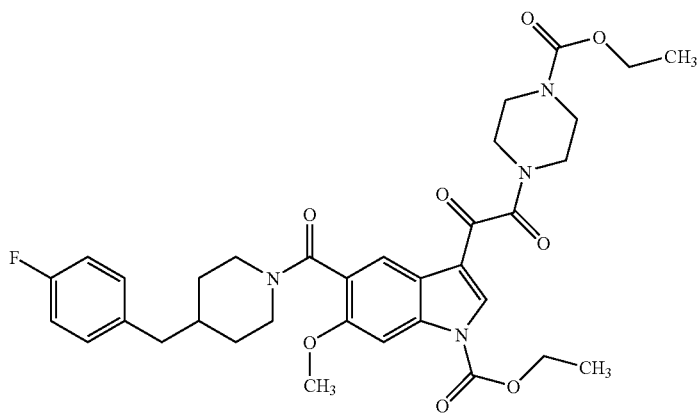
25
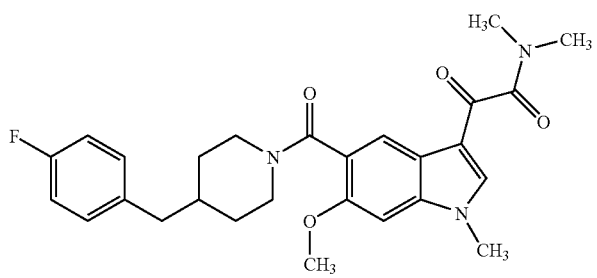

TABLE B-continued
26 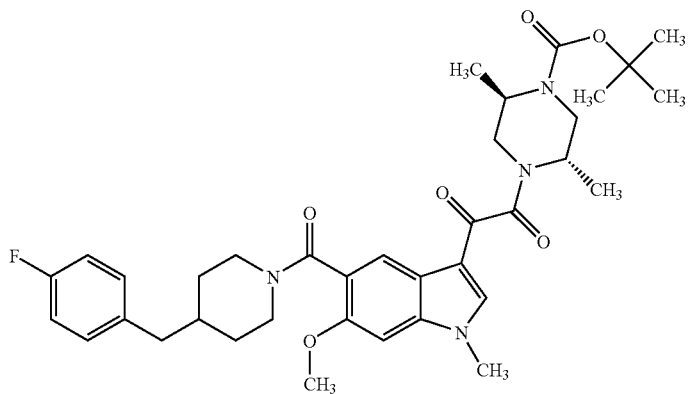
27 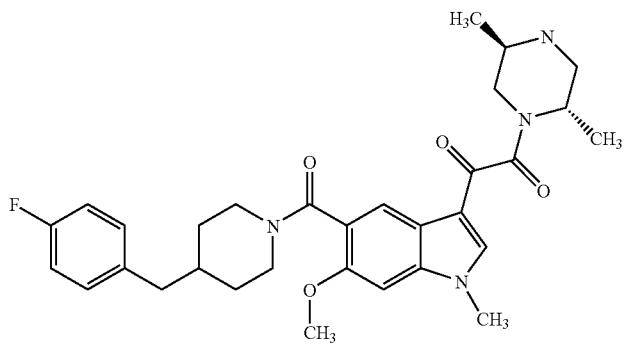
28 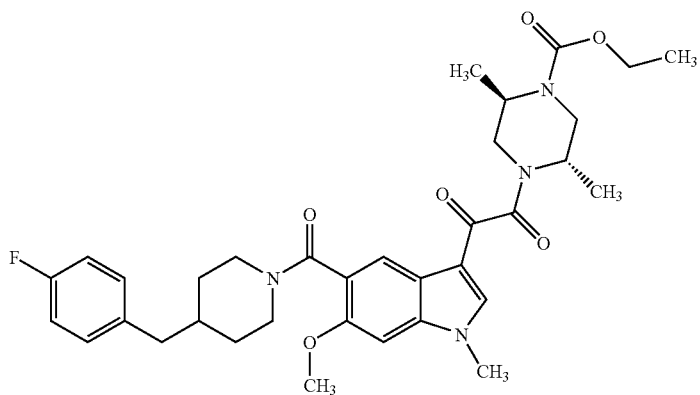
29 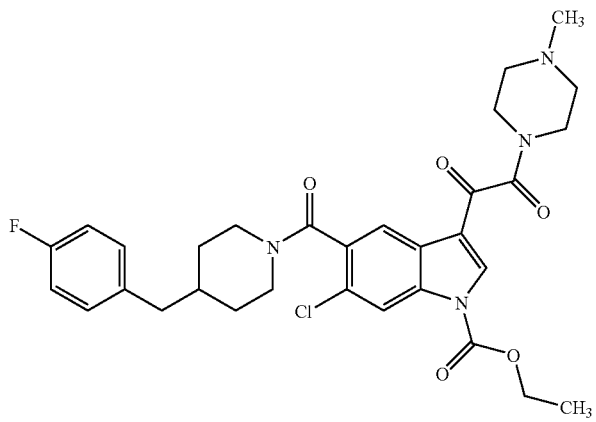

TABLE B-continued
30
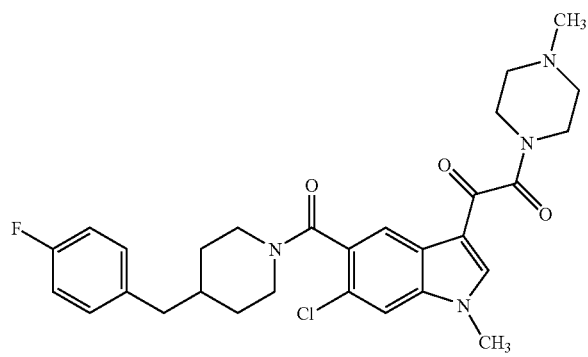
31
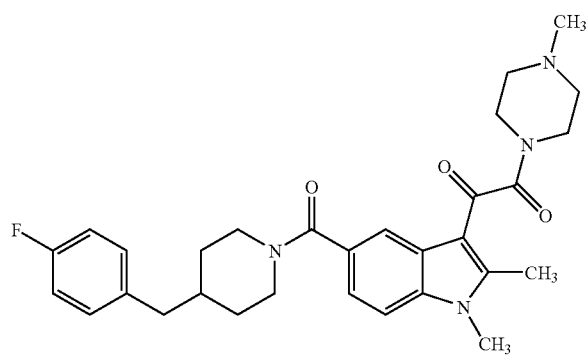
32
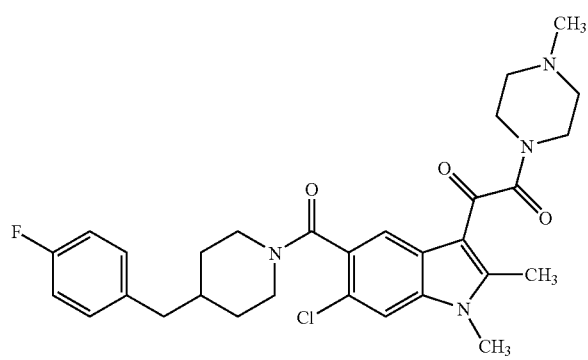
33
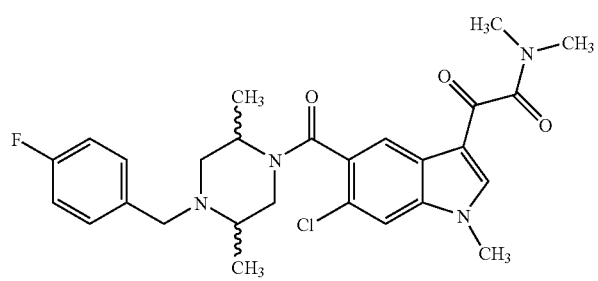

TABLE B-continued
34
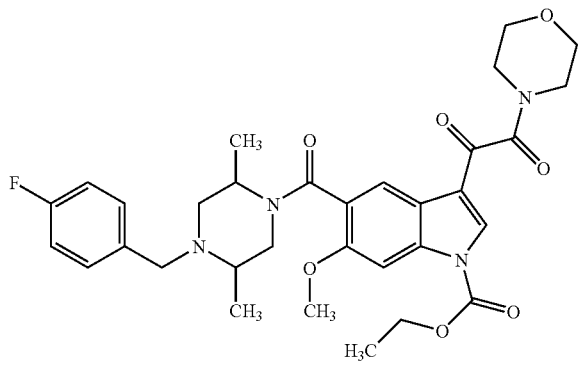
35
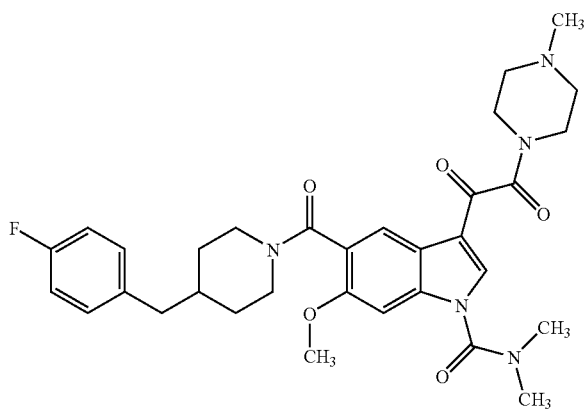
36
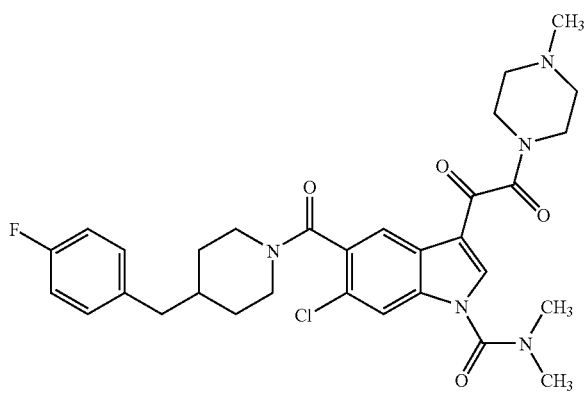
37
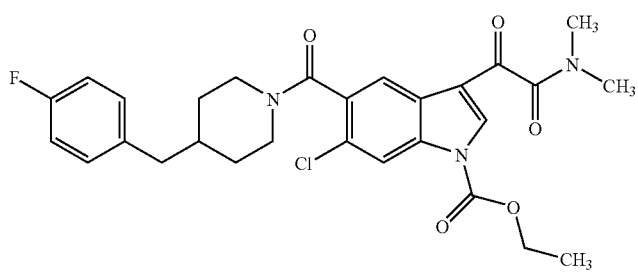

TABLE B-continued
| | |
|---|---|
| 38 | 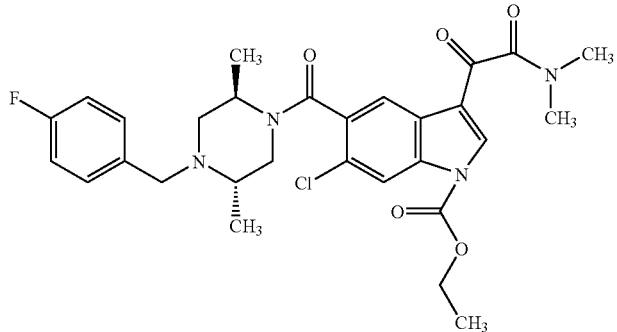 |
| 39 | 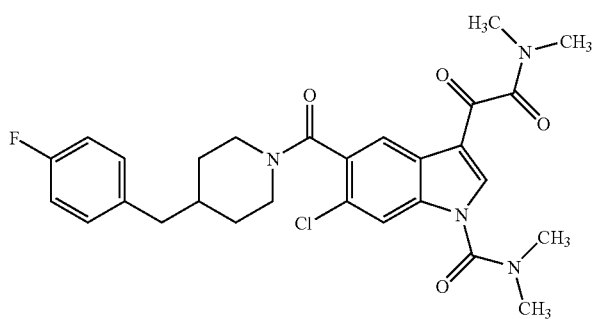 |
| 40 | 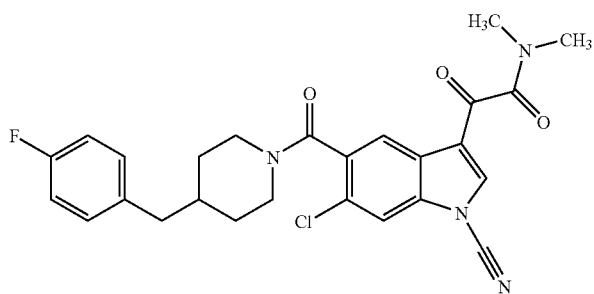 |
| 41 | 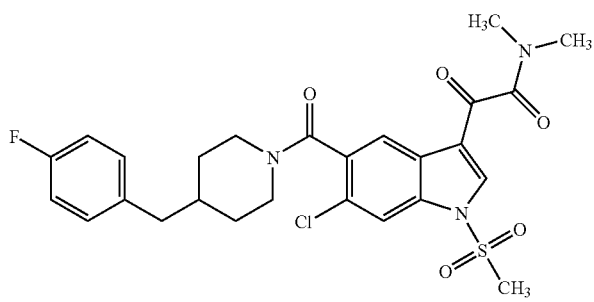 |
| 42 | 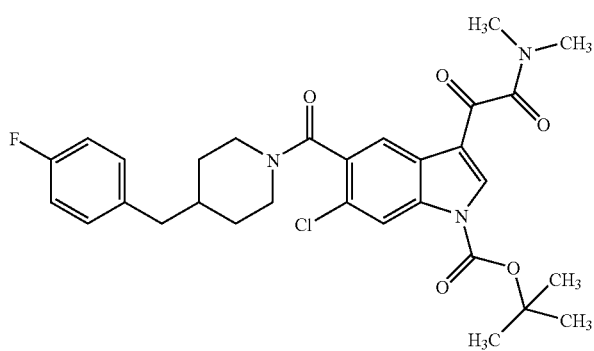 |

TABLE B-continued
43 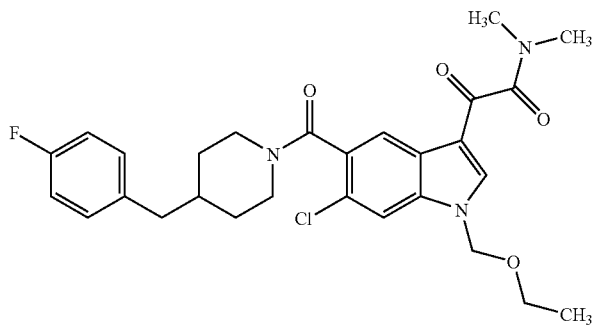
44 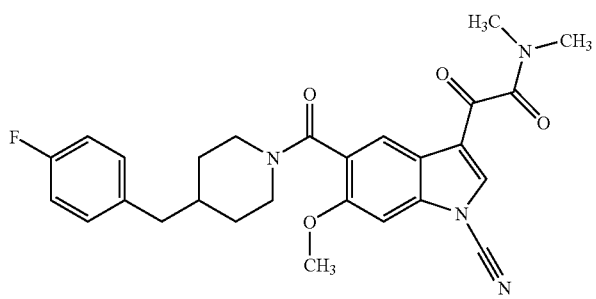
45 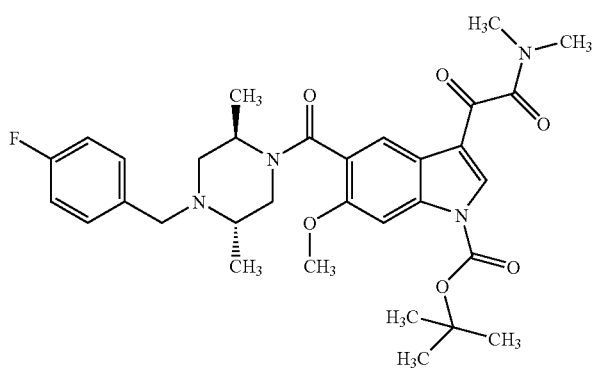
46 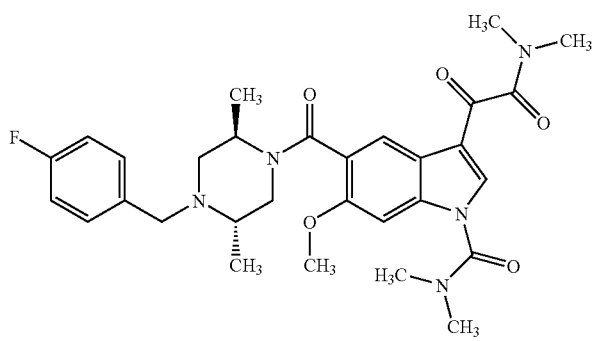
47 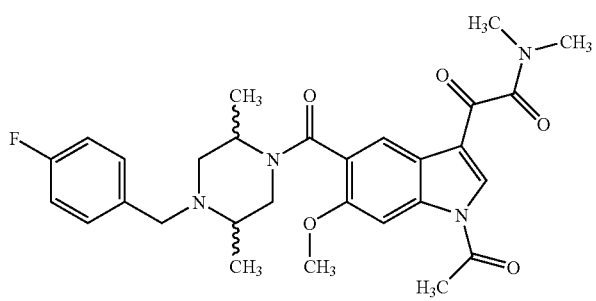

TABLE B-continued
48 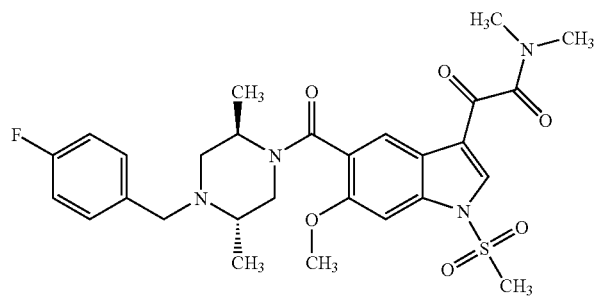
49 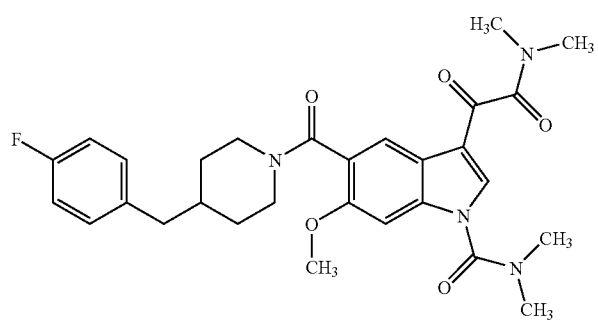
50 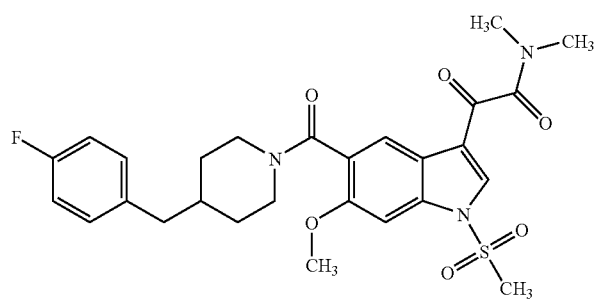
51 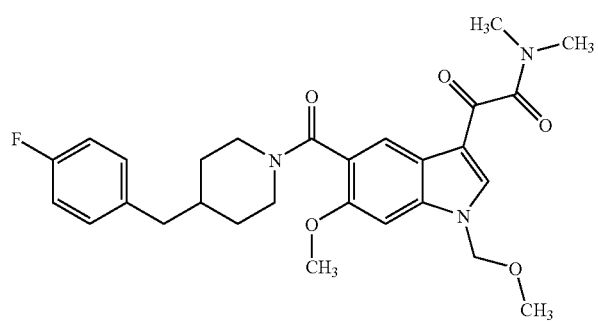
52 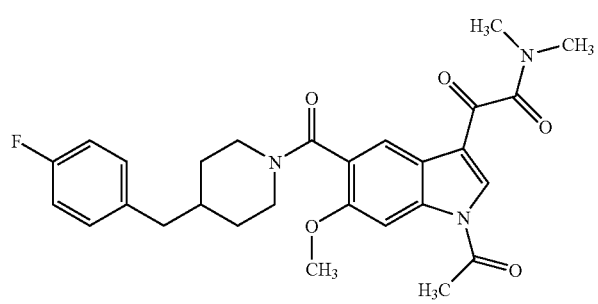

TABLE B-continued
| 53 | 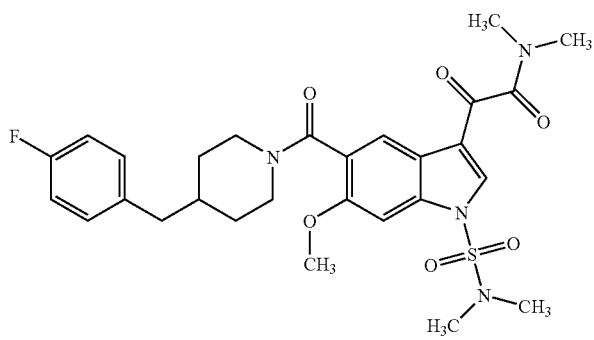 |
| --- | --- |
| 54 | 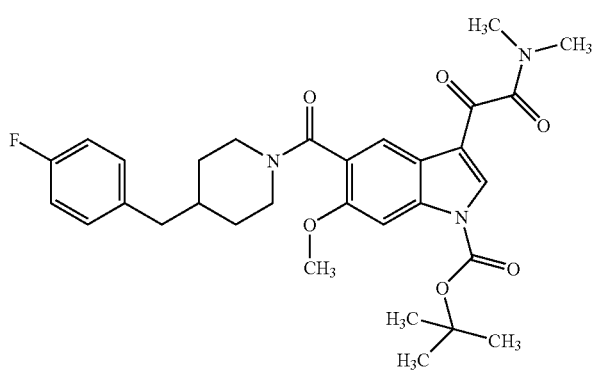 |
| 55 | 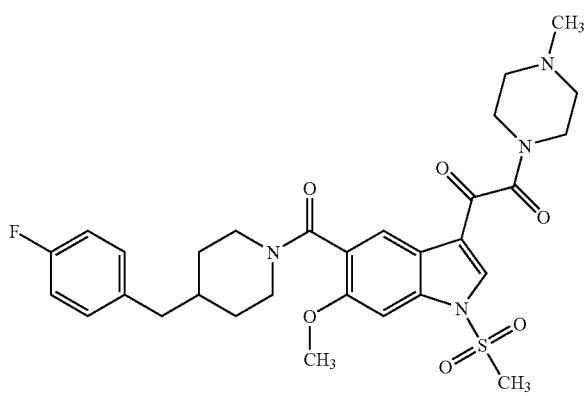 |
| 56 | 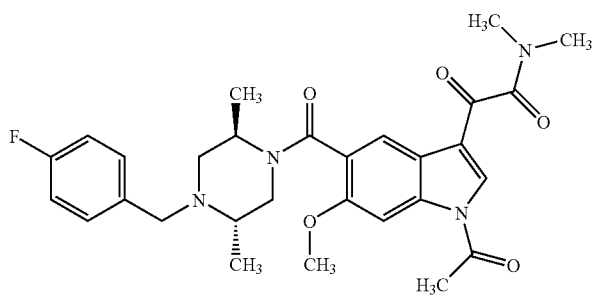 |

TABLE B-continued
| 57 | 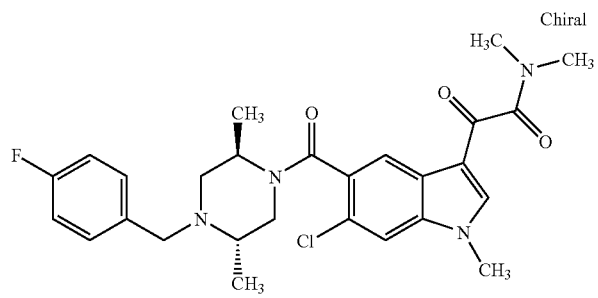 |
| 58 | 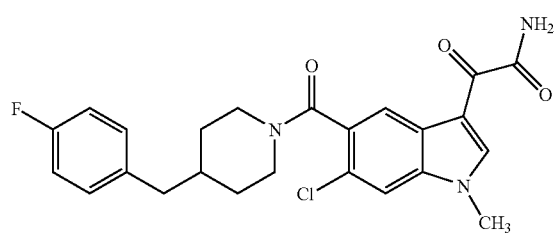 |
| 59 | 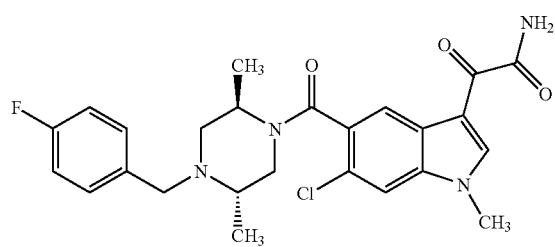 |
| 60 | 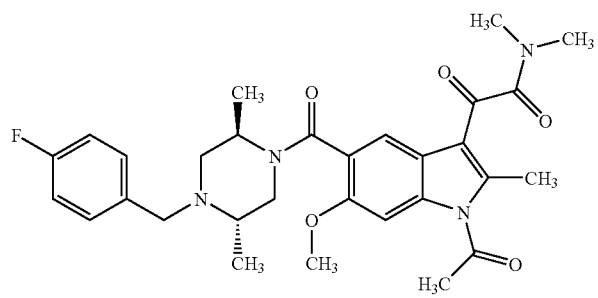 |
| 61 | 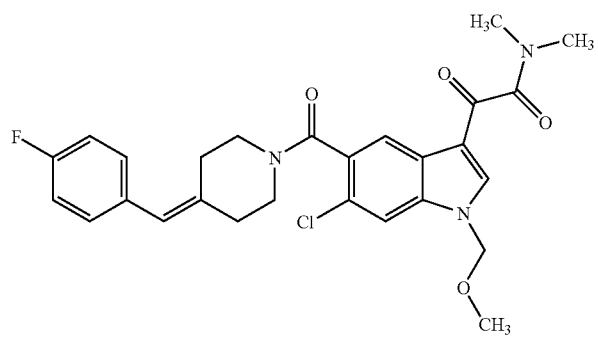 |

TABLE B-continued
62
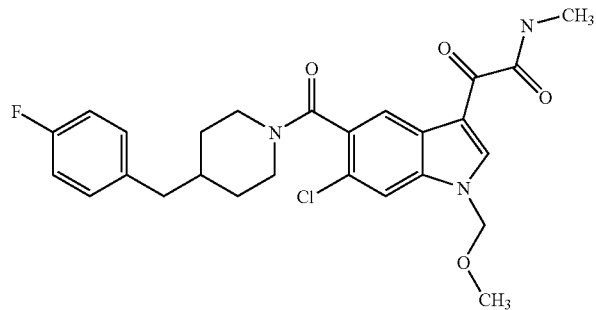
63
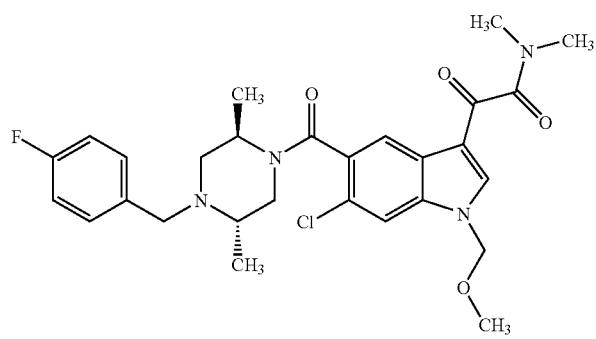
64
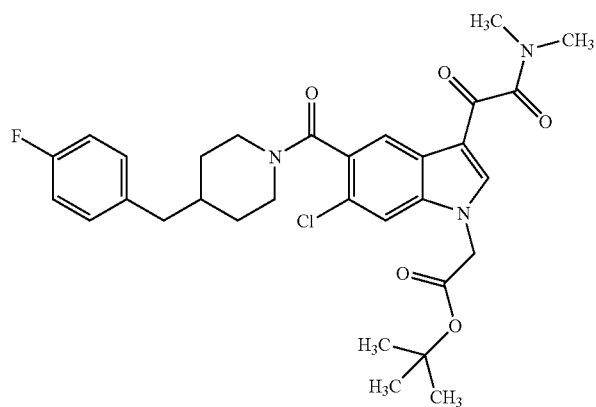
65
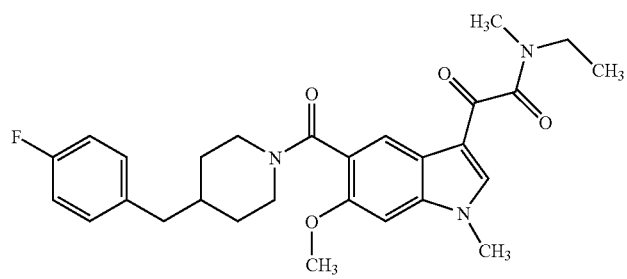

TABLE B-continued
66 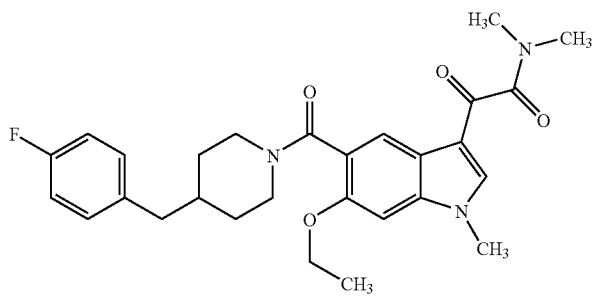
67 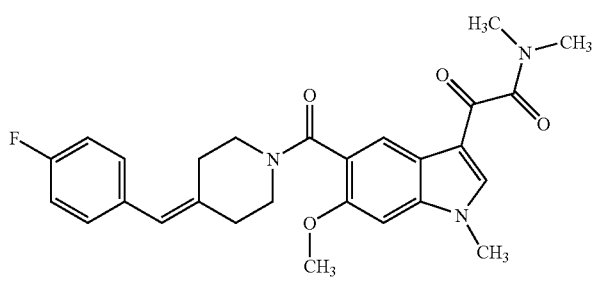
68 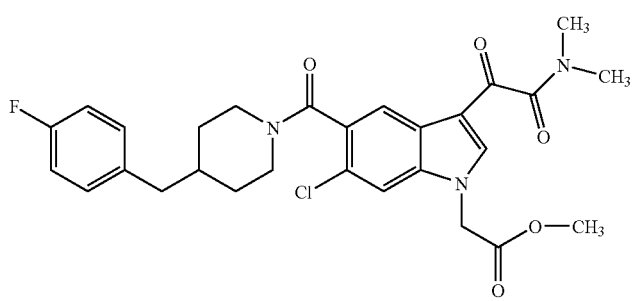
69 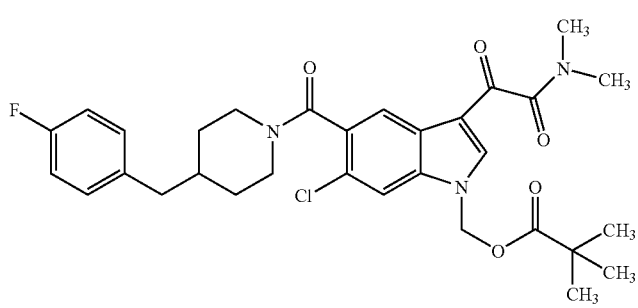
70 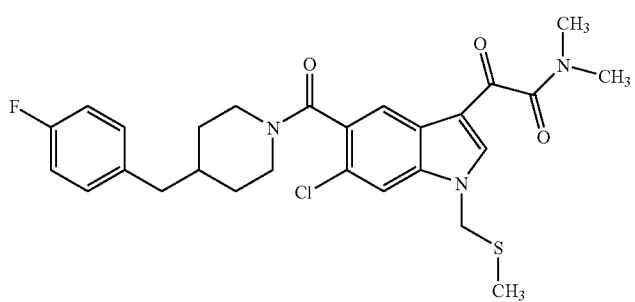

TABLE B-continued
71 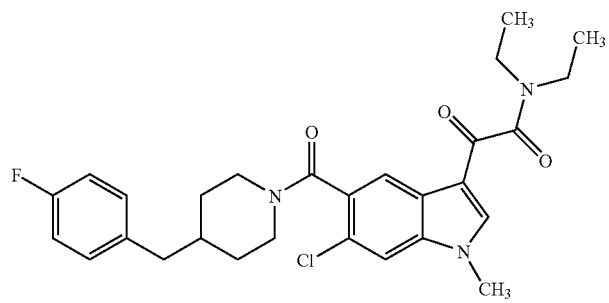
72 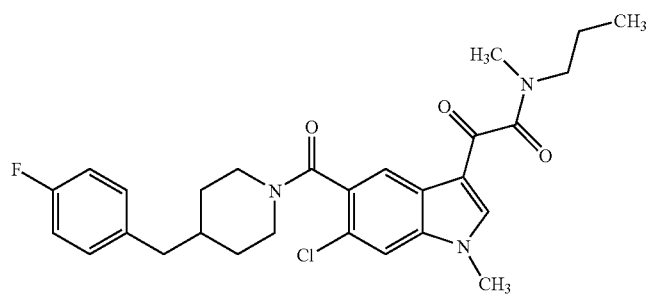
73 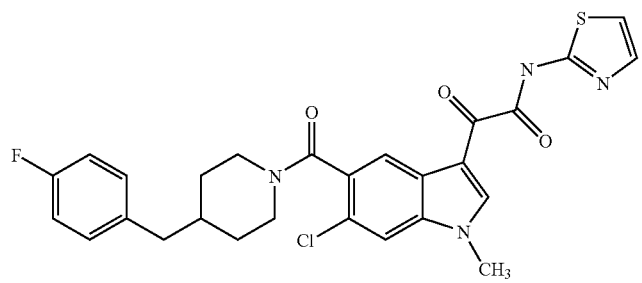
74 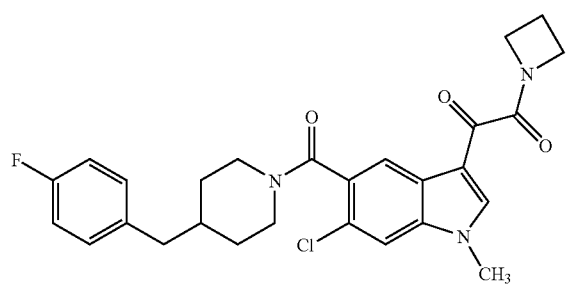
75 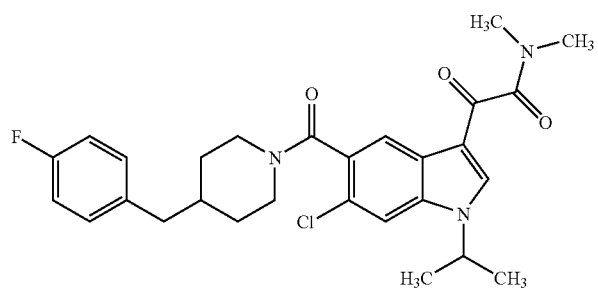

TABLE B-continued
76 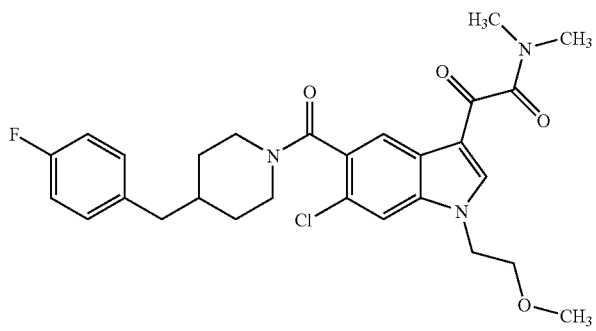
77 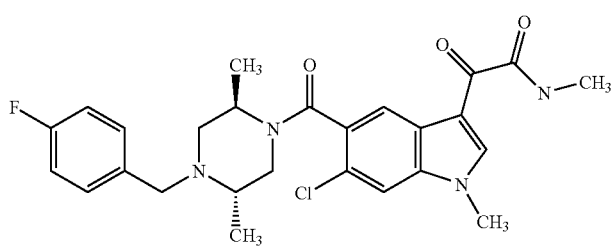
78 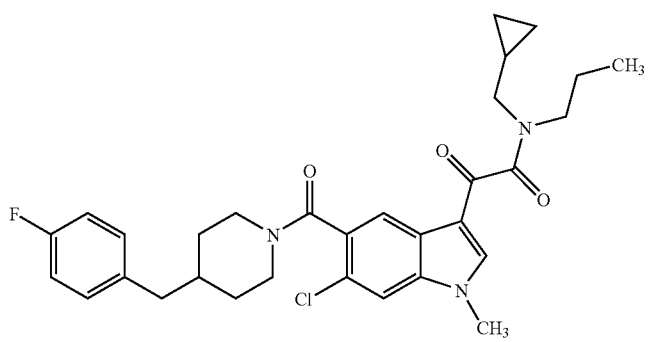
79 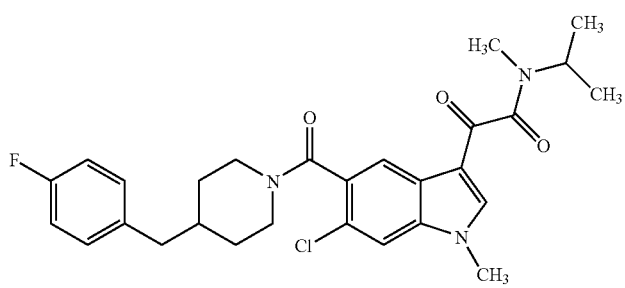
80 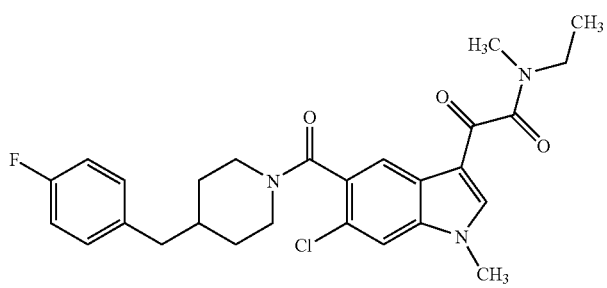

TABLE B-continued
81 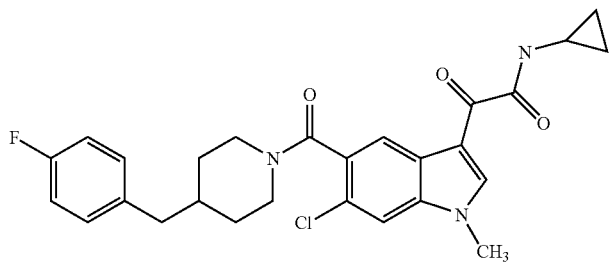
82 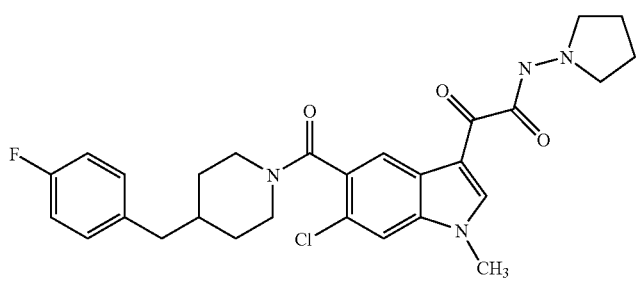
83 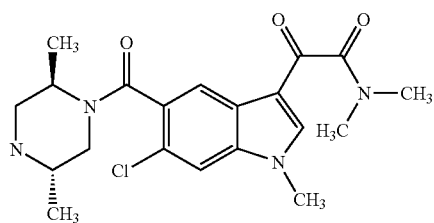
84 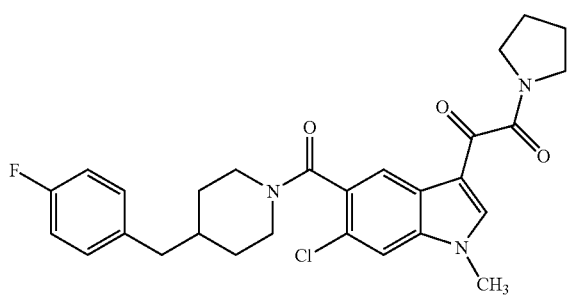
85 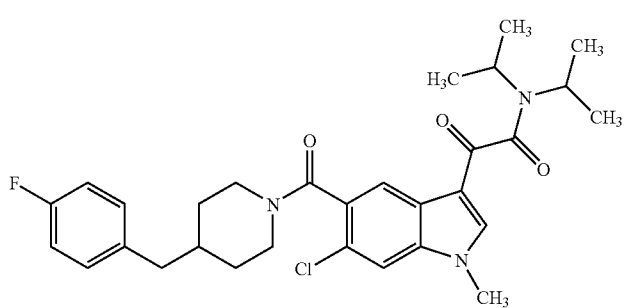

TABLE B-continued
86 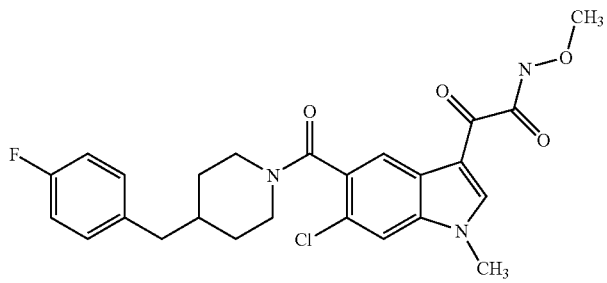
87 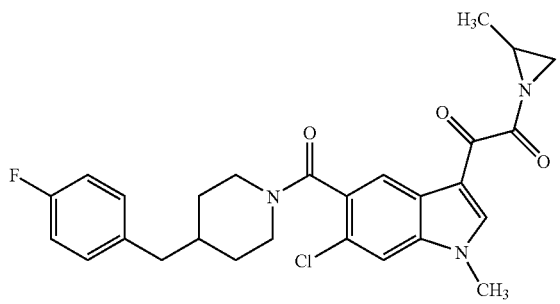
88 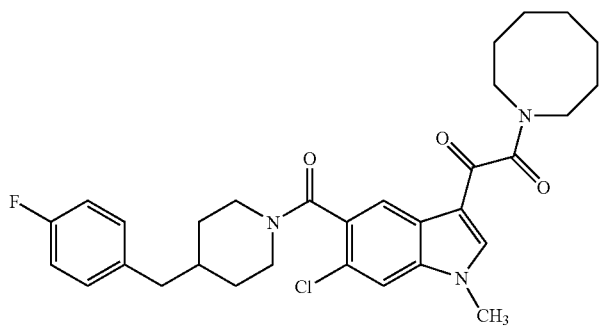
89 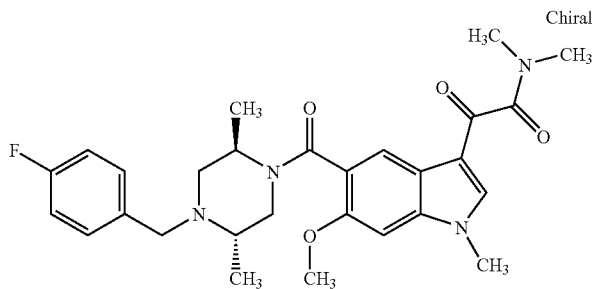
90 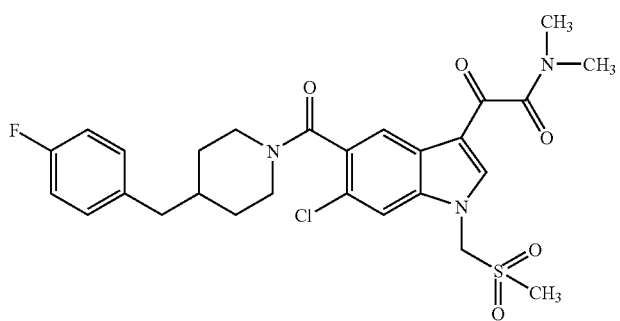

TABLE B-continued
| 91 | 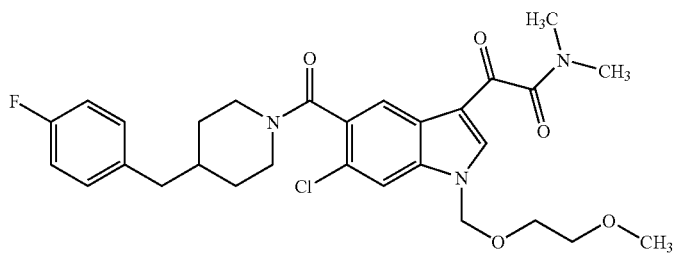 |
| --- | --- |
| 92 | 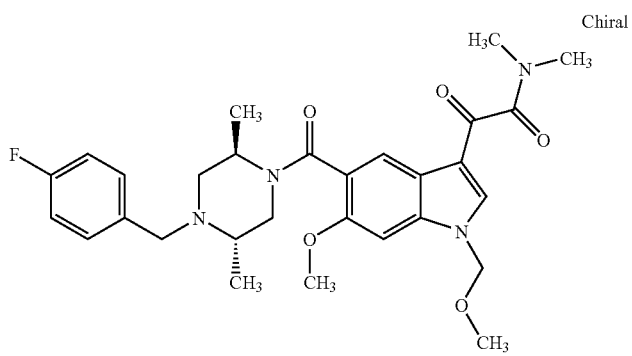 Chiral |
| 93 | 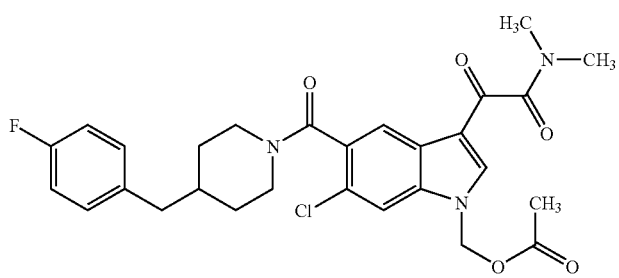 |
| 94 | 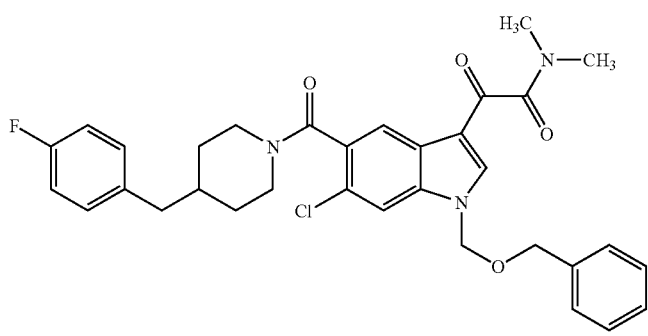 |
| 95 | 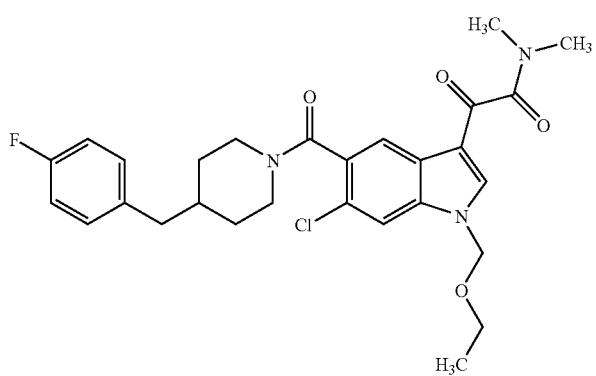 |

TABLE B-continued
96 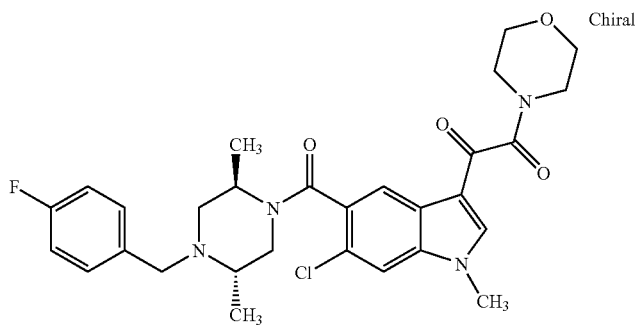
97 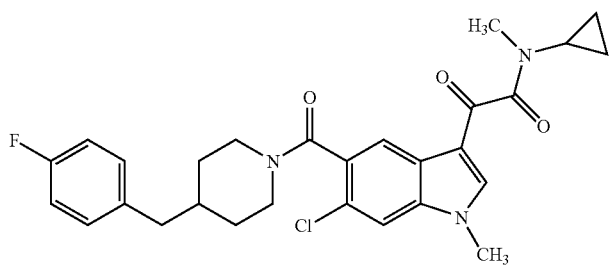
98 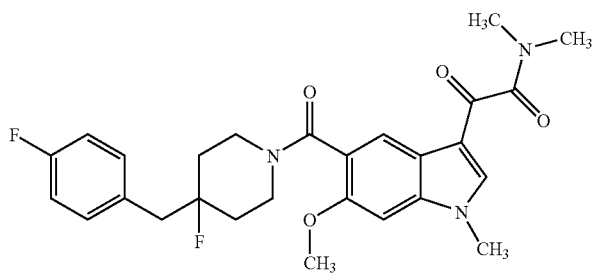
99 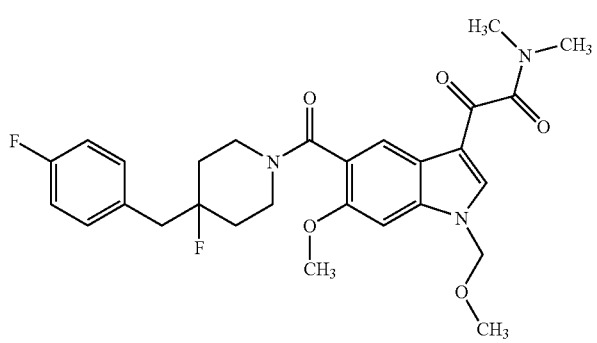
100 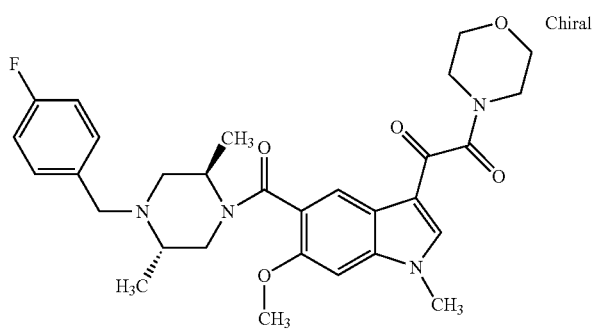

TABLE B-continued
101 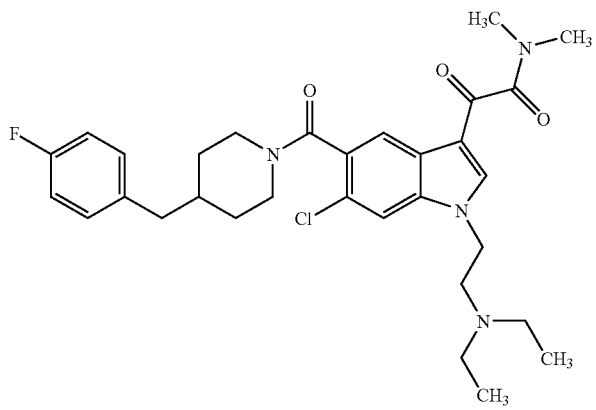
102 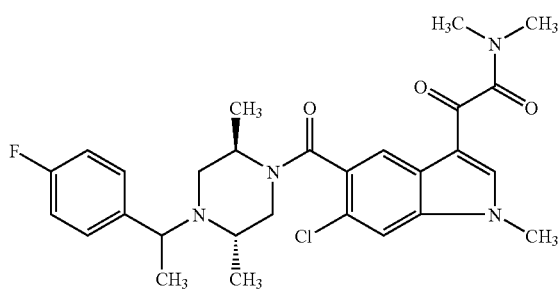
103 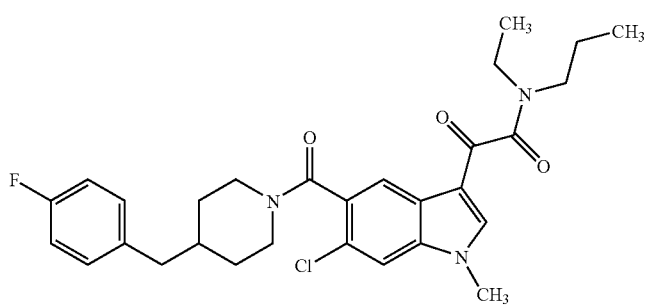
104 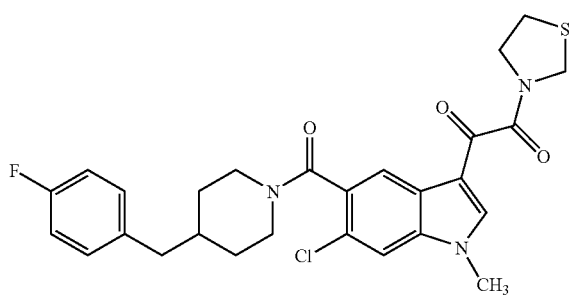
105 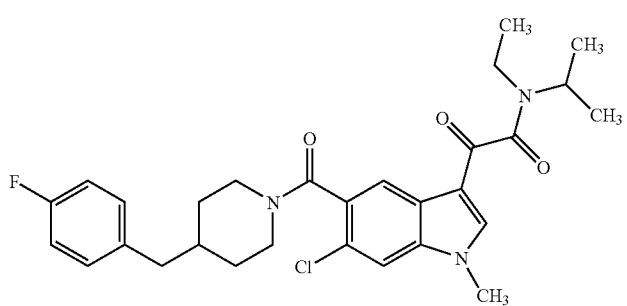

TABLE B-continued
106 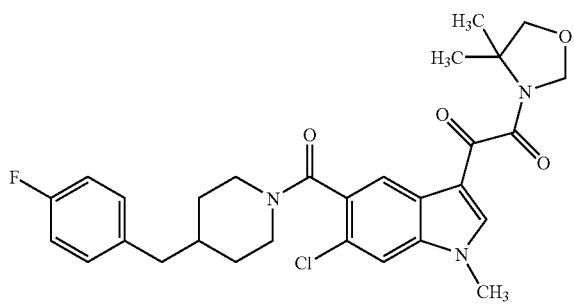
107 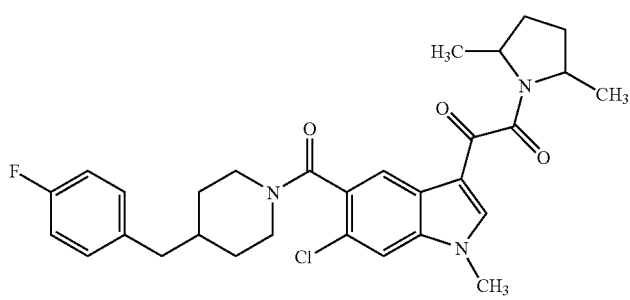
108 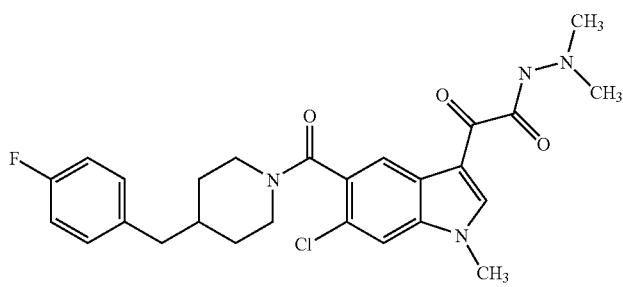
109 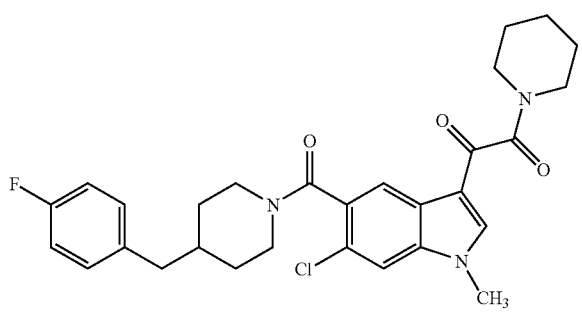
110 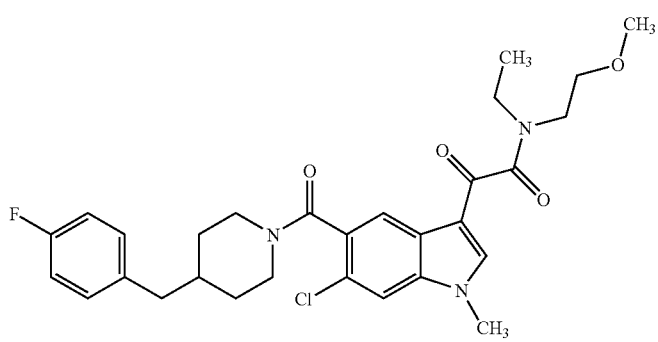

TABLE B-continued
111 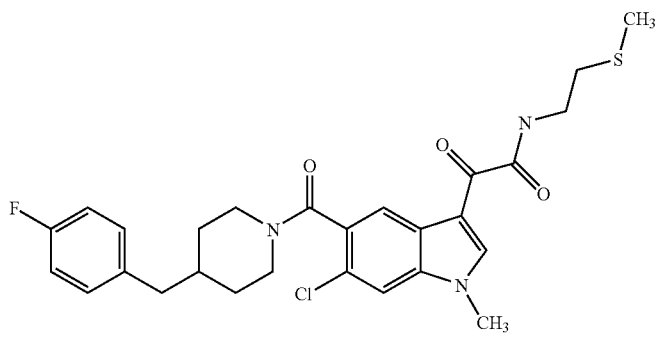
112 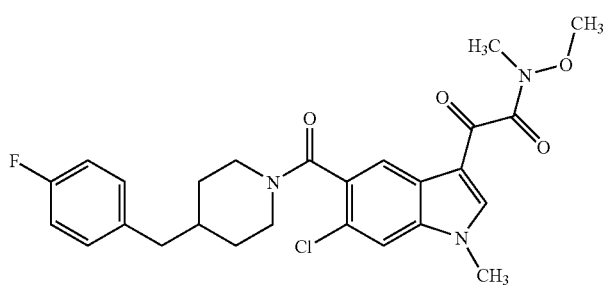
113 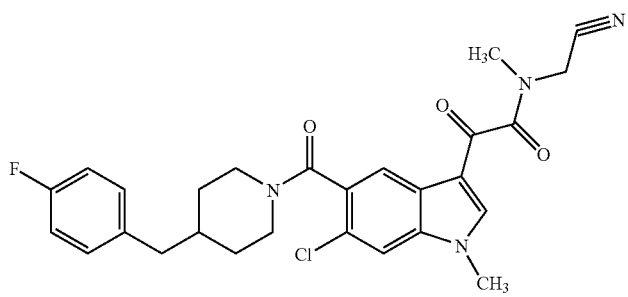
114 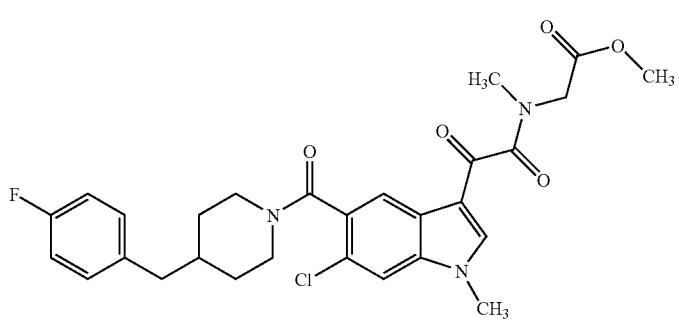
115 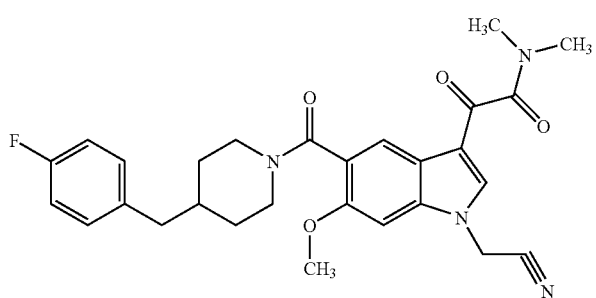

TABLE B-continued
| 116 | 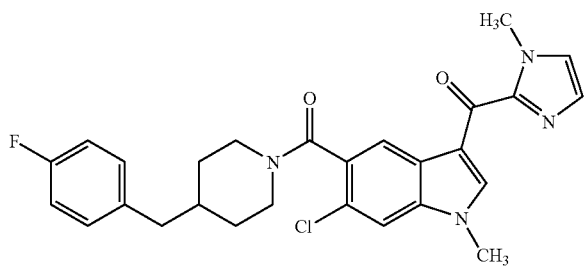 |
| Compd.# | MOLSTRUCTURE |
|---|---|
| 117 | 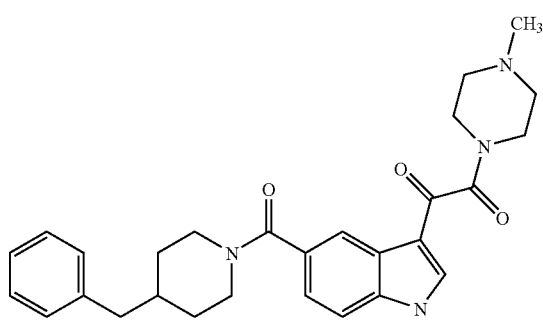 |
| 118 | 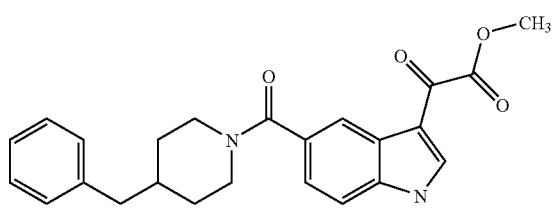 |
| 119 | 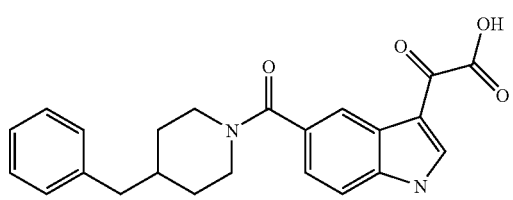 |
| 120 | 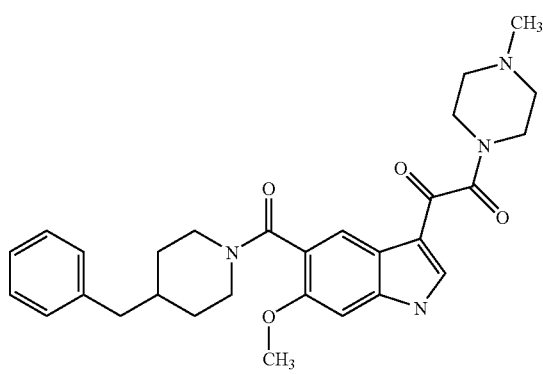 |

TABLE B-continued
121 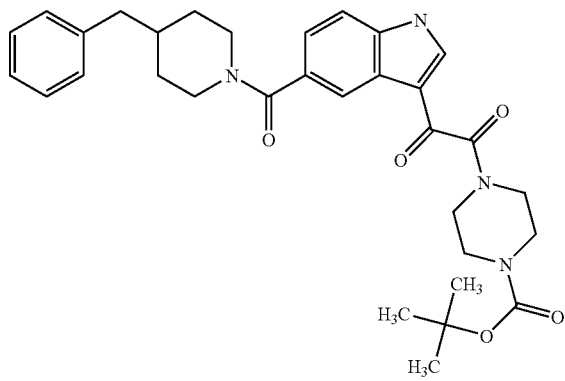
122 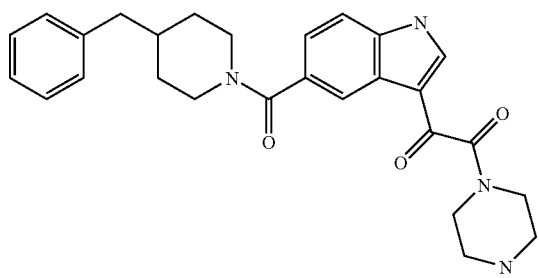
123 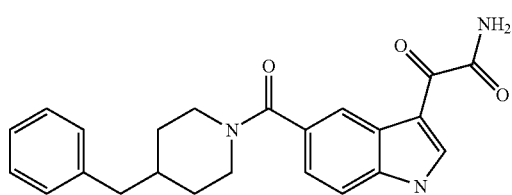
124 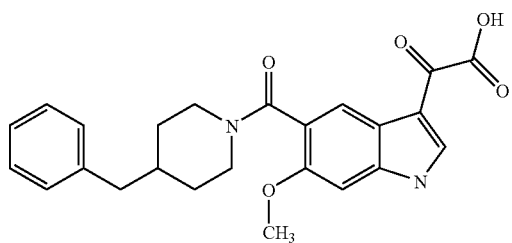
125 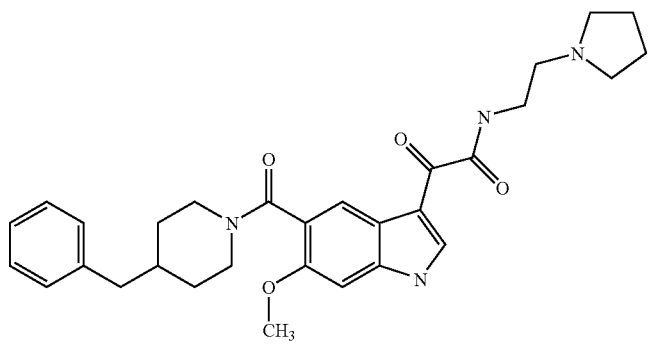

TABLE B-continued
| 126 | 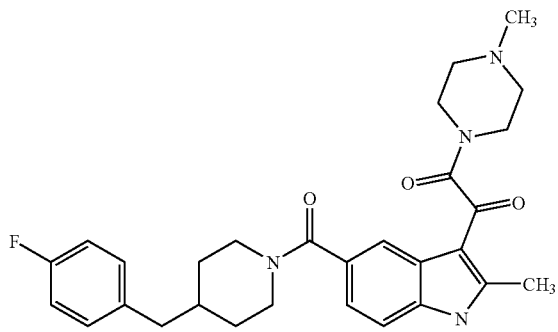 |
| 127 | 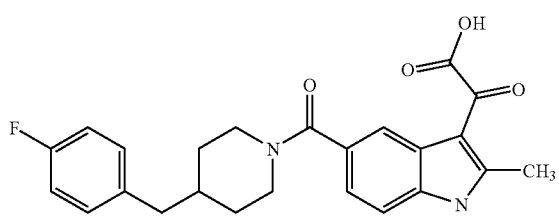 |
| 128 | 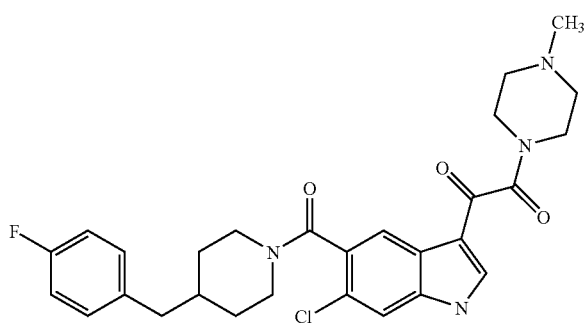 |
| 129 | 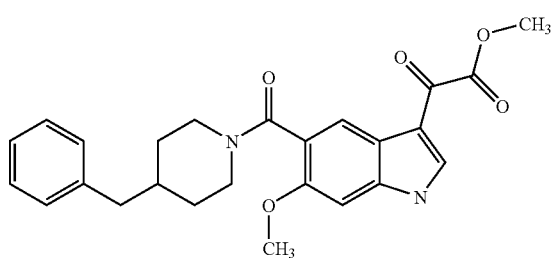 |
| 130 | 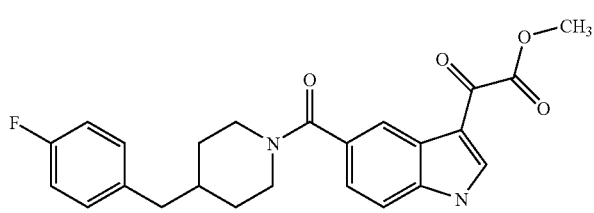 |
| 131 | 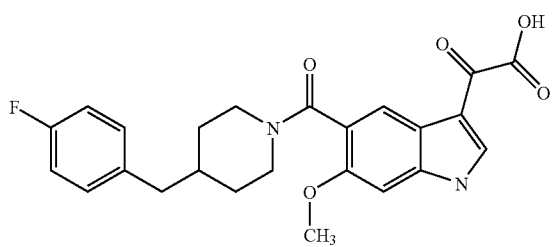 |

TABLE B-continued
132 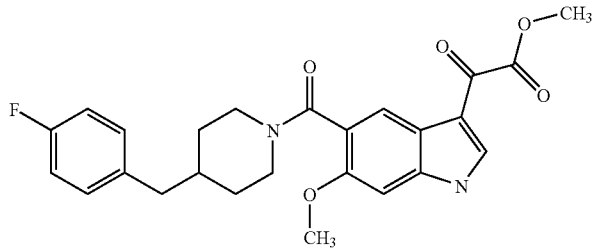
133 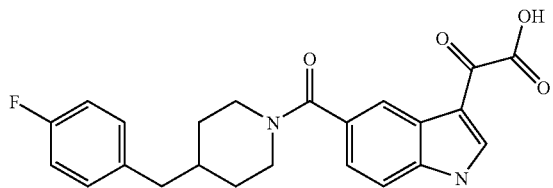
134 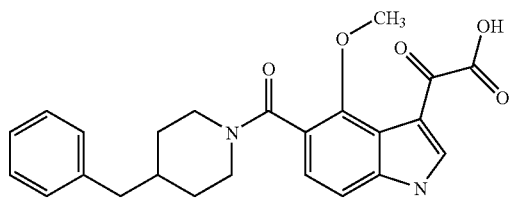
135 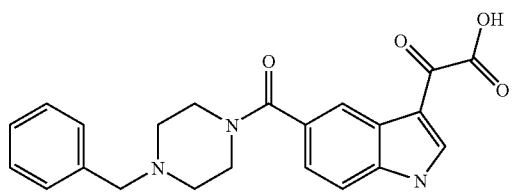
136 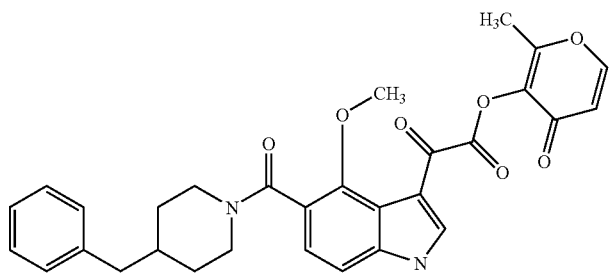
137 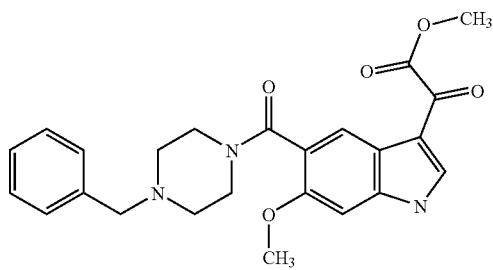

TABLE B-continued
138 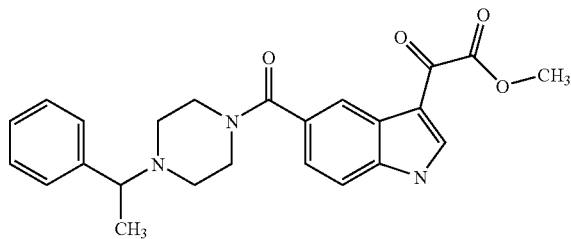
139 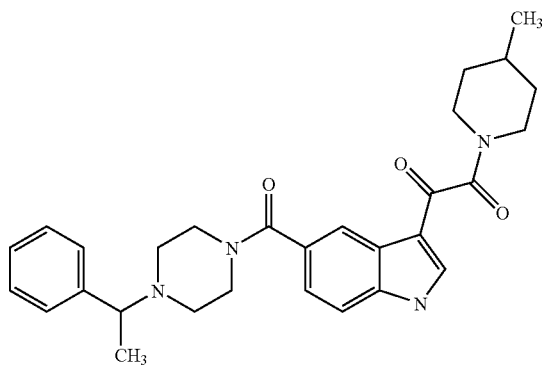
140 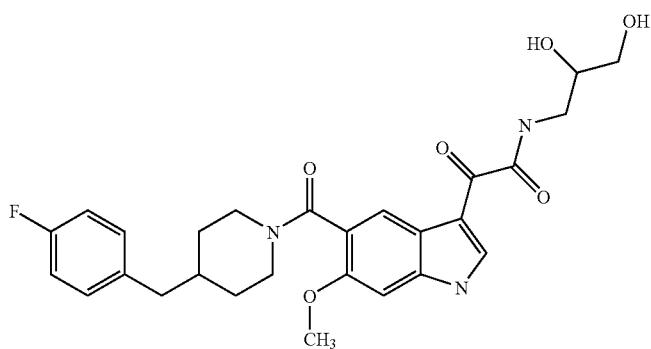
141 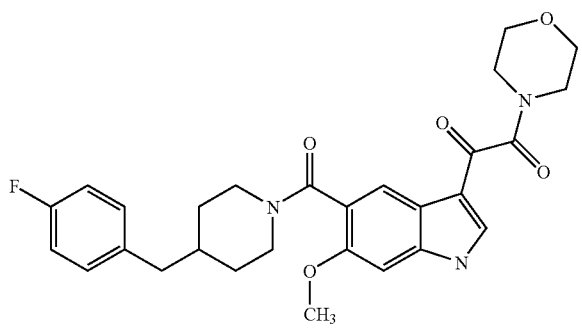
142 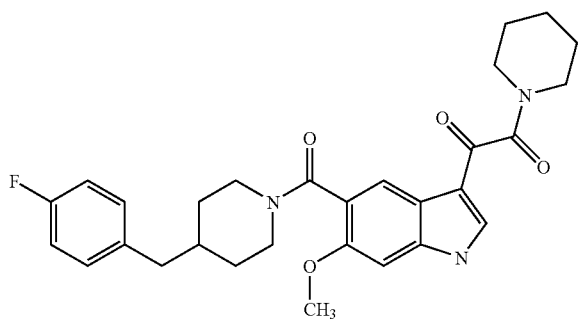

TABLE B-continued
| 143 | 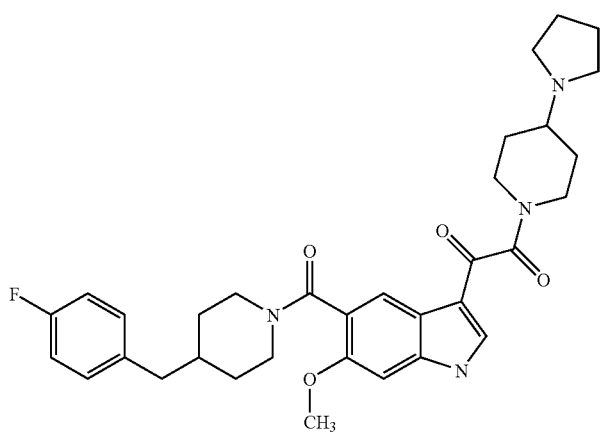 |
| --- | --- |
| 144 | 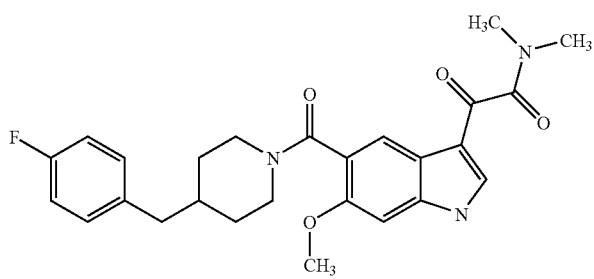 |
| 145 | 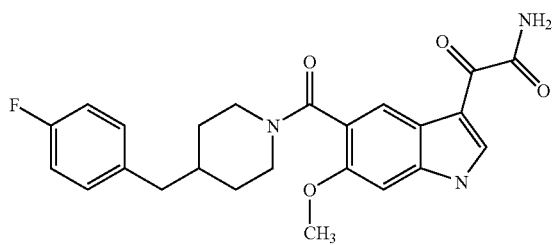 |
| 146 | 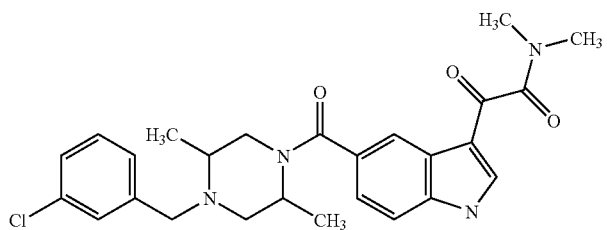 |
| 147 | 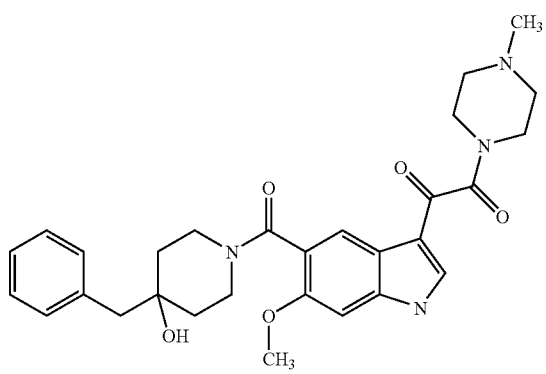 |

TABLE B-continued
148
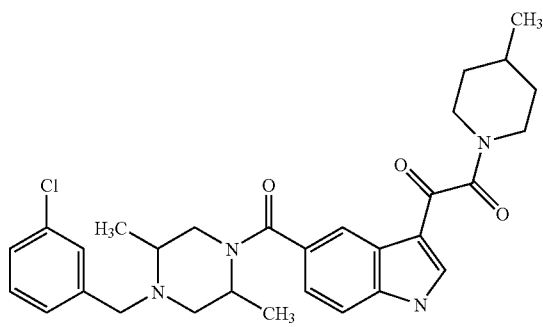
149
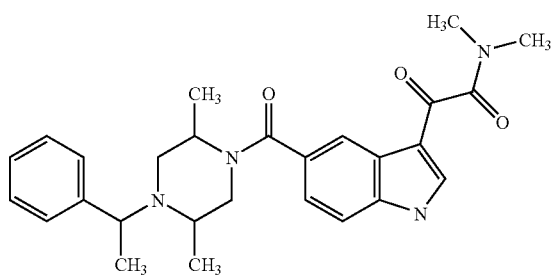
150
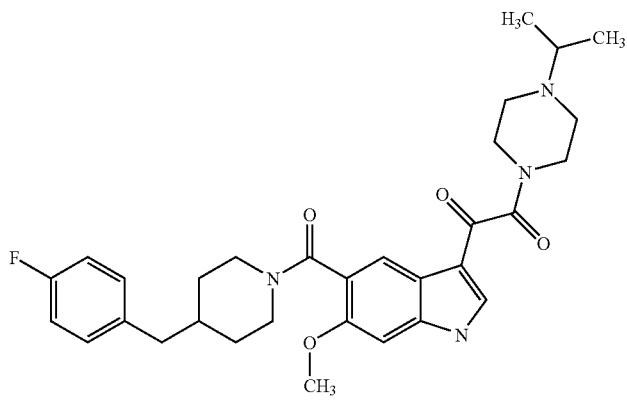
151
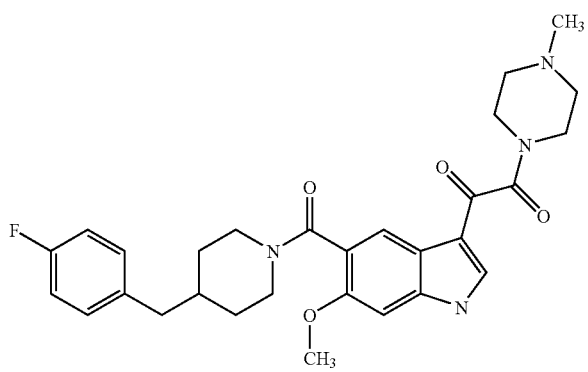

TABLE B-continued
| 152 | 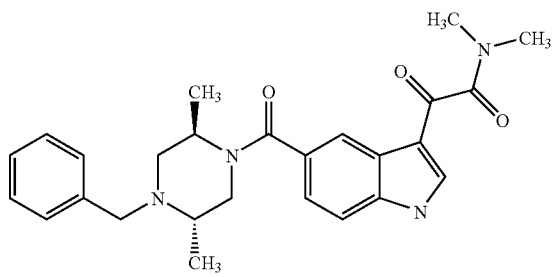 |
| 153 | 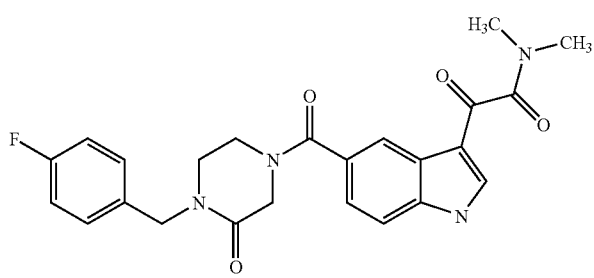 |
| 154 | 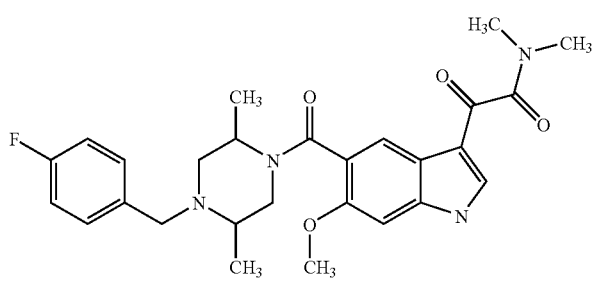 |
| 155 | 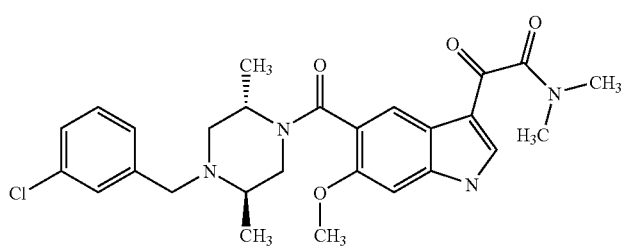 |
| 156 | 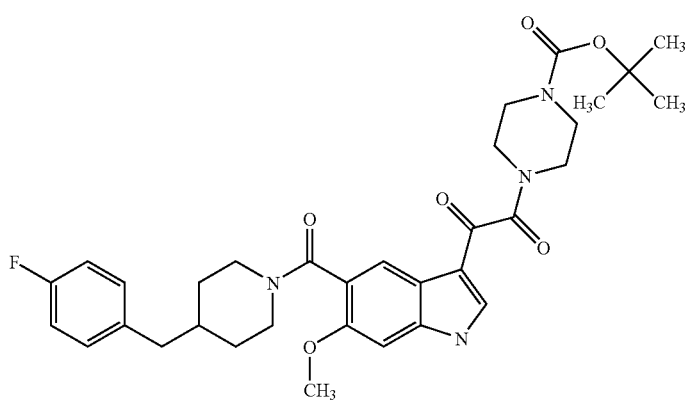 |

TABLE B-continued
| 157 | 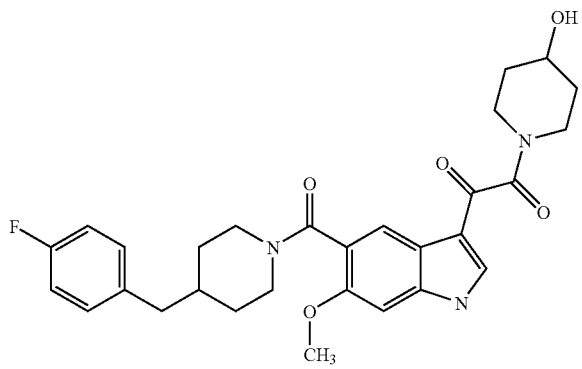 |
| --- | --- |
| 158 | 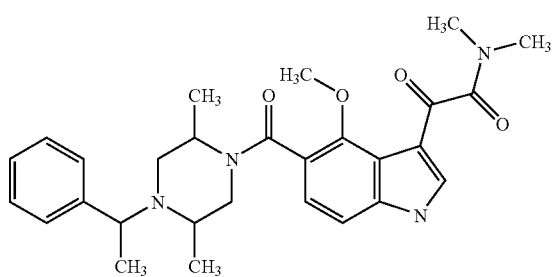 |
| 159 | 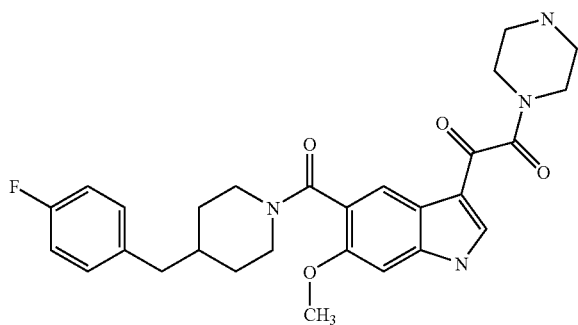 |
| 160 | 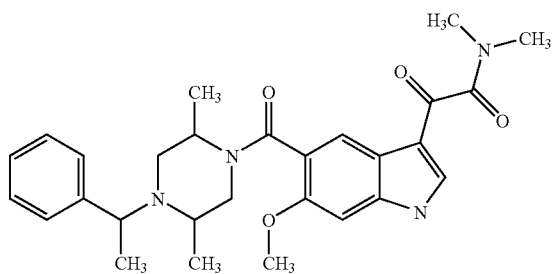 |
| 161 | 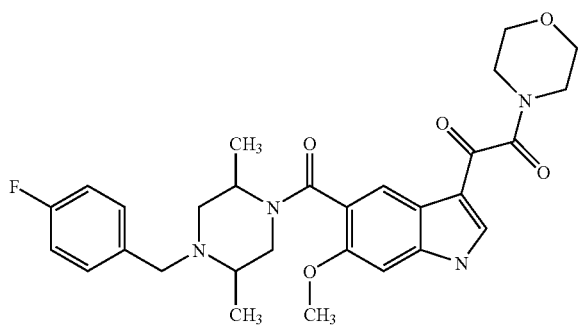 |

TABLE B-continued
| 162 | 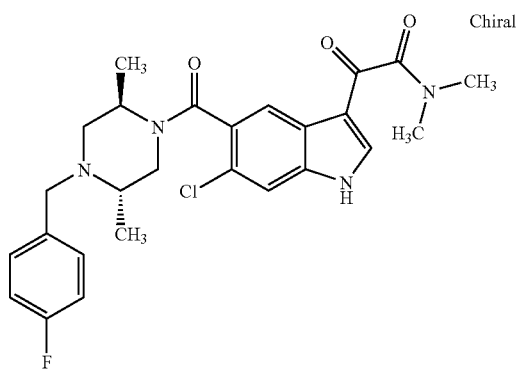 Chiral |
| 163 | 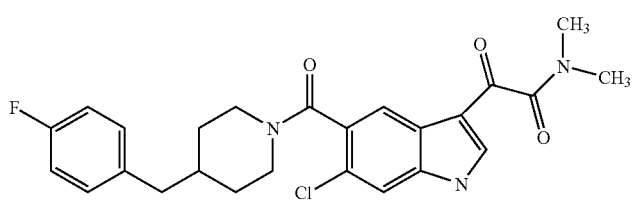 |
| 164 | 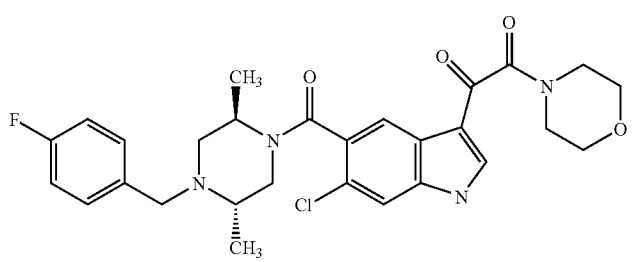 |
| 165 | 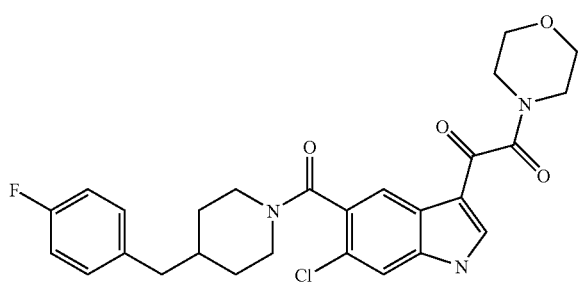 |
| 166 | 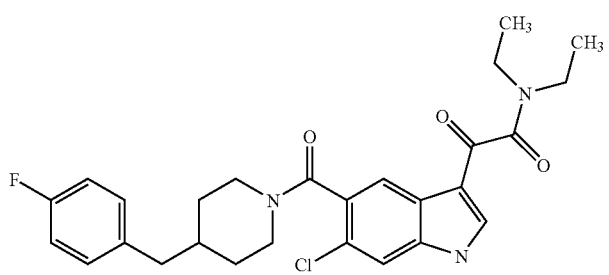 |

TABLE B-continued

167
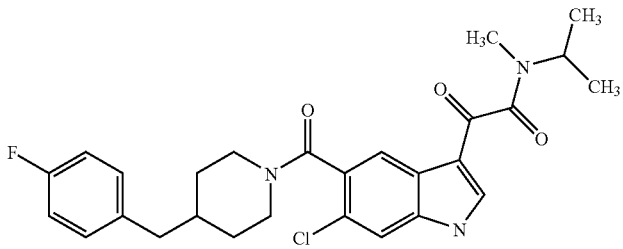

168
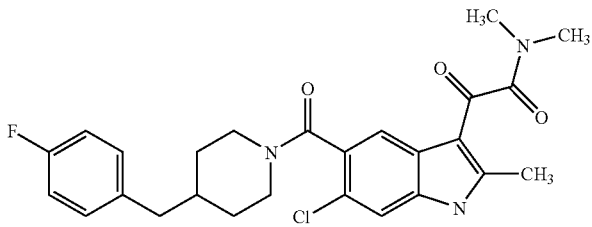

169
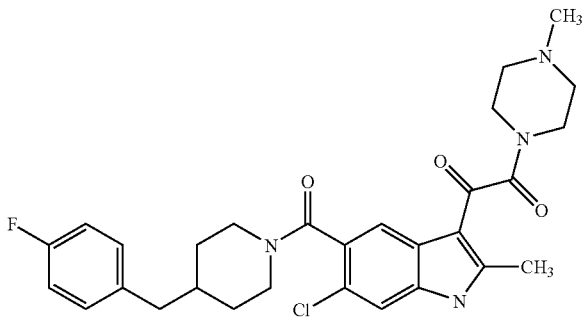

The compounds described above are provided for guidance and example only. It should be understood that other modulators of p38 kinase are useful in the invention provided that they exhibit adequate activity relative to the target protein.

Formulations and Methods of Administration

A pharmaceutical composition useful in the present invention comprises a p38 MAP kinase inhibitor (such as those described above) and a pharmaceutically acceptable carrier, excipient, diluent and/or salt.

Pharmaceutically acceptable carrier, diluent, excipient, and/or salt means that the carrier, diluent, excipient and/or salt must be compatible with the other ingredients of the formulation, does not adversely affect the therapeutic benefit of the p38 MAP kinase inhibitor, and is not deleterious to the recipient thereof.

Administration of the compounds or pharmaceutical compositions thereof for practicing the present invention can be by any method that delivers the compounds systemically and/or locally (e.g., at the site of the bone fracture, osteotomy, or orthopedic surgery). These methods include oral routes, parenteral routes, intraduodenal routes, etc.

In local applications, the compound or pharmaceutical composition is applied to the sites of bone fractures, osteotomies or grafts, for example, either by injection of the compound in a suitable solvent (e.g., an oily solvent such as arachis oil) to the fracture site or bone healing site or, in cases of open surgery, by local application thereto of such compounds in a suitable carrier such as bone-wax, demineralized bone powder, polymeric bone cements, bone sealants, polylactic acid, polyglycolic acid, polylactic acid-polyglycolic acid, etc. Alternatively, local application can be achieved by applying a solution or dispersion of the compound in a suitable carrier onto the surface or incorporating it into solid or semi-solid implants conventionally used in orthopedic surgery, such as dacron-mesh, gel-foam and kiel bone, or prostheses.

For topical applications, the compound or pharmaceutical composition thereof can be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax, sugars such as lactose and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Depending on the particular condition, disorder or disease to be treated, additional therapeutic agents can be administered together with the p38 MAP kinase inhibitors. Those additional agents can be administered sequentially in any order, as part of a multiple dosage regimen, from the p38 MAP kinase inhibitor-containing composition (consecutive or intermittent administration). Alternatively, those agents can be part of a single dosage form, mixed together with the p38 MAP kinase inhibitor in a single composition (simultaneous or concurrent administration).

For oral administration, a pharmaceutical composition useful in the invention can take the form of solutions, suspensions, tablets, pills, capsules, powders, granules, semisolids, sustained release formulations, elixirs, aerosols, and the like. Tablets containing various excipients such as sodium citrate, calcium carbonate and calcium phosphate are employed along with various disintegrants such as starch, preferably potato or tapioca starch, and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The term "parenteral" as used herein refers to modes of administration which include intravenous, intramuscular, intraperitoneal, intrasternal, subcutaneous, intramedullary and intraarticular injection and infusion. A pharmaceutical composition for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Aqueous solutions are especially suitable for intravenous, intramuscular, subcutaneous and intraperitoneal injection purposes. In this connection, the sterile aqueous media employed are all readily obtainable by standard techniques well-known to those skilled in the art. Examples of suitable aqueous and non-aqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The pharmaceutical compositions useful in the present invention can also contain adjuvants such as, but not limited to, preservatives, wetting agents, emulsifying agents, and dispersing agents. Prevention of the action of microorganisms can be ensured by the inclusion of various antibacterial and antifungal agents, such as for example, paraben, chlorobutanol, phenol sorbic acid, and the like. It can also be desirable to include isotonic agents such as sugars, sodium chloride, and the like. Prolonged absorption of the injectable pharmaceutical form can be brought about by the inclusion of agents that delay absorption such as aluminum monostearate and gelatin.

In some cases, in order to prolong the effect of the drugs, it is desirable to slow the absorption from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide, polyglycolide, and polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Administration by slow infusion is particularly useful when intrathecal or epidural routes are employed. A number of implantable or body-mountable pumps useful in delivering compound at a regulated rate are known in the art. See, e.g., U.S. Pat. No. 4,619,652.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

For purposes of transdermal (e.g., topical) administration, dilute sterile, aqueous or partially aqueous solutions (usually in about 0.1% to 5% concentration), otherwise similar to the above parenteral solutions, are prepared.

The pharmaceutical compositions useful in the invention can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

In nonpressurized powder compositions, the active ingredients in finely divided form can be used in admixture with a larger-sized pharmaceutically acceptable inert carrier comprising particles having a size, for example, of up to 100 μm in diameter. Suitable inert carriers include sugars such as lactose. Desirably, at least 95% by weight of the particles of the active ingredient have an effective particle size in the range of 0.01 to 10 μm.

Alternatively, the composition can be pressurized and contain a compressed gas, such as, e.g., nitrogen, carbon dioxide or a liquefied gas propellant. The liquefied propellant medium and indeed the total composition are preferably such that the active ingredients do not dissolve therein to any substantial extent. The pressurized composition can also contain a surface active agent. The surface active agent can be a liquid or solid non-ionic surface active agent or can be a solid anionic surface active agent. It is preferred to use the solid anionic surface active agent in the form of a sodium salt.

Compositions for rectal or vaginal administration are preferably suppositories which can be prepared by mixing the compounds of the invention with suitable non-irritating excipients or carriers such as cocoa butter, polyethylene glycol or a suppository wax which are solid at room temperature but liquid at body temperature and therefore melt in the rectum or vaginal cavity and release the drugs.

The compositions useful in the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the invention, stabilizers, preservatives, excipients, and the like. The preferred lipids are the phospholipids and the phosphatidyl cholines (lecithins), both natural and synthetic. Methods to form liposomes are known in the art (see e.g., Prescott, E., *Meth. Cell Biol.* 14:33 (1976)).

Other pharmaceutically acceptable carrier includes, but is not limited to, a non-toxic solid, semisolid or liquid filler, diluent, encapsulating material or formulation auxiliary of any type, including but not limited to ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Solid pharmaceutical excipients include, but are not limited to, starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients can be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Methods of preparing various pharmaceutical compositions with a certain amount of active ingredient are known, or will be apparent in light of this disclosure, to those skilled in this art. Other suitable pharmaceutical excipients and their formulations are described in Remington's Pharmaceutical Sciences, edited by E. W. Martin, Mack Publishing Company, 19th ed. (1995).

Pharmaceutical compositions useful in the present invention can contain 0.1%-95% of the compound(s) of this invention, preferably 1%-70%. In any event, the composition or formulation to be administered will contain a quantity of a compound(s) according to this invention in an amount effective to treat the condition, disorder or disease of the subject being treated.

One of ordinary skill in the art will appreciate that pharmaceutically effective amounts of the p38 MAP kinase inhibitor can be determined empirically and can be employed in pure form or, where such forms exist, in pharmaceutically acceptable salt, ester or prodrug form. The agents can be administered to a patient as pharmaceutical compositions in combination with one or more pharmaceutically acceptable excipients. It will be understood that, when administered to, for example, a human patient, the total daily usage of the agents or composition of the present invention will be decided within the scope of sound medical judgement by the attending physician. The specific therapeutically effective dose level for any particular patient will depend upon a variety of factors: the type and degree of the cellular response to be achieved; activity of the specific agent or composition employed; the specific agents or composition employed; the age, body weight, general health, sex and diet of the patient; the time of administration, route of administration, and rate of excretion of the agent; the duration of the treatment; drugs used in combination or coincidental with the specific agent; and like factors well known in the medical arts. For example, it is well within the skill of the art to start doses of the agents at levels lower than those required to achieve the desired therapeutic effect and to gradually increase the dosages until the desired effect is achieved.

For example, satisfactory results are obtained by oral administration of the compounds at dosages on the order of from 0.05 to 500 mg/kg/day, preferably 0.1 to 100 mg/kg/day, more preferably 1 to 50 mg/kg/day, administered once or, in divided doses, 2 to 4 times per day. On administration parenterally, for example, by i.v. bolus, drip or infusion, dosages on the order of from 0.01 to 1000 mg/kg/day, preferably 0.05 to 500 mg/kg/day, and more preferably 0.1 to 100 mg/kg/day, can be used. Suitable daily dosages for patients are thus on the order of from 2.5 to 500 mg p.o., preferably 5 to 250 mg p.o., more preferably 5 to 100 mg p.o., or on the order of from 0.5 to 250 mg i.v., preferably 2.5 to 125 mg i.v. and more preferably 2.5 to 50 mg i.v.

Dosaging can also be arranged in a patient specific manner to provide a predetermined concentration of the agents in the blood, as determined by techniques accepted and routine in the art (HPLC is preferred). Thus patient dosaging can be adjusted to achieve regular on-going blood levels, as measured by HPLC, on the order of from 50 to 5000 ng/ml, preferably 100 to 2500 ng/ml.

Kits

The invention also relates to combining separate pharmaceutical compositions in kit form useful for bone healing. The kit can have a carrier means being compartmentalized in close confinement to receive two or more container means therein, having (1) a first container means containing a therapeutically effective amount of a p38 MAP kinase inhibitor and (2) a second container means containing a therapeutically effective amount of carrier, excipient or diluent. Optionally, the kit can have additional container mean(s) containing a therapeutically effective amount of additional agents.

The kit comprises a container for containing the separate compositions such as a divided bottle or a divided foil packet, however, the separate compositions can also be contained within a single, undivided container. Typically the kit comprises directions for administration of the separate components. The kit form is particularly advantageous when the separate components are preferably administered in different dosage forms (e.g., oral and parenteral) or at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It can be desirable to provide a memory aid on the kit, e.g., in the form of numbers next to the tablets or capsules whereby the numbers correspond with the days of the regimen which the dosage form so specified should be ingested. Another example of such a memory aid is a calendar printed on the card e.g., "First Week, Monday, Tuesday . . . Second Week, Monday, Tuesday . . . " etc. Other variations of memory aids will be readily apparent. A "daily dose" can be a single tablet or capsule or several tablets or capsules to be taken on a given day. Also, a daily dose of the compound, a prodrug thereof, or a pharmaceutically acceptable salt of the compound can consist of one tablet or capsule while a daily dose of the second compound can consist of several tablets or capsules and vice versa. The memory aid should reflect this.

It will be readily apparent to one of ordinary skill in the relevant arts that other suitable modifications and adaptations to the methods and applications described herein can be made without departing from the scope of the invention or any embodiment thereof.

The following examples are offered to illustrate but not to limit the invention.

EXAMPLES

Example 1

It has been found that fracture healing in rats treated with a COX-2 inhibitor, rofecoxib (Vioxx, Merck Co.) or celecoxib (Celebrex, Pharmacia Corp.), was dramatically impaired.

Histological studies indicated that COX-2 function is essential for endochondral ossification during the fracture healing process. COX-2 is induced by pro-inflammatory stimuli and the prostaglandins made by COX-2 can enhance inflammation. Inflammation is an early phase of fracture healing and it has been theorized that inflammation initiates the bone healing cascade of molecular and cellular events. Therefore, it was also hypothesized that the inflammation event itself was important for initiating and maintaining the fracture healing cascade and not strictly a function of COX-2.

Closed femur fractures were made in female retired breeder Sprague-Dawley rats. The rats were given oral doses of the p38 MAP kinase inhibitor (compound 25, Table B)(30 mg/kg) once or twice per day and either vehicle only (control) or rofecoxib (Vioxx, 3 mg/kg, once a day) as a positive control for fracture inhibition. The data indicated that the p38 MAP kinase inhibitor does not negatively affect fracture healing and can actually enhance or accelerate the healing process.

The histological analysis indicated that the p38 MAP kinase inhibitor enhanced fracture healing by increasing and/or accelerating calcified cartilage formation as well as new bone formation. Potential changes in the distal femur growth plate of the p38 MAP kinase inhibitor treated rats suggested that the p38 MAP kinase inhibitor could be affecting growth plate chondrocyte metabolism.

Osteoclasts were noted within the fracture calluses of the p38 MAP kinase inhibitor treated rats. The amount of osteoclasts was not quantified but appeared to approximate levels found in control rats.

Results

Drug Dosing and Fracture Production

The initial set of 24 rats used for these experiments was designated group A (Table 4). These rats received drug in PEG300 as vehicle and at a dose of 1 ml/kg. Six of the 24 rats in group A died from apparent toxicity to either the batch of PEG300 or the 1 ml/kg dose since rats died in each of the 4 treatment categories. A seventh rat was euthanized due to its poor appearance, also apparently from the PEG300 toxicity effect. Among the remaining rats, a general poor state of health was observed with rats not eating or drinking and demonstrating a very lethargic behavior during the five days of drug administration. To alleviate this problem, a different batch of PEG300 (Sigma) was used and the dose was dropped to 0.5 ml/kg for the remainder of the animals used (rats 25-124). No further PEG300 toxicity was observed.

The prior set of experiments examining the effects of COX-2-selective NSAIDs on fracture healing used retired breeder male Sprague-Dawley rats with an average size of approximately 600 g. To stabilize the femur fractures in these animals, a stainless steel rod with a diameter of 1.1 mm was used. This same diameter rod was continually used during the initial phases of this study even though 250-300 g retired breeder female Sprague-Dawley rats were used. The quality of the femur fractures produced was poor in these rats (Groups A and B, Table 4). It was hypothesized that the 1.1 mm diameter rod was too stiff and was actually creating comminuted fractures. To test this hypothesis 0.8 and 0.9 mm diameter rods were used for fracture stabilization in the smaller female rats (rats 58 and 59, Table 4). The 0.8 mm diameter rod appeared to work slightly better than the 0.9 mm diameter rod and so the 0.8 mm diameter rod was used for the remainder of these experiments (Group C, Table 4). After switching to the smaller diameter rod, fracture quality increased to levels comparable to that previously obtained using the larger male rats; only 7 of the 65 rats in group C were immediately disqualified from the study due to poor fracture quality (see Appendix A).

Radiographic Analysis

All rats were radiographed at time of sacrifice and representative radiographs can be found in FIGS. 1A-1I, 2A-2F, 3A-3E, and 4A-4H. Using the scoring system described in the Materials and Methods section, infra, the 4 week post-fracture radiographs from the p38 MAP kinase inhibitor treated rats had significantly higher scores than the control or rofecoxib treated rats (see Table 1). These observations are clearly indicative of advanced healing in the p38 MAP kinase inhibitor treated rats.

Figure 1H:
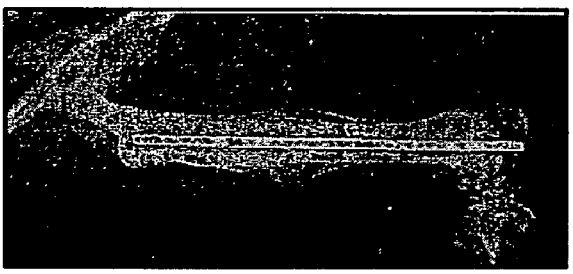
Figure 1I:
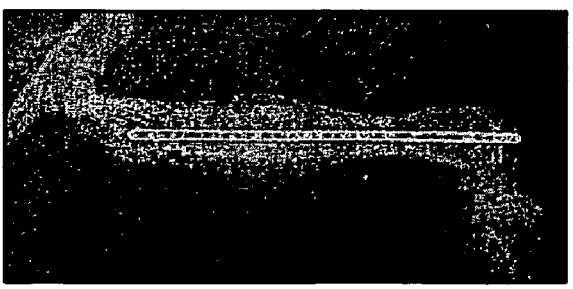
Figure 2A:
FIGS. 2A-2F. Radiographs from rofecoxib treated rats at 4 weeks post-fracture.
Figure 2D:
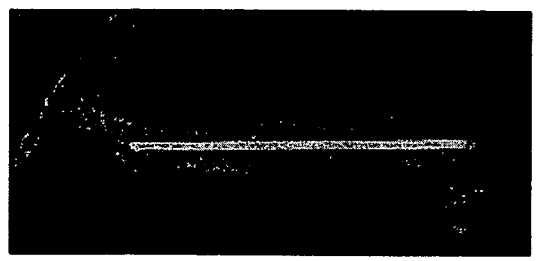
Figure 2B:
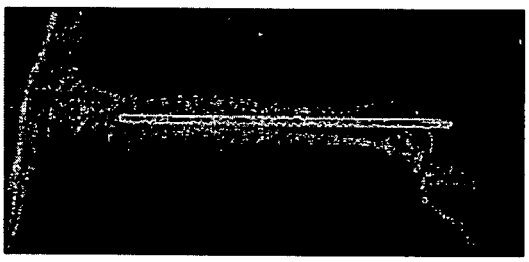
Figure 2E:
Figure 2C:
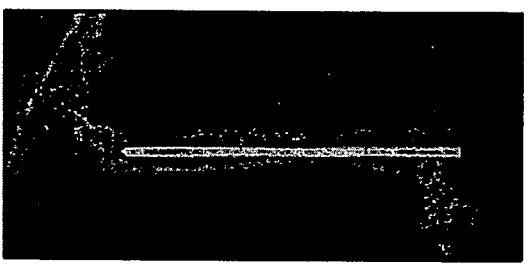
Figure 2F:
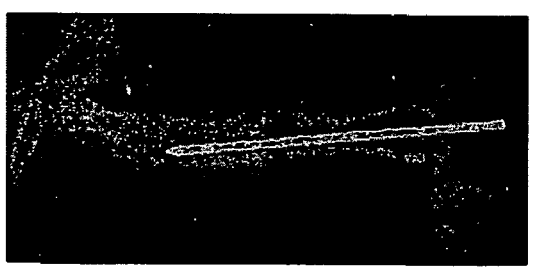
Figure 3A:
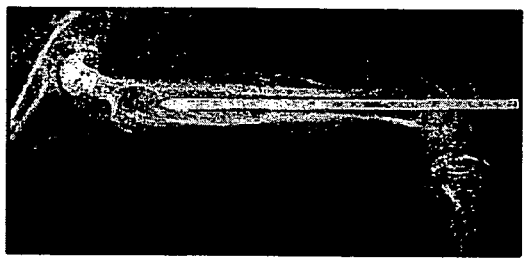
FIGS. 3A-3E. Radiographs from p38 MAP kinase inhibitor, once per day, treated rats at 4 weeks post-fracture.
Figure 3B:
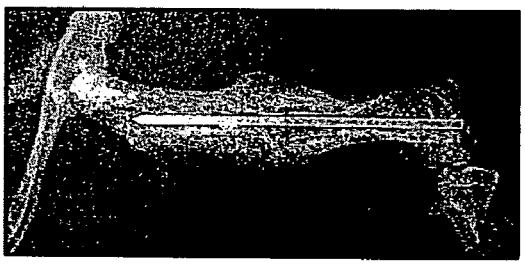
Figure 3C:
Figure 3D:
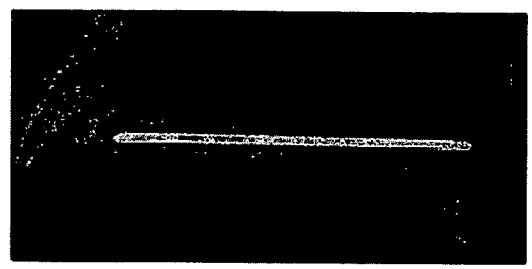
Figure 3E:
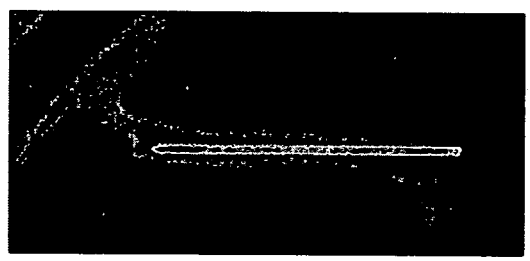
Figure 4A:
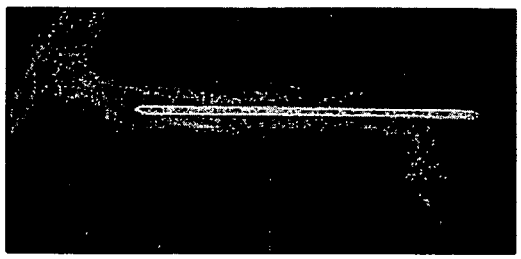
FIGS. 4A-4H. Radiographs from p38 MAP kinase inhibitor, twice per day, treated rats at 4 weeks post-fracture.
Figure 4B:
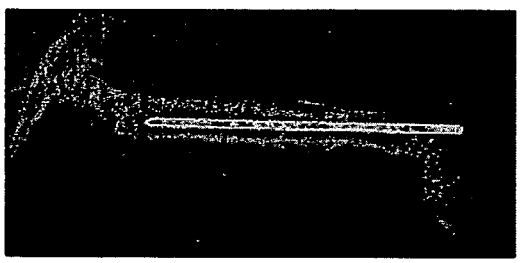
Figure 4C:
Figure 4D:
Figure 4E:
Figure 4F:
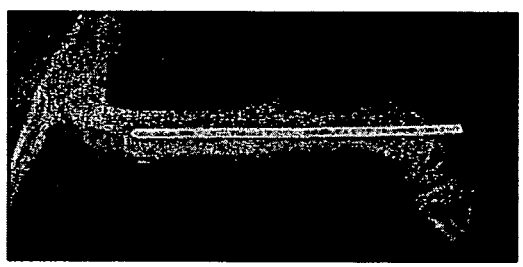
Figure 4G:
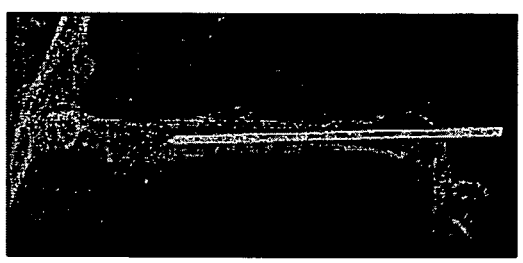
Figure 4H:
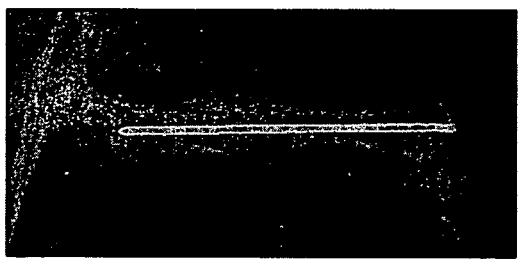
Figure 6A:
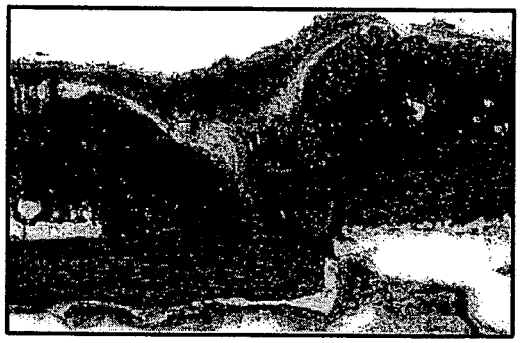
FIGS. 6A-6D. Histological analysis of fracture healing in drug treated rats at 2 weeks post-fracture.
Figure 6B:
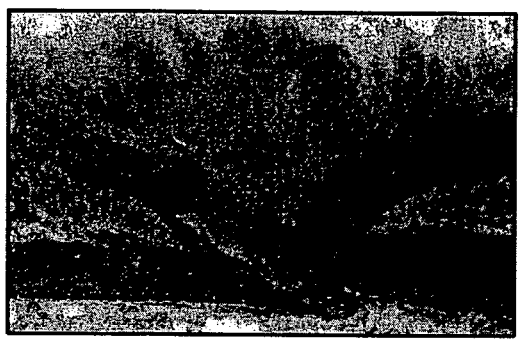
Figure 6C:
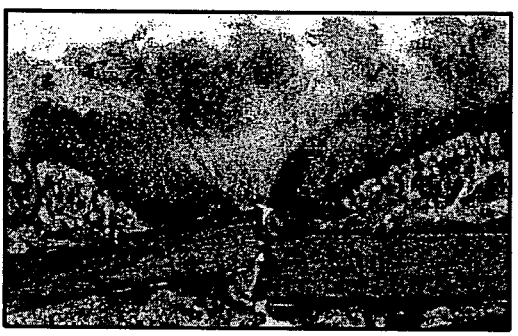
Figure 6D:
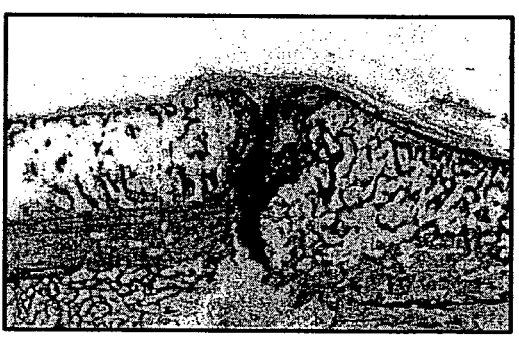

Radiographs from the control rats at 4 weeks post-fracture appeared to be following a normal healing response (FIGS. 1A-1I). In the majority of the control rats, the fracture was not bridged at either apex of the fracture callus or by new bone formation at the cortical bone ends of fracture site. An example of rat that shows no bridging was rat #65 (FIG. 1A). In contrast, bridging at the apex of the fracture callus and new bone formation (characterized by a cotton-ball-like appearance) was evident at the fracture site in the top-half of the fracture callus from rat #114 (FIG. 1H). The negative effects of rofecoxib on fracture healing were evident in the radiographs shown in FIGS. 2A-2F. In most of the fractures, the fracture site was still plainly evident and little or no bridging was evident. An exception was rat #96 (FIG. 2B) where bridging is evident. Note that the radiograph for rat #123 (FIG. 2F) appeared to have been made with the femur at an angle (not perpendicular between the X-ray beam and the femur's long axis) and thus though it can appear to be bridged, the circular pattern within the radiograph indicates that it was not bridged.

p38 MAP kinase inhibitor treatment appears to accelerated fracture healing as per the radiographic analysis (see FIGS. 3A-3E and 4A-4H and Table 1). As can be seen in FIG. 3A for rat #60, the top apex of the fracture callus was clearly bridged and new bone formation (cotton-ball-like appearance) also appeared to be bridging the top of the fracture in this animal. In contrast, the apex of the bottom half of this callus (Rat #60) did not appear to be bridged. Similar and even better examples of accelerated healing were found among the other radiographs of the p38 MAP kinase inhibitor treated rats. Note that the radiograph for rat #61 (FIG. 6B) is indicative of reactive bone formation caused by infection, but no evidence of infection (other than the X-ray) was found when this femur was harvested for mechanical testing.

TABLE 1

Radiographic comparisons between treatment groups at 4 weeks post-fracture in Group C rats (rats 60–124).

|  | Control | Rofecoxib | p38 MAP Kinase Inhibitor | p38 MAP Kinase Inhibitor × 2 |
|---|---|---|---|---|
| Mean | 1.33 | 0.83 | 3.2 | 3.75 |
| Range | 0–4 | 0–3 | 3–4 | 3–4 |
| Sample size | 9 | 6 | 5 | 8 |
| P value* | — | 0.46 | <0.01 | <0.001 |

*Standard two-tailed T-test comparisons to the Control group values.

Mechanical Analysis

Torsional mechanical testing was performed on the fractured (right) and contralateral (left) femurs from control, rofecoxib (3 mg/kg/day); p38 MAP kinase inhibitor (30 mg/kg/day), and p38 MAP kinase inhibitor (2×30 mg/kg/day). The stabilizing rods were removed from the femurs prior to testing and the femurs were wrapped in saline soaked gauze to prevent dehydration prior to testing. The ends of the femurs were potted in hex nuts with Wood's metal and the peak torque and angle failure determined using an MTS servohydraulic mechanical testing machine and a 20 Nm reaction torque load cell as per standard procedures (Simon, A. M. et al., *J. Bone Miner. Res.* 17:963-976 (2002)). Femur and fracture callus dimensions and gage length were measured before and after mechanical testing using digital calipers. The values obtained were used to calculate torsional rigidity, and shear stress as described (Simon, A. M. et al., *J. Bone Min. Res.*, in press (2002)). Finally, the data was normalized as the percentage of the fractured femur relative to the contralateral femur for each animal. This helped to reduce animal-to-animal variability.

Figure 5A:
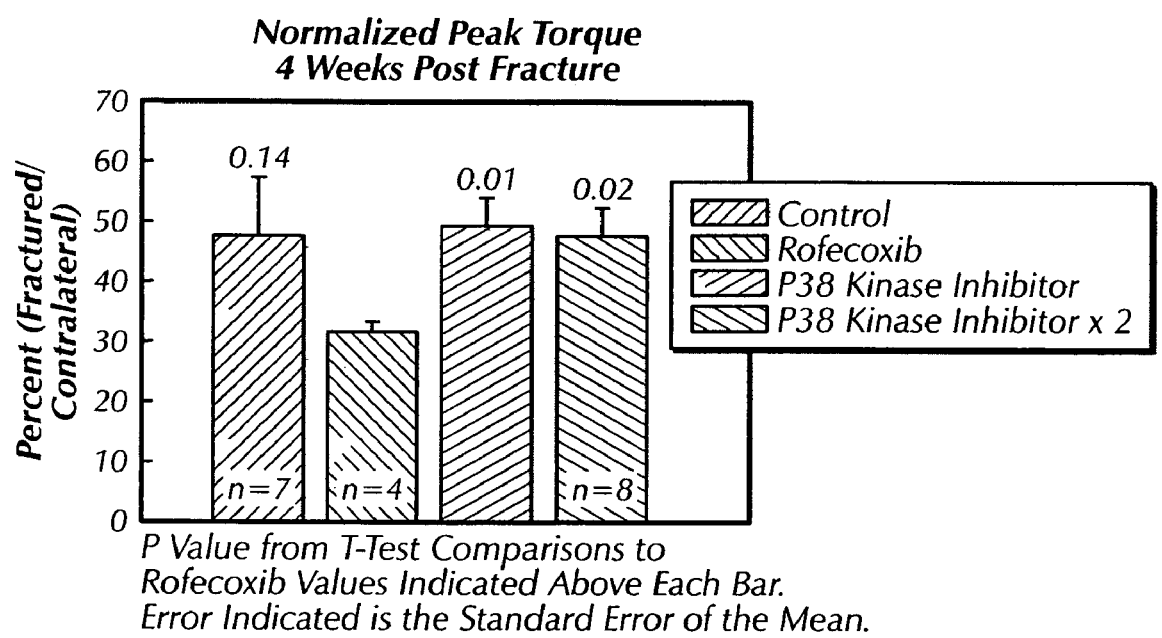
FIGS. 5A-5C. Graphical representation of the mechanical testing data at 4 weeks post-fracture.
Figure 5B:
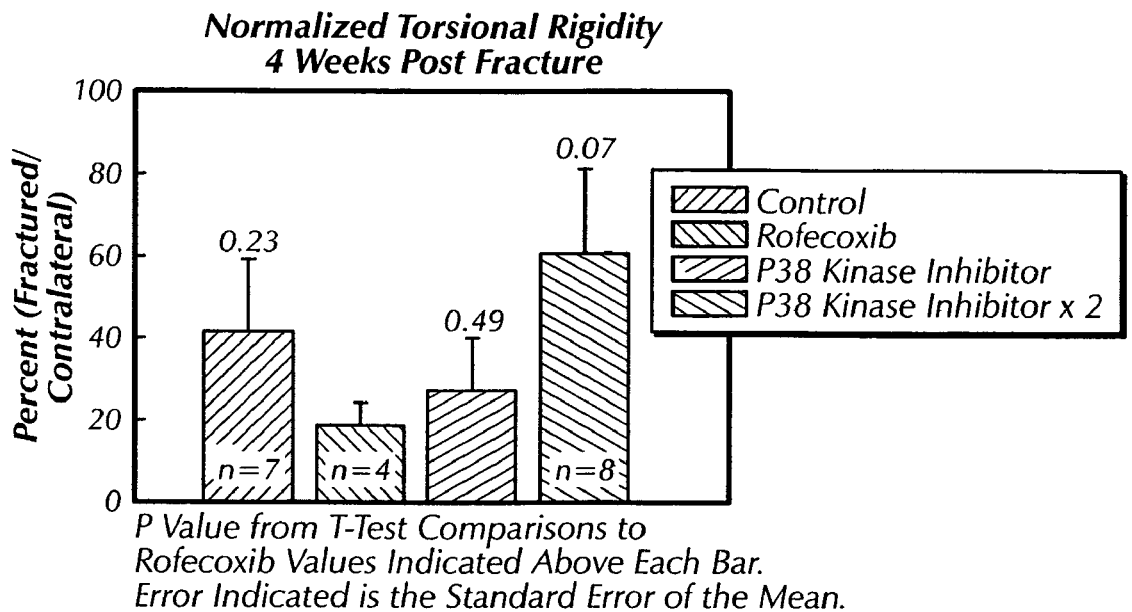
Figure 5C:
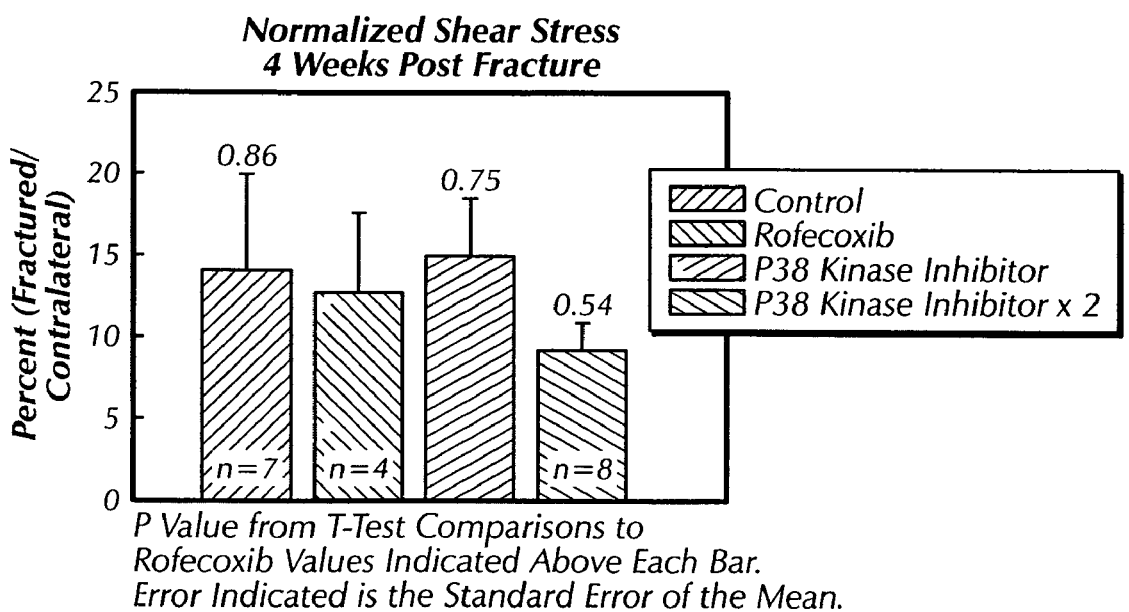

The results obtained from the mechanical testing of the 4 week post-fracture femurs (Group C; rats 60-124) are shown in Table 2 and graphically in FIGS. 5A-5C. p38 MAP kinase inhibitor treatment significantly increased normalized peak torque relative to rofecoxib treated rats but not relative to the control animals (FIG. 5A). Similarly, normalized torsional rigidity approached a statistical significant difference between the twice-a-day p38 MAP kinase inhibitor treated rats and rofecoxib treated rats but not the control rats (FIG. 5B). No significant differences were found in the normalized shear stress among the different treatment groups (FIG. 5C).

TABLE 2

Summary of Normalized Mechanical Testing Data from Rat Group C at 4 weeks post-fracture.

|  | Control | Rofecoxib | p38 MAP Kinase Inhibitor | p38 MAP Kinase Inhibitor × 2 |
|---|---|---|---|---|
| NPT | 48 ± 25 | 32 ± 3 | 50 ± 11 | 48 ± 14 |
| NTR | 42 ± 44 | 19 ± 9 | 28 ± 24 | 61 ± 55 |
| NSS | 14 ± 15 | 13 ± 9 | 15 ± 8 | 10 ± 4 |
| Sample Size | 7 | 4 | 5 | 8 |

NPT = normalized peak torque;
NTR = normalized torsional rigidity;
NSS = normalized shear stress.
Errors indicated are standard deviations.

Mechanical testing was also performed on the femurs of rats that were available from Groups A and B (rats 1-57; see Appendix A). Unfortunately the number of rats available for these tests from these groups was too small for any statistical evaluation. However, a very high normalized peak torque (~150%) and normalized torsional rigidity (~150%) was found in the twice-a-day p38 MAP kinase inhibitor treated rats (see Table 3). These values are exceptionally high and are not normally found during fracture healing in untreated rats when one can expect to find normalized peak torque and normalized torsional rigidity values to reach a maximum of less than or equal to 100%. These data again indicate that p38 MAP kinase inhibitor treatment was accelerating and/or enhancing fracture healing.

TABLE 3

Summary of Mechanical Testing Data from Rat Groups A and B.

| Weeks | Control | | | Rofecoxib | | | p38 MAP Kinase Inhibitor | | | p38 MAP Kinase Inhibitor × 2 | | |
|---|---|---|---|---|---|---|---|---|---|---|---|---|
| post-fx | 4 | 6 | 8 | 4 | 6 | 8 | 4 | 6 | 8 | 4 | 6 | 8 |
| NPT | 46 | — | — | — | — | 57 ± 42 | 57 | 85 ± 17 | — | — | 97 | 158 ± 46 |
| NTR | 43 | — | — | — | — | 100 ± 82 | 69 | 109 ± 52 | — | — | 126 | 156 ± 68 |
| NSS | 10 | — | — | — | — | 16 ± 8 | 14.1 | 36 ± 11 | — | — | 63 | 45 ± 1 |
| Sample size | 1 | — | — | — | — | 2 | 1 | 3 | — | — | 1 | 2 |

NPT = normalized peak torque;
NTR = normalized torsional rigidity;
NSS = normalized shear stress.
Errors indicated are standard deviations.

Histology

The histological findings are shown in FIGS. 6A-6D, 7 and 8A-8E. At two weeks post-fracture and normal healing process in the control group (FIG. 6A) was observed which was characterized by woven bone formed from the periphery of the callus towards the center followed by an area of calcified cartilage (orange in color with embedded chondrocytes), then chondrocytes and cartilage (deep blue), with fibroblastic cells at the center of the callus. In the rofecoxib treated animal (FIG. 6B), less woven bone formation was observed as it did not approach the cortical bone ends of the fracture site and an abundance of chondrocytes. In the rat treated with the p38 MAP kinase inhibitor once per day (FIG. 6C), a near normal amount of woven bone but more than normal amounts of chondrocytes was observed. Finally in the rat treated with the p38 MAP kinase inhibitor twice per day (FIG. 6D), advanced healing with the fracture gap almost filled with newly formed woven bone was observed.

Figure 7:
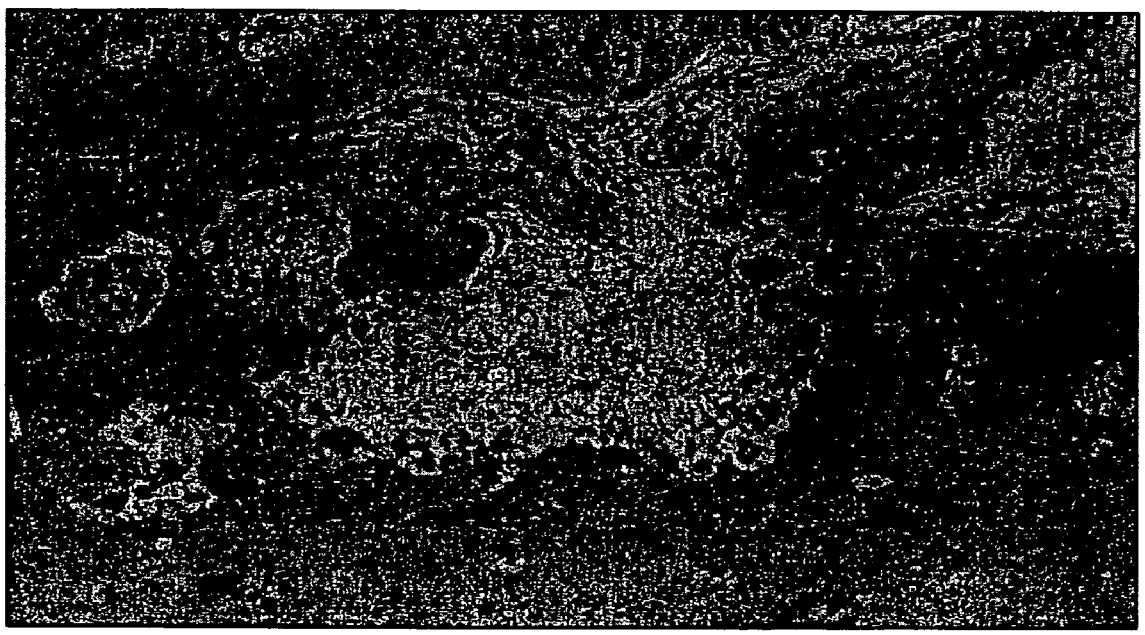
FIG. 7. Histological analysis of the fracture callus of p38 MAP kinase inhibitor treated rat.

One potential mechanism by which the p38 MAP kinase inhibitor could be enhancing fracture healing is by reducing osteoclast number. Osteoclasts were observed in the p38 MAP kinase inhibitor treated fracture callus (FIG. 7). As discussed above, p 38 MAP kinase activity positively regulates osteoclast differentiation. The number of osteoclasts appeared to be about the same as in control animals but this parameter was not quantified.

Figure 8A:
FIGS. 8A-8E. Histological analysis of growth plate morphology of drug treated rats.
Figure 8B:
Figure 8C:
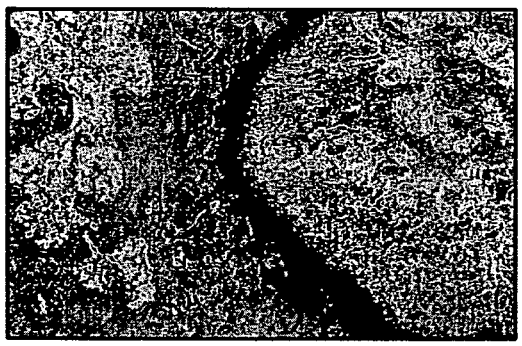
Figure 8D:
Figure 8E:

There were also some variations in growth plates of the contralateral control femurs (FIGS. 8A-8E). The distal femur growth plate appeared to be normal in the control (FIG. 8A) and rofecoxib (FIG. 8B) treated animals. However, in the p38 MAP kinase inhibitor treated rats at two weeks post-fracture (FIGS. 8C and 8D), there appeared to a slight decrease in chondrocyte cell layers in the resting and proliferative zones, a decrease in the maturation of the calcification zone, and an increase in the amount of new bone in the growth plate calcified zone, which could also be interpreted as a decrease in the calcified zone since this was replaced with new bone. Large amounts of new bone formation at the growth plate of a p38 MAP kinase inhibitor (twice a day) rat at 4 weeks post-fracture and the near absence of any calcified cartilage were observed (FIG. 8E). This suggested that p38 MAP kinase inhibitor treatment was enhancing the differentiation of the chondrocytes at the growth plate.

Materials and Methods

Animals and Drug Dosing

Retired breeder female Sprague-Dawley rats were purchased from Taconic Farms. The rats were housed in pairs and given food and water ad libitum. A total of 124 rats were purchased for these experiments (Table 4). However, only 65 rats were used for the final set of experiments as described in Table 4. Drugs were first administered to the rats by gavage using PEG300 (Sigma) as a carrier (0.5 ml per kg). Rats were initially gavaged with drugs 6 hours after surgery (between 4 and 6 PM on day 1) and then twice/day afterwards for 5 days (between 6-8 AM and again between 5-7 PM). Drug dosing regimes are shown in Table 5. The p38 MAP kinase inhibitor used in the experiments is compound 25, Table B. Rofecoxib was obtained by pulverizing Vioxx pills (Merck).

TABLE 4

| Group | Rat Numbers | Number of Experimental Rats | Variables | Disposition |
|---|---|---|---|---|
| A | 1–24 | 24 | 1 ml/kg PEG, thick rod (1.1 mm dia.) | See Appendix A |
| B | 25–57 | 33 | 0.5 ml/kg PEG, thick rod (1.1 mm dia.) | See Appendix A |
|  | 58 and 59 | 2 | Rod diameter test rats | Not used for data analysis |
| C | 60–124 | 65 | 0.5 ml/kg PEG, thin rod (0.81 mm dia.) | Radiographic, histological, and mechanical analyses |
| Total |  | 124 |  |  |

TABLE 5

Drug Dosing Regimes

| | Dose | AM (6–8 AM) | PM (5–7 PM) |
|---|---|---|---|
| Control | — | PEG | PEG |
| Rofecoxib | 3 mg/kg | PEG | Drug |
| p38 MAP Kinase Inhibitor-A | 30 mg/kg | PEG | Drug |
| p38 MAP Kinase Inhibitor-B | 30 mg/kg | Drug | Drug |

Fracture Production

Rats were anesthetized with a ketamine-xylazine mixture. The right hindlimb was shaved, and cleansed with betadine. A medial parapatellar incision was made through the skin and underlying muscle to the distal end of the femur. The patella was dislocated laterally to expose the femoral condyles. A 20 g needle was used to drill a hole into the distal end of the femur, between the condyles, and then used to ream the femoral canal. A 0.81 mm diameter stainless steel wire was then inserted into the femoral condyle and tamped into the proximal end of the femur. The rod was then trimmed as close as possible to the femoral condyles with wire cutters. The incision was closed in two layers with resorbable Vicryl sutures. A mid-shaft transverse fracture was made in the right femur using a three-point bending device as described previously (Bonnarens, F. and Einhorn, T. A., J. Orthop. Res. 2:97-101 (1984)).

Radiography

Radiographs were made using an HP Faxitron and Kodak MINR2000 mammography film. Radiographs were photographed with and Olympus C-3040 digital camera for figure preparation. The 4 week post-fracture radiographs from all the rats that had survived to 4 weeks in Group C (rats 60-124) and which were not comminuted, infected, or destabilized were scored as follows. One point was assigned to each radiograph in which a cortex of the fracture callus appeared bridged and/or where the cortical bone fracture site appeared to be bridged by new bone. Thus a radiograph could have a minimal score of 0 or a maximal score of 4.

Histology

Femurs were dissected from rats at 2, 4, 6, and 8 weeks as detailed in Appendix A. Soft tissue was dissected from the femurs and the femurs were fixed overnight in buffered formalin. The femurs were then embedded in polymethylmethacrylate (PMMA) following standard procedures. Longitudinal sections (~200 um thick) were cut from the PMMA blocks and ground and polished to a thickness of approximately 50-100 um. The sections were then stained with Van Gieson's picrofuschin and Stevenel's Blue. This results in dark blue to purple staining of cartilage and lighter polychromatic blue staining of other cell types such as fibroblasts, osteoblasts, and osteoclasts; red staining of bone; and orange to red staining of calcified cartilage. Sections were photographed with an Olympus BH2 microscope.

Mechanical Testing

Rats were sacrificed at 4 weeks post-fracture by $CO_2$ asphyxiation. Rats with oblique, comminuted, or infected fractures were not used for mechanical testing (see Appendix A). Both femora were removed and cleaned of all soft tissue leaving the fracture callus undisturbed and then immediately processed for mechanical testing. The samples were wrapped in saline soaked gauze to prevent dehydration between steps. Measurements of the femora were taken using digital calipers to determine femur length and external callus dimensions. The intramedullary pin was removed from the fractured femur. The femoral ends were potted in 1-inch hexnuts using a low melt temperature metal (Wood's metal, Alfa Aesar, Ward Mill, Mass.). Once potted, the gage length (L) of each femur was measured. Torsional testing was conducted using a servohydraulic testing machine (MTS, Eden, Praire, Minn.) with a 20 Nm reaction torque cell (Interface, Scottsdale, Ariz.). The testing was carried out to failure at a rate of 2°/sec and a data recording rate of 20 Hz. Both the fractured and intact femora were tested in internal rotation in proper anatomic orientation. The peak torque and angle at failure were calculated from the load-deformation curves. Internal fracture callus dimensions were measured after mechanical testing. From the callus dimensions, the polar moment of inertia (J) was calculated based upon a hollow ellipse model (Bell, G. H. et al., J. Physiol. 100:299-317 (1941); Engesaeter, L. B. et al., Acta Orthop. Scand. 49:512-518 (1978)).

The equations used to derive torsional rigidity, shear stress, and J were as follows (Popov, E. P., INTRODUCTION TO MECHANICS OF SOLIDS, Englewood Cliffs, N.J., Prentice-Hall, Inc. (1968)): (i) Torsional Rigidity: $(T_{max} \cdot L)/\phi$ where $T_{max}$ is the peak torque value in Nmm, L is the gage length in mm, and $\phi$ is the angle at failure in radians; (ii) Shear Stress: $(T_{max} \cdot R_{max})/J$ where $R_{max}$ is the largest radial dimension of the fracture callus in mm ($a_o$) and J is the polar moment of inertia; (iii) Polar Moment of Inertia (J): $[\pi(ab^3+a^3b-(a-t)(b-t)^3-(a-t)^3(b-t)]/4$ where a is $[a_i+[(a_o-a_i)/2]$; b is $[b_i+[(b_o-b_i)/2]$; t is the average bone thickness at the site of failure and is calculated as $[(a_o-a_i)+(b_o-b_i)]/2$ where $a_o$ is the callus maximum outside radius, $a_i$ is the maximum interior radius, $b_o$ is the least outside radius, and $b_i$ is the least interior radius in mm. Only torsional testing data for which the fractured and control femur tested without incident were used.

Discussion

Fracture Healing and p38 MAP Kinase Inhibitor

It is evident from the experimental results that the inflammation response per se is not essential for successful fracture healing. However, it has not been independently corroborated that the p38 MAP kinase inhibitor dose(s) used actually reduce or eliminate the early inflammation response in rats following bone fracture. Assuming that p38 MAP kinase inhibitor does indeed eliminate inflammation, than the data indicate that COX-2 has essential function during fracture healing, unrelated to the initial inflammation response. The fractured femurs from the p38 MAP kinase inhibitor treated rats had mechanical properties similar or better than control animals (Tables 2 and 3, FIGS. 5A-5C), and radiographic properties significantly better that control animals (Table 1), indicating that the p38 MAP kinase inhibitor does not negatively affect and can in fact enhance fracture healing. Conversely, even 5 days of treatment with rofecoxib negatively affected the mechanical and to a lesser extent the radiographic properties of the healing rat femur fractures. The data support a theory in which early COX-2 inhibition is deleterious to fracture healing but that this is not directly related to a pro-inflammatory response and can in fact be more involved in inflammation resolution. The p38 MAP kinase inhibitor is accelerating and/or enhancing the fracture healing process based upon the radiographic observations and the mechanical testing analyses at later time points (such as 8 and 12 weeks post-fracture). The histological observations at two weeks post-fracture also support this contention (FIGS. 6A-6D). Furthermore, the p38 MAP kinase inhibitor has no negative effect on fracture healing, unlike Celebrex or Vioxx. Therefore, the p38 MAP kinase inhibitor should be a better post-fracture, post-orthopedic surgical procedure analgesic and/or anti-inflammatory medication.

Potential Mechanism of Action for p38 MAP Kinase Inhibitors on Fracture Healing

The following have been observed: an apparent increase in the amount of new woven bone within the callus and perhaps some more calcified cartilage than in control rats (FIG. 7). This suggests that the p38 MAP kinase inhibitor acts to enhance fracture healing by promoting chondrocyte differentiation either indirectly by promoting proliferation and/or migration of stem cells, or by inhibiting apoptosis; or directly accelerating calcified cartilage formation which is the end stage of chondrocyte differentiation. In turn, the larger amount of calcified cartilage promotes new (woven) bone formation within the callus. Increased numbers of oseoblasts lining the surface of the newly formed bone have been observed which suggest a positive effect on osteoblast function.

Again these observations are consistent with the p38 MAP kinase inhibitor having no negative effect and in fact having a positive effect on fracture healing. In contrast, the development of fibrous non-unions in some of the rofecoxib treated rats was observed, as observed previously when rats were treated continuously, instead of just 5 days, with this COX-2-selective NSAID.

Appendix A

Summary of rats used for these experiments.

| Rat # | Drug Group | Purpose | Time Point | Morbidity | Data OK | Comments |
|---|---|---|---|---|---|---|
| 1 | Control | euthanized | — | PEG toxicity | — | saced due to poor appearance Oct. 25, 2001 |
| 2 | Control | mech | 4 wks | | Yes | |
| 3 | Control | histology | 4 wks | | | |
| 4 | Control | died | — | PEG toxicity | — | Found dead @am gavaging Oct. 25, 2001 |
| 5 | P38 Inhibitor | histology | 2 wks | | | |
| 6 | P38 Inhibitor | mech | 4 wks | | Yes | |
| 7 | P38 Inhibitor | euthanized | — | bad fx | — | bad fx, saced |
| 8 | P38 Inhibitor | euthanized | — | pin slippage | — | Destabilized, saced |
| 9 | Rofecoxib | histology | 8 wks | | | |
| 10 | Rofecoxib | euthanized | — | bad fx | — | bad fx, saced |
| 11 | Rofecoxib | died | — | PEG toxicity | — | Found dead @pm gavaging Oct. 31, 2001 |
| 12 | Rofecoxib | euthanized | — | bad fx | — | bad fx, saced |
| 13 | Rofecoxib | mech | 8 wks | | Yes | |
| 14 | Rofecoxib | mech | 8 wks | | Yes | |
| 15 | Rofecoxib | mech | 8 wks | MTS error | No | right femur fractured when placed into MTS |
| 16 | Rofecoxib | mech | 8 wks | | Yes | |
| 17 | P38 Inhibitor × 2 | mech | 8 wks | | Yes | |
| 18 | P38 Inhibitor × 2 | mech | 8 wks | | Yes | |
| 19 | P38 Inhibitor × 2 | died | — | PEG toxicity | — | Found dead @am gavaging Nov. 7, 2001 |
| 20 | P38 Inhibitor × 2 | died | — | PEG toxicity | — | Found dead @am gavaging Nov. 7, 2001 |
| 21 | P38 Inhibitor × 2 | mech | 8 wks | | No | poor right leg test, very high angle at failure |
| 22 | P38 Inhibitor × 2 | euthanized | — | bad fx | — | bad fx, saced |
| 23 | P38 Inhibitor × 2 | died | — | PEG toxicity | — | Found dead @am gavaging Nov. 7, 2001 |
| 24 | P38 Inhibitor × 2 | died | — | PEG toxicity | — | Found dead @am gavaging Nov. 8, 2001 |
| 25 | Rofecoxib | euthanized | — | bad fx | — | bad fx, saced |
| 26 | P38 Inhibitor | euthanized | — | pin slippage | — | Destabilized, not harvested |
| 27 | Rofecoxib | histology | 4 wks | | | |
| 28 | P38 Inhibitor × 2 | euthanized | — | bad fx | — | bad fx, saced |
| 29 | P38 Inhibitor | euthanized | — | bad fx | — | bad fx, saced |
| 30 | Control | euthanized | — | bad fx | — | bad fx, saced |
| 31 | P38 Inhibitor × 2 | histology | 4 wks | | | |
| 32 | Control | euthanized | — | bad fx | — | bad fx, saced |
| 33 | Control | histology | 4 wks | | | |
| 34 | P38 Inhibitor | mech | 6 wks | | Yes | |
| 35 | Rofecoxib | histology | 4 wks | | | |
| 36 | P38 Inhibitor × 2 | euthanized | — | bad fx | — | bad fx, saced |
| 37 | P38 Inhibitor | mech | 6 wks | | Yes | |
| 38 | P38 Inhibitor | euthanized | — | bad fx | — | bad fx, saced |
| 39 | P38 Inhibitor × 2 | euthanized | — | pin slippage | — | Destabilized, not harvested |
| 40 | P38 Inhibitor × 2 | euthanized | — | surgery | — | knee fx during surgery, saced |
| 41 | Control | histology | 2 wks | | | |
| 42 | P38 Inhibitor | histology | 2 wks | pin slippage | — | NO PIN!, harvested |
| 43 | P38 Inhibitor × 2 | histology | 2 wks | | | |
| 44 | Rofecoxib | histology | 2 wks | | | |
| 45 | P38 Inhibitor | mech | 6 wks | | Yes | |
| 46 | P38 Inhibitor × 2 | mech | 6 wks | | Yes | |
| 47 | Control | histology | 2 wks | | | |
| 48 | Rofecoxib | euthanized | — | pin slippage | — | Destabilized, not harvested |
| 49 | Rofecoxib | euthanized | — | — | — | bad fx |
| 50 | Rofecoxib | euthanized | — | — | — | bad fx |
| 51 | Rofecoxib | euthanized | — | — | — | bad fx |
| 52 | Rofecoxib | euthanized | — | — | — | bad fx |
| 53 | Rofecoxib | euthanized | — | — | — | bad fx |
| 54 | Rofecoxib | euthanized | — | — | — | bad fx |
| 55 | Rofecoxib | euthanized | — | — | — | bad fx |
| 56 | Rofecoxib | euthanized | — | — | — | bad fx |
| 57 | Rofecoxib | euthanized | — | — | — | bad fx |
| 58 | Pin test | euthanized | — | — | — | |

-continued

Summary of rats used for these experiments.

| Rat # | Drug Group | Purpose | Time Point | Morbidity | Data OK | Comments |
|---|---|---|---|---|---|---|
| 59 | Pin test | euthanized | — | | — | |
| 60 | P38 Inhibitor | mech | 4 wks | | Yes | |
| 61 | P38 Inhibitor | mech | 4 wks | | Yes | Infected?; no puss |
| 62 | Rofecoxib | histology | 2 wks | | | |
| 63 | Rofecoxib | died | — | anesthetic | — | died during surgery |
| 64 | P38 Inhibitor × 2 | mech | 4 wks | | Yes | |
| 65 | Control | mech | 4 wks | | Yes | |
| 66 | Rofecoxib | euthanized | — | pin slippage | — | Destabilized, not harvested |
| 67 | Control | mech | 4 wks | | Yes | Almost destabilized |
| 68 | P38 Inhibitor × 2 | mech | 4 wks | | Yes | |
| 69 | Rofecoxib | euthanized | — | pin slippage | — | Destabilized, not harvested |
| 70 | P38 Inhibitor × 2 | histology | 2 wks | | | |
| 71 | P38 Inhibitor | histology | 2 wks | | | |
| 72 | Rofecoxib | euthanized | — | pin slippage | — | no pin, not harvested |
| 73 | Rofecoxib | histology | 2 wks | | | |
| 74 | Control | histology | 2 wks | | | |
| 75 | P38 Inhibitor × 2 | histology | 4 wks | bad fx | — | Oblique fx |
| 76 | Control | histology | 4 wks | bad fx | — | Double fx |
| 77 | P38 Inhibitor × 2 | histology | 2 wks | | | |
| 78 | P38 Inhibitor | mech | 4 wks | | Yes | |
| 79 | P38 Inhibitor | histology | 2 wks | | | |
| 80 | Rofecoxib | mech | 4 wks | | No | Comminuted |
| 81 | Control | mech | 4 wks | | Yes | Possibly infected |
| 82 | P38 Inhibitor | histology | 2 wks | | | |
| 83 | P38 Inhibitor × 2 | histology | 4 wks | bad fx | — | Double fx |
| 84 | P38 Inhibitor | mech | 4 wks | | Yes | |
| 85 | P38 Inhibitor × 2 | mech | 4 wks | | Yes | |
| 86 | Control | histology | 2 wks | | | |
| 87 | Control | mech | 4 wks | | Yes | Comminuted? |
| 88 | Control | euthanized | — | surgery | — | pin went thru cortex, saced |
| 89 | P38 Inhibitor | euthanized | — | bad fx | — | bad fx, not harvested |
| 90 | P38 Inhibitor × 2 | mech | 4 wks | | Yes | |
| 91 | Rofecoxib | histology | 2 wks | | | |
| 92 | Control | mech | 4 wks | | Yes | Almost destabilized |
| 93 | Rofecoxib | histology | 2 wks | | | |
| 94 | P38 Inhibitor | mech | 4 wks | | Yes | |
| 95 | P38 Inhibitor × 2 | mech | 4 wks | | Yes | |
| 96 | Rofecoxib | mech | 4 wks | | Yes | |
| 97 | Rofecoxib | mech | 4 wks | | No | left leg poor test |
| 98 | Control | mech | 4 wks | | Yes | |
| 99 | Control | histology | 2 wks | | | |
| 100 | Control | histology | 2 wks | | | |
| 101 | Rofecoxib | histology | 2 wks | | | |
| 102 | P38 Inhibitor × 2 | mech | 4 wks | | Yes | |
| 103 | P38 Inhibitor | euthanized | — | pin slippage | — | Destabilized, not harvested |
| 104 | Rofecoxib | mech | 4 wks | | Yes | |
| 105 | P38 Inhibitor × 2 | histology | 2 wks | | | |
| 106 | Rofecoxib | histology | 2 wks | | | |
| 107 | Rofecoxib | mech | 4 wks | | Yes | |
| 108 | P38 Inhibitor × 2 | mech | 4 wks | | Yes | |
| 109 | Control | mech | 4 wks | | Yes | |
| 110 | Control | euthanized | — | bad fx | — | bad fx, saced |
| 111 | P38 Inhibitor × 2 | euthanized | — | infection | — | Infection, not harvested |
| 112 | Rofecoxib | histology | 4 wks | | | |
| 113 | Rofecoxib | euthanized | — | | — | Anethesia complications |
| 114 | Control | mech | 4 wks | | Yes | |
| 115 | P38 Inhibitor × 2 | mech | 4 wks | | Yes | |
| 116 | P38 Inhibitor | euthanized | — | bad fx | — | bad fx, not harvested |
| 117 | P38 Inhibitor | euthanized | — | pin slippage | — | Destabilized, not harvested |
| 118 | Control | mech | 4 wks | | Yes | |
| 119 | Control | euthanized | — | bad fx | — | bad fx, not harvested |
| 120 | Rofecoxib | Euthanized | — | pin slippage | — | Destabilized, not harvested |
| 121 | P38 Inhibitor | Euthanized | — | pin slippage | — | Destabilized, not harvested |
| 122 | Rofecoxib | Euthanized | — | pin slippage | — | Destabilized, not harvested |

-continued

Summary of rats used for these experiments.

| Rat # | Drug Group | Purpose | Time Point | Morbidity | Data OK | Comments |
|---|---|---|---|---|---|---|
| 123 | Rofecoxib | Mech | 4 wks | — | Yes | |
| 124 | Rofecoxib | Euthanized | — | pin slippage | — | Destabilized, not harvested |

Example 2 p38α MAP Kinase Inhibition Improves Clinical Scores and Blocks Cartilage and Bone Destruction in Early and Advanced Stages of Murine Collagen Type II Arthritis Destruction of cartilage and bone are poorly managed hallmarks of human rheumatoid arthritis (RA). p38 α MAP kinase has been shown to regulate key pro-inflammatory pathways in RA, including TNFα, IL-1β, and COX 2. A p38α MAP kinase inhibitor (compound 162, Table B) was evaluated to determine whether a p38 inhibitor could modulate cartilage and bone destruction in a mouse model of RA. Induction of RA was achieved using bovine type II cartilage (100 ug/kg, subcutaneous on days 0 and 21) and bacterial lipopolysaccharide (50 ug/mouse, intraperitoneal on day 22).

Oral treatment was vehicle alone (1% PEG 400, bid) or the p38 inhibitor (90 mg/kg bid). The duration of treatment was 10 and 20 days in mice with early onset or advanced disease, respectively. Treatment was initiated in mice with early onset or advanced disease. Disease state was determined by clinical scoring performed in a blinded protocol that assigned a maximum per paw value of 3 based upon degree of erythema and swelling observed. Early or advanced disease was judged by clinical scoring, 1.6+0.6 (mean+/−std dev) on day 24 and 9.1±2.6 on day 30, respectively.

Figure 9:
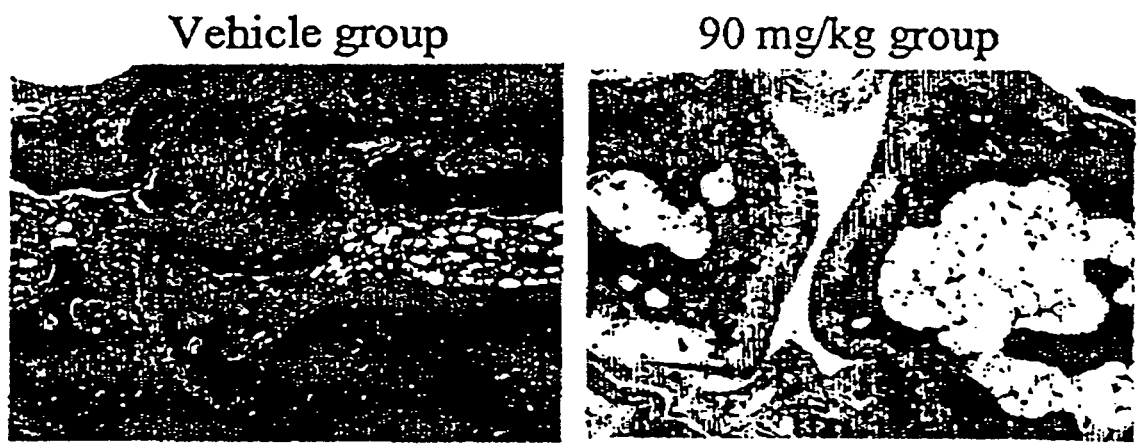
FIG. 9. Histological analysis of cartilage and bone destruction in early stage arthritis.
Figure 10A:
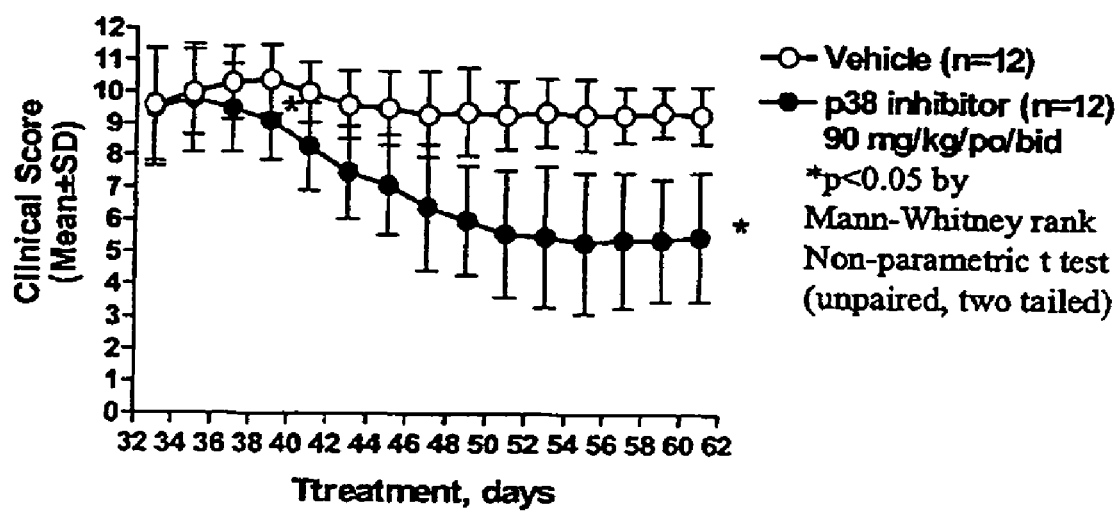
FIGS. 10A-10D.
Figure 10B:
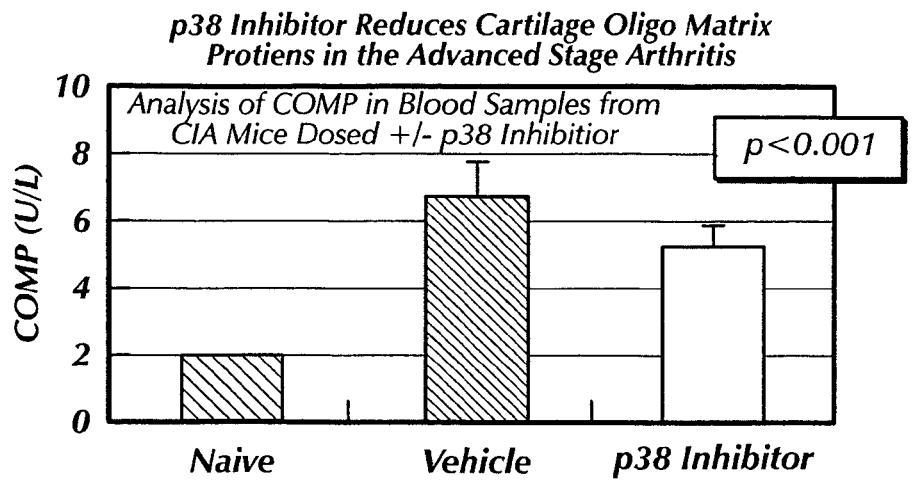
Figure 10C:
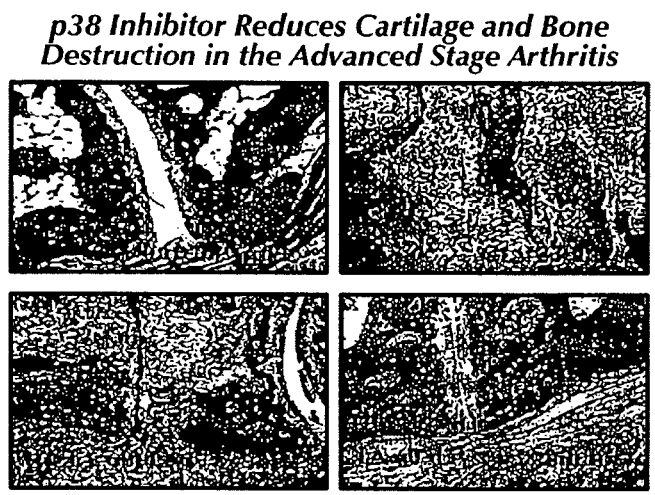
Figure 10D:
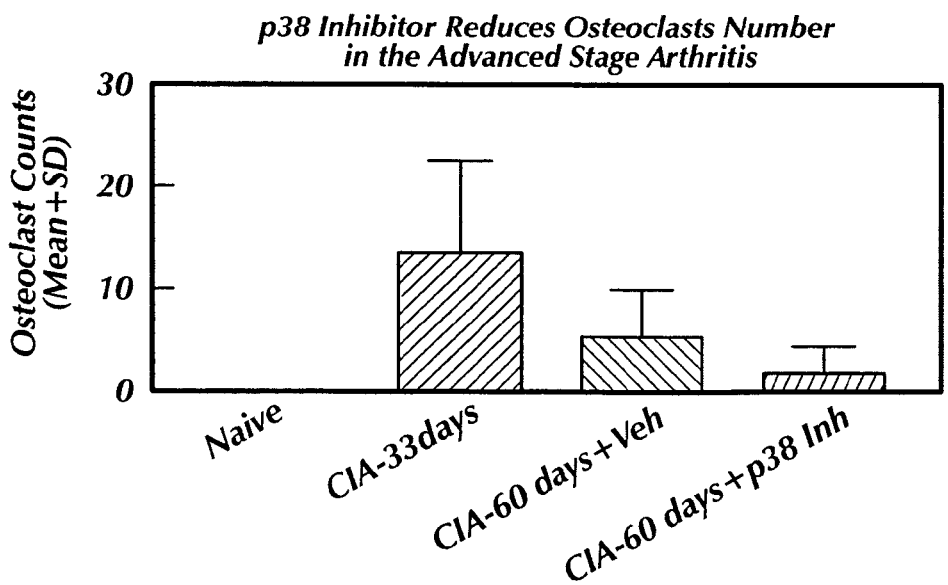

When treatment was initiated at the onset of disease, the p38 inhibitor was associated with a statistically significant improvement in clinical scoring (7.0±3.4 vs 2.4±1.5 for vehicle and the p38 inhibitor, respectively, p<0.0005 by ANOVA with Bonferroni post test). Qualitative histological evaluation included degree of bone and cartilage erosion, synovitis and pannus formation. Histological analysis showed a dramatic reduction in all aspects of joint lesion morphology including reduced cartilage and bone erosions (see, FIGS. 9A and 9B).

When treatment was initiated in mice with advanced disease there was a significant improvement in clinical scoring (9.1±2.2 vs 4.9±1.7 for vehicle and compound 25, respectively, p<0.001), reduced serum cartilage oligomeric matrix protein (COMP, a marker of cartilage breakdown) and evidence of cartilage and bone healing (osteogensis) by histological assessment, associated with reduced osteoclast number in the p38 MAP kinase inhibitor group compared to the baseline (treatment initiation) group and the vehicle treated group (FIGS. 10A, 10B, 10C and 10D).

This study demonstrates that in a model of experimental arthritis associated with significant osteolysis, p38α MAP kinase inhibition has a beneficial effect on clinical scoring and cartilage and bone destruction in early and advanced stages of the disease. Osteoclast numbers also appeared to be reduced by administration of a p38 MAP kinase inhibitor in this model.

All documents, e.g., scientific publications, patents and patent publications, recited herein are hereby incorporated by reference in their entirety to the same extent as if each individual document was specifically and individually indicated to be incorporated by reference in its entirety. Where the document cited only provides the first page of the document, the entire document is intended, including the remaining pages of the document.

The invention claimed is:

1. A method of promoting osteogenesis in a patient, said method comprising administering a pharmaceutically effective amount of a p38 mitogen activated protein (MAP) kinase inhibitor to a patient in need of osteogenesis for the treatment of a bone fracture or to enhance bone grafting.

2. The method of claim 1, wherein said p38 MAP kinase inhibitor is selected from the compounds of the formula (1):

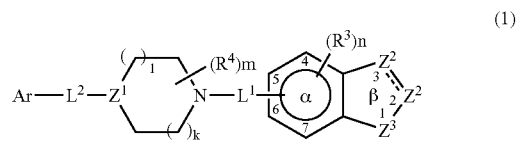

and the pharmaceutically acceptable salts thereof, or a pharmaceutical composition thereof, wherein represents a single or double bond; one $Z^2$ is CA or CR$^8$ A and the other is CR$^1$, CR$^1{}_2$, NR$^6$ or N wherein each R$^1$, R$^6$ and R$^8$ is independently hydrogen or noninterfering substituent;

A is —CO(X)$_j$Y wherein Y is COR$^2$ or an isostere thereof and R$^2$ is hydrogen or a noninterfering substituent, X is a spacer of preferably 2-6Å, and j is 0 or 1;

$Z^3$ is NR$^7$ or O, wherein R$^7$ selected from the group consisting of H, CH$_3$, COOCH$_2$CH$_3$, CON(CH$_3$)$_2$, CH$_2$CN, COOC(CH$_3$)$_3$,CH$_2$OCH$_3$, COCH$_3$, SO$_2$CH$_3$, CON(CH$_3$) $_2$, SO$_2$N(CH$_3$)$_2$, CHCOOCH$_3$, COCOC (CH$_3$)$_3$, CSCH$_3$, CH(CH$_3$)$_2$(CH$_2$) $_2$OCH$_3$CH$_2$SO$_2$CH$_3$, CH$_2$O(CH)$_2$OCH$_3$, CH$_2$OCOCH$_3$, CH$_2$OCOCH$_3$, CH$_2$OCH$_2$C6H6, CH$_2$OCH$_2$CH$_3$, (CH$_2$) $_2$N (CH$_3$)$_2$, and CH$_2$CN;

each R$^3$ is independently a noninterfering substituent;

n is 0-3;

each of L$^1$ and L$^2$ is a linker;

each R$^4$ is independently a noninterfering substituent;

m is 0-4;

$Z^1$ is CR$^5$ or N wherein R5 is hydrogen or a noninterfering substituent; each of 1 and k is an integer from 0-2 wherein the sum of 1 and k is 0-3;

Ar is an aryl group substituted with 0-5 noninterfering substituents, wherein two noninterfering substituents can form a fused ring; and the distance between the atom of Ar linked to L$^2$ and the center of the cx ring is preferably 4.5-24 Å.

3. The method of claim 1, wherein the bone fracture is a traumatic bone fracture or a long-term bone fracture.

4. The method of claim 1, wherein said p38 MAP kinase inhibitor is selective for p38α, p38β, p38γ, or p38δ.

5. The method of claim 1, wherein said patient is in need of decreased bone resorption.

6. The method of claim 1, wherein said patient is a human.

7. The method of claim 1, wherein administration of said p38 MAP kinase inhibitor decreases osteoclast numbers.

* * * * *